(12) United States Patent
Katoh et al.

(10) Patent No.: US 10,605,716 B2
(45) Date of Patent: Mar. 31, 2020

(54) PARTICLE COUNTING APPARATUS, PARTICLE COUNTING METHOD, AND PARTICLE CONTAINING SAMPLE

(71) Applicants: Ikuo Katoh, Kanagawa (JP); Manabu Seo, Kanagawa (JP); Yunong Ji, Kanagawa (JP); Nobuaki Toyoshima, Kanagawa (JP); Hiroki Somada, Shizuoka (JP); Ryuya Mashiko, Tokyo (JP); Satoshi Izumi, Tokyo (JP); Takahiko Matsumoto, Kanagawa (JP); Daisuke Takagi, Kanagawa (JP)

(72) Inventors: Ikuo Katoh, Kanagawa (JP); Manabu Seo, Kanagawa (JP); Yunong Ji, Kanagawa (JP); Nobuaki Toyoshima, Kanagawa (JP); Hiroki Somada, Shizuoka (JP); Ryuya Mashiko, Tokyo (JP); Satoshi Izumi, Tokyo (JP); Takahiko Matsumoto, Kanagawa (JP); Daisuke Takagi, Kanagawa (JP)

(73) Assignee: Ricoh Company, Ltd., Tokyo (JP)

( * ) Notice: Subject to any disclaimer, the term of this patent is extended or adjusted under 35 U.S.C. 154(b) by 0 days.

(21) Appl. No.: 16/041,603

(22) Filed: Jul. 20, 2018

(65) Prior Publication Data
US 2019/0025185 A1    Jan. 24, 2019

(30) Foreign Application Priority Data

Jul. 21, 2017  (JP) ................. 2017-142293
Jul. 13, 2018  (JP) ................. 2018-133419

(51) Int. Cl.
*G01N 15/14*   (2006.01)
*B01L 3/02*    (2006.01)

(52) U.S. Cl.
CPC ........ *G01N 15/1434* (2013.01); *B01L 3/0268* (2013.01); *G01N 15/1459* (2013.01);
(Continued)

(58) Field of Classification Search
CPC ........ G01N 21/63; G01N 21/64; G01N 21/71; G01N 21/62; G01N 21/47;
(Continued)

(56) References Cited

U.S. PATENT DOCUMENTS 3,826,364 A * 7/1974 Bonner ............... B07C 5/3425
                                              209/3.1
4,778,593 A * 10/1988 Yamashita ........... B07C 5/3427
                                              209/3.1
(Continued)

FOREIGN PATENT DOCUMENTS

JP   2000-146993   5/2000
JP   2005-201895   7/2005
(Continued)

*Primary Examiner* — Hoa Q Pham
(74) *Attorney, Agent, or Firm* — Oblon, McClelland, Maier & Neustadt, L.L.P.

(57) ABSTRACT

A particle counting apparatus is provided that includes: a droplet discharger configured to discharge a droplet containing at least one luminescent particle capable of emitting light upon receiving light; a light irradiator configured to irradiate the droplet discharged by the droplet discharger with light; at least one light receiver configured to receive light emitted by the at least one luminescent particle irradiated with the light emitted by the light irradiator; and circuitry configured to count luminescent particles contained in the droplet based on the light received by the at least one light receiver, the circuitry being configured to measure a presence or absence of the luminescent particles contained in the droplet; and to measure a number of the luminescent particles contained in the droplet.

18 Claims, 21 Drawing Sheets

(52) U.S. Cl.
CPC . *B01L 2200/0647* (2013.01); *B01L 2200/143* (2013.01); *G01N 2015/1461* (2013.01); *G01N 2015/1481* (2013.01); *G01N 2015/1486* (2013.01)

(58) Field of Classification Search
CPC ......... G01N 2021/625; G01N 15/1434; G01N 2015/1486; G01J 3/4406; G01J 3/4412
USPC .................. 356/335–343, 73; 250/483.1
See application file for complete search history.

(56) References Cited

U.S. PATENT DOCUMENTS

| | | | | |
|---|---|---|---|---|
| 2003/0143117 | A1* | 7/2003 | Nagai | G01N 15/1459 422/73 |
| 2014/0147854 | A1* | 5/2014 | Nishikawa | G01N 21/6428 435/6.12 |
| 2014/0179023 | A1* | 6/2014 | Nishikawa | G01N 15/1456 436/501 |
| 2015/0224802 | A1 | 8/2015 | Kawamichi et al. | |
| 2017/0120604 | A1 | 5/2017 | Seo et al. | |

FOREIGN PATENT DOCUMENTS

| | | |
|---|---|---|
| JP | 2007-097582 | 4/2007 |
| JP | 2008-187935 | 8/2008 |
| JP | 2010-025806 | 2/2010 |
| JP | 2010-162789 | 7/2010 |
| JP | 2011-093155 | 5/2011 |
| JP | 2011-099848 | 5/2011 |
| JP | 2011-223924 | 11/2011 |
| JP | 2014-020918 | 2/2014 |
| JP | 2014-082975 | 5/2014 |
| JP | 2015-166174 | 9/2015 |
| JP | 2017-077197 | 4/2017 |
| JP | 2017-083439 | 5/2017 |
| JP | 2018-009956 | 1/2018 |
| JP | 2018-017700 | 2/2018 |
| JP | 2018-087770 | 6/2018 |
| WO | WO 2011/099287 A1 | 8/2011 |
| WO | WO 2015/053393 A1 | 4/2015 |

* cited by examiner

FIG. 12A

| y\z | -35 | -30 | -25 | -20 | -15 | -10 | -5 | 0 | 5 | 10 | 15 | 20 | 25 | 30 | 35 |
|---|---|---|---|---|---|---|---|---|---|---|---|---|---|---|---|
| 35 |  |  |  |  | 0.1 | 0.1 | 0.3 | 0.4 | 0.5 |  |  |  |  |  |  |
| 30 |  |  | 0.1 | 0.1 | 0.3 | 0.7 | 0.9 | 0.9 | 0.9 | 0.8 | 0.8 |  |  |  |  |
| 25 |  |  | 0.0 | 0.3 | 1.4 | 1.7 | 1.5 | 1.3 | 1.2 | 1.1 | 1.1 | 1.0 | 0.9 |  |  |
| 20 |  | 0.4 | 3.0 | 3.6 | 2.4 | 2.0 | 1.7 | 1.5 | 1.4 | 1.3 | 1.2 | 1.1 | 1.0 | 1.0 |  |
| 15 |  | 5.7 | 3.7 | 2.8 | 2.3 | 2.0 | 1.8 | 1.6 | 1.5 | 1.4 | 1.2 | 1.2 | 1.1 | 1.0 |  |
| 10 | 4.9 | 3.5 | 3.2 | 2.6 | 2.3 | 2.0 | 1.8 | 1.7 | 1.5 | 1.4 | 1.3 | 1.2 | 1.1 | 1.0 | 1.0 |
| 5 | 4.7 | 4.9 | 3.2 | 2.7 | 2.3 | 2.1 | 1.9 | 1.7 | 1.5 | 1.4 | 1.3 | 1.2 | 1.1 | 1.1 | 1.0 |
| 0 | 6.3 | 12 | 6.4 | 3.2 | 2.4 | 2.1 | 1.9 | 1.7 | 1.6 | 1.4 | 1.3 | 1.2 | 1.1 | 1.1 | 1.0 |
| -5 | 4.7 | 4.9 | 3.2 | 2.7 | 2.3 | 2.1 | 1.9 | 1.7 | 1.5 | 1.4 | 1.3 | 1.2 | 1.1 | 1.1 | 1.0 |
| -10 | 4.9 | 3.5 | 3.2 | 2.6 | 2.3 | 2.0 | 1.8 | 1.7 | 1.5 | 1.4 | 1.3 | 1.2 | 1.1 | 1.0 | 1.0 |
| -15 |  | 5.7 | 3.7 | 2.8 | 2.3 | 2.0 | 1.8 | 1.6 | 1.5 | 1.4 | 1.2 | 1.2 | 1.1 | 1.0 |  |
| -20 |  | 0.4 | 3.0 | 3.6 | 2.4 | 2.0 | 1.7 | 1.5 | 1.4 | 1.3 | 1.2 | 1.1 | 1.0 | 1.0 |  |
| -25 |  |  | 0.0 | 0.3 | 1.4 | 1.7 | 1.5 | 1.3 | 1.2 | 1.1 | 1.1 | 1.0 | 0.9 |  |  |
| -30 |  |  | 0.1 | 0.1 | 0.3 | 0.7 | 0.9 | 0.9 | 0.9 | 0.8 | 0.8 |  |  |  |  |
| -35 |  |  |  |  | 0.1 | 0.1 | 0.3 | 0.4 | 0.5 |  |  |  |  |  |  |

FIG. 12B

| y\z | -35 | -30 | -25 | -20 | -15 | -10 | -5 | 0 | 5 | 10 | 15 | 20 | 25 | 30 | 35 |
|---|---|---|---|---|---|---|---|---|---|---|---|---|---|---|---|
| 35 |  |  |  |  | 0.6 | 0.5 | 0.5 | 0.5 | 0.6 |  |  |  |  |  |  |
| 30 |  |  | 0.8 | 0.9 | 1.2 | 1.7 | 1.8 | 1.7 | 1.2 | 0.9 | 0.8 |  |  |  |  |
| 25 |  |  | 0.9 | 1.3 | 2.5 | 2.8 | 2.7 | 2.7 | 2.7 | 2.8 | 2.5 | 1.3 | 0.9 |  |  |
| 20 |  | 1.4 | 4 | 4.6 | 3.6 | 3.3 | 3.1 | 3.1 | 3.1 | 3.3 | 3.6 | 4.6 | 4 | 1.4 |  |
| 15 |  | 6.7 | 4.8 | 3.9 | 3.6 | 3.4 | 3.3 | 3.3 | 3.3 | 3.4 | 3.6 | 3.9 | 4.8 | 6.7 |  |
| 10 | 5.9 | 4.5 | 4.3 | 3.8 | 3.6 | 3.4 | 3.4 | 3.3 | 3.4 | 3.4 | 3.6 | 3.8 | 4.3 | 4.5 | 5.9 |
| 5 | 5.7 | 6 | 4.3 | 3.9 | 3.6 | 3.5 | 3.4 | 3.4 | 3.4 | 3.5 | 3.6 | 3.9 | 4.3 | 6 | 5.7 |
| 0 | 7.3 | 13 | 7.5 | 4.5 | 3.7 | 3.5 | 3.4 | 3.4 | 3.4 | 3.5 | 3.7 | 4.5 | 7.5 | 13 | 7.3 |
| -5 | 5.7 | 6 | 4.3 | 3.9 | 3.6 | 3.5 | 3.4 | 3.4 | 3.4 | 3.5 | 3.6 | 3.9 | 4.3 | 6 | 5.7 |
| -10 | 5.9 | 4.5 | 4.3 | 3.8 | 3.6 | 3.4 | 3.4 | 3.3 | 3.4 | 3.4 | 3.6 | 3.8 | 4.3 | 4.5 | 5.9 |
| -15 |  | 6.7 | 4.8 | 3.9 | 3.6 | 3.4 | 3.3 | 3.3 | 3.3 | 3.4 | 3.6 | 3.9 | 4.8 | 6.7 |  |
| -20 |  | 1.4 | 4 | 4.6 | 3.6 | 3.3 | 3.1 | 3.1 | 3.1 | 3.3 | 3.6 | 4.6 | 4 | 1.4 |  |
| -25 |  |  | 0.9 | 1.3 | 2.5 | 2.8 | 2.7 | 2.7 | 2.7 | 2.8 | 2.5 | 1.3 | 0.9 |  |  |
| -30 |  |  | 0.8 | 0.9 | 1.2 | 1.7 | 1.8 | 1.7 | 1.2 | 0.9 | 0.8 |  |  |  |  |
| -35 |  |  |  |  | 0.6 | 0.5 | 0.5 | 0.5 | 0.6 |  |  |  |  |  |  |

FIG. 17A

| y \ z | -35 | -30 | -25 | -20 | -15 | -10 | -5 | 0 | 5 | 10 | 15 | 20 | 25 | 30 | 35 |
|---|---|---|---|---|---|---|---|---|---|---|---|---|---|---|---|
| 35 | | | | | | 0.6 | 0.5 | 0.4 | 0.1 | 0.0 | | | | | |
| 30 | | | 0.8 | 0.9 | 0.9 | 0.9 | 1.0 | 0.9 | 0.4 | 0.0 | 0.0 | | | | |
| 25 | | 0.9 | 1.0 | 1.0 | 1.1 | 1.2 | 1.4 | 1.5 | 1.8 | 1.6 | 0.2 | 0.0 | | | |
| 20 | 0.9 | 1.0 | 1.1 | 1.2 | 1.3 | 1.4 | 1.5 | 1.7 | 2.0 | 2.5 | 3.7 | 3.2 | 0.0 | | |
| 15 | | 1.0 | 1.1 | 1.1 | 1.2 | 1.3 | 1.5 | 1.6 | 1.8 | 2.0 | 2.3 | 2.7 | 3.4 | 6.7 | |
| 10 | 1.0 | 1.0 | 1.1 | 1.2 | 1.3 | 1.4 | 1.5 | 1.6 | 1.8 | 2.0 | 2.2 | 2.5 | 2.9 | 3.3 | 4.4 |
| 5 | 1.0 | 1.1 | 1.1 | 1.2 | 1.3 | 1.4 | 1.5 | 1.7 | 1.8 | 2.0 | 2.2 | 2.4 | 2.7 | 3.0 | 3.5 |
| 0 | 1.0 | 1.1 | 1.1 | 1.2 | 1.3 | 1.4 | 1.5 | 1.7 | 1.8 | 2.0 | 2.2 | 2.4 | 2.7 | 3.0 | 3.3 |
| -5 | 1.0 | 1.1 | 1.1 | 1.2 | 1.3 | 1.4 | 1.5 | 1.7 | 1.8 | 2.0 | 2.2 | 2.4 | 2.7 | 3.0 | 3.5 |
| -10 | 1.0 | 1.0 | 1.1 | 1.2 | 1.3 | 1.4 | 1.5 | 1.6 | 1.8 | 2.0 | 2.2 | 2.5 | 2.9 | 3.3 | 4.4 |
| -15 | | 1.0 | 1.1 | 1.1 | 1.2 | 1.3 | 1.5 | 1.6 | 1.8 | 2.0 | 2.3 | 2.7 | 3.4 | 6.7 | |
| -20 | 0.9 | 1.0 | 1.1 | 1.2 | 1.3 | 1.4 | 1.5 | 1.7 | 2.0 | 2.5 | 3.7 | 3.2 | 0.0 | | |
| -25 | | 0.9 | 1.0 | 1.0 | 1.1 | 1.2 | 1.4 | 1.5 | 1.8 | 1.6 | 0.2 | 0.0 | | | |
| -30 | | | 0.8 | 0.9 | 0.9 | 0.9 | 1.0 | 0.9 | 0.4 | 0.0 | 0.0 | | | | |
| -35 | | | | | | 0.6 | 0.5 | 0.4 | 0.1 | 0.0 | | | | | |

FIG. 17B

| y \ z | -35 | -30 | -25 | -20 | -15 | -10 | -5 | 0 | 5 | 10 | 15 | 20 | 25 | 30 | 35 |
|---|---|---|---|---|---|---|---|---|---|---|---|---|---|---|---|
| 35 | | | | | | 1.0 | 1.0 | 0.9 | 0.9 | 0.8 | | | | | |
| 30 | | | 1.0 | 1.0 | 1.0 | 1.0 | 1.1 | 1.0 | 1.0 | 0.7 | 0.6 | | | | |
| 25 | | 1.0 | 1.0 | 1.1 | 1.1 | 1.2 | 1.2 | 1.2 | 1.1 | 1.1 | 0.7 | 0.4 | | | |
| 20 | 1.0 | 1.0 | 1.1 | 1.1 | 1.2 | 1.2 | 1.2 | 1.3 | 1.3 | 1.3 | 1.2 | 0.6 | 0.1 | | |
| 15 | | 1.0 | 1.1 | 1.1 | 1.2 | 1.3 | 1.3 | 1.2 | 1.4 | 1.5 | 1.5 | 1.5 | 1.1 | 0.2 | |
| 10 | 1.0 | 1.0 | 1.1 | 1.2 | 1.3 | 1.3 | 1.4 | 1.5 | 1.6 | 1.6 | 1.7 | 2.0 | 1.8 | 0.8 | 0.0 |
| 5 | 1.0 | 1.0 | 1.2 | 1.2 | 1.3 | 1.4 | 1.5 | 1.6 | 1.7 | 1.7 | 1.9 | 2.0 | 2.5 | 0.9 | 0.1 |
| 0 | 0.9 | 1.1 | 1.2 | 1.2 | 1.4 | 1.5 | 1.6 | 1.7 | 1.7 | 1.9 | 2.0 | 2.3 | 2.8 | 3.7 | 0.0 |
| -5 | 0.9 | 1.0 | 1.2 | 1.3 | 1.4 | 1.6 | 1.7 | 1.7 | 1.9 | 2.0 | 2.2 | 2.4 | 2.7 | 3.3 | 1.6 |
| -10 | 0.8 | 1.0 | 1.1 | 1.3 | 1.5 | 1.6 | 1.7 | 1.9 | 2.0 | 2.2 | 2.3 | 2.5 | 2.9 | 5.1 | 2.8 |
| -15 | | 0.7 | 1.1 | 1.3 | 1.5 | 1.7 | 1.9 | 2.0 | 2.2 | 2.3 | 2.4 | 2.7 | 3.0 | 3.9 | |
| -20 | | 0.6 | 0.7 | 1.2 | 1.5 | 2.0 | 2.0 | 2.3 | 2.4 | 2.5 | 2.7 | 2.8 | 3.2 | 3.9 | |
| -25 | | | 0.4 | 0.6 | 1.1 | 1.8 | 2.5 | 2.8 | 2.7 | 2.9 | 3.0 | 3.2 | 3.3 | | |
| -30 | | | | 0.1 | 0.2 | 0.8 | 0.9 | 3.7 | 3.3 | 5.1 | 3.9 | 3.9 | | | |
| -35 | | | | | | 0.0 | 0.1 | 0.0 | 1.6 | 2.8 | | | | | |

FIG. 17C

| y, z | -35 | -30 | -25 | -20 | -15 | -10 | -5 | 0 | 5 | 10 | 15 | 20 | 25 | 30 | 35 |
|---|---|---|---|---|---|---|---|---|---|---|---|---|---|---|---|
| 35  |     |     |     |     |     | 0.8 | 0.7 | 0.6 | 0.5 | 0.4 |     |     |     |     |     |
| 30  |     |     |     | 0.9 | 0.9 | 1.0 | 1.0 | 1.0 | 0.9 | 0.7 | 0.4 | 0.3 |     |     |     |
| 25  |     |     | 1.0 | 1.0 | 1.1 | 1.1 | 1.2 | 1.3 | 1.4 | 1.4 | 1.3 | 0.4 | 0.2 |     |     |
| 20  |     | 1.0 | 1.0 | 1.1 | 1.2 | 1.2 | 1.3 | 1.4 | 1.5 | 1.7 | 1.9 | 2.5 | 1.9 | 0.0 |     |
| 15  |     | 1.0 | 1.1 | 1.1 | 1.2 | 1.3 | 1.4 | 1.4 | 1.6 | 1.8 | 1.9 | 2.1 | 2.3 | 3.5 |     |
| 10  | 1.0 | 1.0 | 1.1 | 1.2 | 1.3 | 1.4 | 1.5 | 1.6 | 1.7 | 1.8 | 1.9 | 2.2 | 2.3 | 2.1 | 2.2 |
| 5   | 1.0 | 1.0 | 1.1 | 1.2 | 1.3 | 1.4 | 1.5 | 1.6 | 1.7 | 1.9 | 2.0 | 2.2 | 2.6 | 2.0 | 1.8 |
| 0   | 1.0 | 1.1 | 1.2 | 1.2 | 1.4 | 1.4 | 1.6 | 1.7 | 1.8 | 1.9 | 2.1 | 2.4 | 2.7 | 3.4 | 1.7 |
| -5  | 0.9 | 1.0 | 1.2 | 1.3 | 1.4 | 1.5 | 1.6 | 1.7 | 1.9 | 2.0 | 2.2 | 2.4 | 2.7 | 3.2 | 2.5 |
| -10 | 0.9 | 1.0 | 1.1 | 1.3 | 1.4 | 1.5 | 1.6 | 1.8 | 1.9 | 2.1 | 2.3 | 2.5 | 2.9 | 4.2 | 3.6 |
| -15 |     | 0.9 | 1.1 | 1.2 | 1.4 | 1.5 | 1.7 | 1.8 | 2.0 | 2.2 | 2.4 | 2.7 | 3.2 | 5.3 |     |
| -20 |     | 0.7 | 0.8 | 1.1 | 1.3 | 1.6 | 1.7 | 1.9 | 2.1 | 2.2 | 2.6 | 3.3 | 3.2 | 2.0 |     |
| -25 |     |     | 0.6 | 0.8 | 1.1 | 1.4 | 1.8 | 2.1 | 2.1 | 2.3 | 2.3 | 1.7 | 1.7 |     |     |
| -30 |     |     |     | 0.4 | 0.5 | 0.8 | 0.9 | 2.3 | 2.1 | 2.7 | 1.9 | 2.0 |     |     |     |
| -35 |     |     |     |     |     | 0.3 | 0.3 | 0.2 | 0.8 | 1.4 |     |     |     |     |     |

| y, z | -35 | -30 | -25 | -20 | -15 | -10 | -5 | 0 | 5 | 10 | 15 | 20 | 25 | 30 | 35 |
|---|---|---|---|---|---|---|---|---|---|---|---|---|---|---|---|
| 35 | | | | | | 0.3 | 0.3 | 0.4 | 0.3 | 0.3 | | | | | |
| 30 | | | | | 0.4 | 0.4 | 0.6 | 0.9 | 1.0 | 0.9 | 0.6 | 0.4 | 0.4 | | |
| 25 | | | | 0.5 | 0.6 | 1.3 | 1.4 | 1.4 | 1.4 | 1.4 | 1.4 | 1.3 | 0.6 | 0.5 | |
| 20 | | | 0.5 | 2.1 | 2.4 | 1.8 | 1.6 | 1.6 | 1.5 | 1.6 | 1.6 | 1.8 | 2.4 | 2.1 | 0.5 |
| 15 | | | 3.9 | 2.2 | 1.9 | 1.8 | 1.7 | 1.6 | 1.6 | 1.6 | 1.7 | 1.8 | 1.9 | 2.2 | 3.9 |
| 10 | 2.7 | 2.2 | 2.0 | 1.9 | 1.8 | 1.7 | 1.7 | 1.6 | 1.7 | 1.7 | 1.8 | 1.9 | 2.0 | 2.2 | 2.7 |
| 5 | 2.2 | 2.1 | 1.9 | 1.8 | 1.8 | 1.7 | 1.7 | 1.7 | 1.7 | 1.7 | 1.8 | 1.8 | 1.9 | 2.1 | 2.2 |
| 0 | 2.2 | 2.0 | 1.9 | 1.8 | 1.8 | 1.7 | 1.7 | 1.7 | 1.7 | 1.7 | 1.8 | 1.8 | 1.9 | 2.0 | 2.2 |
| -5 | 2.2 | 2.1 | 1.9 | 1.8 | 1.8 | 1.7 | 1.7 | 1.7 | 1.7 | 1.7 | 1.8 | 1.8 | 1.9 | 2.1 | 2.2 |
| -10 | 2.7 | 2.2 | 2.0 | 1.9 | 1.8 | 1.7 | 1.7 | 1.6 | 1.7 | 1.7 | 1.8 | 1.9 | 2.0 | 2.2 | 2.7 |
| -15 | | | 3.9 | 2.2 | 1.9 | 1.8 | 1.7 | 1.6 | 1.6 | 1.6 | 1.7 | 1.8 | 1.9 | 2.2 | 3.9 |
| -20 | | | 0.5 | 2.1 | 2.4 | 1.8 | 1.6 | 1.6 | 1.5 | 1.6 | 1.6 | 1.8 | 2.4 | 2.1 | 0.5 |
| -25 | | | | 0.5 | 0.6 | 1.3 | 1.4 | 1.4 | 1.4 | 1.4 | 1.4 | 1.3 | 0.6 | 0.5 | |
| -30 | | | | | 0.4 | 0.4 | 0.6 | 0.9 | 1.0 | 0.9 | 0.6 | 0.4 | 0.4 | | |
| -35 | | | | | | 0.3 | 0.3 | 0.4 | 0.3 | 0.3 | | | | | |

PARTICLE COUNTING APPARATUS, PARTICLE COUNTING METHOD, AND PARTICLE CONTAINING SAMPLE

CROSS-REFERENCE TO RELATED APPLICATIONS

This patent application is based on and claims priority pursuant to 35 U.S.C. § 119(a) to Japanese Patent Application Nos. 2017-142293 filed Jul. 21, 2017 and 2018-133419 filed Jul. 13, 2018, in the Japan Patent Office, the entire disclosure of which is hereby incorporated by reference herein.

BACKGROUND

Technical Field

The present disclosure relates to a particle counting apparatus, a particle counting method, and a particle containing sample.

Description of the Related Art

In recent years, techniques for discharging a plurality of cells by inkjet to form tissues have been developed with the progress of stem cell technology. It may be important to count how much particles are contained in the discharged droplet when it contains particulate matter as typified by cells.

As an example of a device having such a function, a discharge apparatus that detects the number of granular bodies contained in a liquid body has been proposed. In this discharge apparatus, the number of particles contained in the liquid body is counted when the liquid body is passing through a detection portion provided between a cavity and a nozzle in the discharge apparatus.

As another example, a microparticle measuring apparatus has been proposed that detects fluorescence generated from microparticles upon irradiation with excitation light to droplets containing the microparticles. This microparticle measuring apparatus is capable of detecting fluorescence generated from the microparticles contained in droplets while the droplets are flying.

SUMMARY

In an embodiment, a particle counting apparatus is provided that includes: a droplet discharger configured to discharge a droplet containing at least one luminescent particle capable of emitting light upon receiving light; a light irradiator configured to irradiate the droplet discharged by the droplet discharger with light; at least one light receiver configured to receive light emitted by the at least one luminescent particle irradiated with the light emitted by the light irradiator; and circuitry configured to count luminescent particles contained in the droplet based on the light received by the at least one light receiver, the circuitry being configured to measure a presence or absence of the luminescent particles contained in the droplet; and to measure a number of the luminescent particles contained in the droplet.

In an embodiment, the circuitry includes: a first particle measuring device being configured to measure the presence or absence of the luminescent particles contained in the droplet; and a second particle measuring device being configured to measure the number of the luminescent particles contained in the droplet.

In an embodiment, the circuitry is configured to measure the number of the luminescent particles contained in the droplet, based on information from the first particle measuring device that a luminescent particle is present in the droplet; and control the droplet discharger, based on information from the second particle measuring device on the number of the luminescent particles contained in the droplet, or based on information from the first particle measuring device that a luminescent particle is absent in the droplet without using any information from the second particle measuring device.

In an embodiment, the circuitry is configured to control a droplet discharge position such that droplets are continuously discharged to a substantially same position based on information from the first particle measuring device that a luminescent particle is absent in the droplet.

In an embodiment, the first particle measuring device is configured to acquire an amount of light emitted by the at least one luminescent particle, wherein the second particle measuring device is configured to acquire a two-dimensional image based on the light emitted by the at least one luminescent particle.

In an embodiment, the at least one light receiver includes two or more light receivers configured to receive light beams emitted in two or more different directions, respectively, and a first light receiver of the two or more light receivers is coupled to the first particle measuring device.

In an embodiment, a second light receiver of the two or more light receivers is coupled to the second particle measuring device.

In an embodiment, the first particle measuring device acquires the amount of light emitted by the at least one luminescent particle based on the two-dimensional image acquired by the second particle measuring device.

In an embodiment, the light irradiator is configured to emit light from two or more different directions.

In an embodiment, the two or more different directions are substantially opposite directions to each other.

In an embodiment, the light irradiator includes: a first light irradiator configured to irradiate the droplet with a substantially parallel light flux; and a second light irradiator including an optical deflector element, configured to deflect the substantially parallel light flux transmitted the droplet, in response to irradiation of the droplet with a part of the substantially parallel light flux, to irradiate the droplet again.

In an embodiment, the light irradiator is configured to emit light in synchronization with the discharge of the droplet from the droplet discharger.

In an embodiment, the synchronization is based on the light irradiator emitting the light with a delay of a predetermined time period from the discharge of the droplet from the droplet discharger.

In an embodiment, the at least one light receiver is configured to receive the light in synchronization with the emission of the light by the light irradiator.

In an embodiment, a count information storage storing information on the number of particles counted by the particle counting apparatus.

In an embodiment, a second light receiver of the two or more light receivers includes a field programmable gate array (FPGA).

In an embodiment, a particle counting method is provided implemented by a particle counting apparatus, including: discharging, by a droplet discharger, a droplet containing at least one luminescent particle capable of emitting light upon receiving light; irradiating, by a light irradiator, the droplet discharged in the discharging with light; receiving, by at least one light receiver, light emitted by the at least one luminescent particle irradiated with the light; an counting, by circuitry, luminescent particles contained in the droplet based on the light received in the receiving, the counting including: firstly measuring a presence or absence of the luminescent particles contained in the droplet; and secondly measuring the number of the luminescent particles contained in the droplet.

In an embodiment, the particle counting method includes controlling, by the circuitry, the counting such that the number of the luminescent particles contained in the droplet is measured in the secondly measuring based on information from the firstly measuring that a luminescent particle is present in the droplet; and controlling, by the circuitry, the discharging, based on information from the secondly measuring on the number of the luminescent particles contained in the droplet, or based on information from the firstly measuring that a luminescent particle is absent in the droplet without using any information from the secondly measuring.

In an embodiment, the controlling the discharging includes accumulating the number of luminescent particles based on the information from the secondly measuring on the number of the luminescent particles contained in the droplet.

In an embodiment, the method includes controlling, by the circuitry, a droplet discharge position such that droplets are continuously discharged to a substantially same position based on information from the firstly measuring that a luminescent particle is absent in the droplet; and moving the droplet discharge position based on information from the controlling.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 12A is a diagram illustrating a distribution of the amount of light received in the particle counting apparatus according to the fourth embodiment;

FIG. 12B is a schematic diagram illustrating another distribution of the amount of light received in the particle counting apparatus according to the fourth embodiment;

FIG. 17A is a diagram illustrating a distribution of the amount of illumination light in the particle counting apparatus according to the first embodiment;

FIG. 17B is a diagram illustrating a distribution of the amount of illumination light in the particle counting apparatus according to the seventh embodiment;

FIG. 17C is a diagram illustrating another distribution of the amount of illumination light in the particle counting apparatus according to the seventh embodiment;

Figure 1:
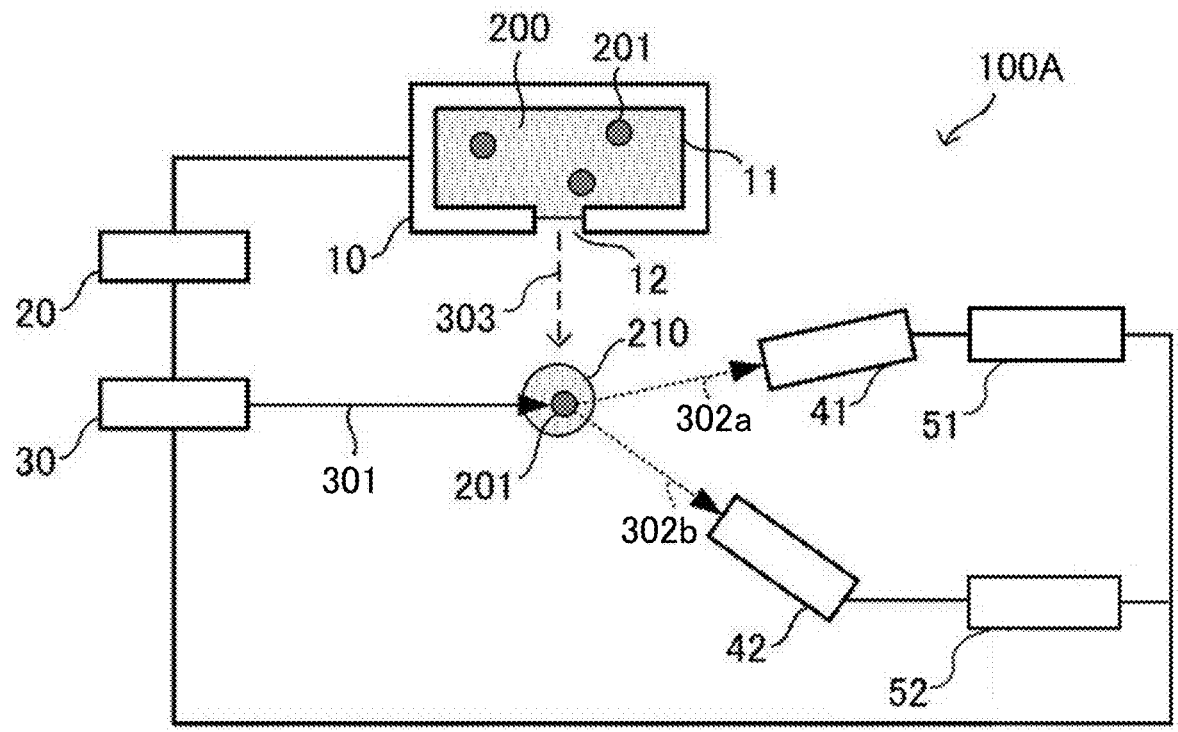
FIG. 1 is a schematic diagram of a particle counting apparatus according to a first embodiment.

The accompanying drawings are intended to depict example embodiments and should not be interpreted to limit the scope thereof. The accompanying drawings are not to be considered as drawn to scale unless explicitly noted.

DETAILED DESCRIPTION

The terminology used herein is for the purpose of describing particular embodiments only and is not intended to be limiting of the claimed invention. As used herein, the singular forms "a", "an" and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

Embodiments are described in detail below with reference to accompanying drawings. In describing embodiments illustrated in the drawings, specific terminology is employed for the sake of clarity. However, the disclosure of this patent specification is not intended to be limited to the specific terminology so selected, and it is to be understood that each specific element includes all technical equivalents that have a similar function, operate in a similar manner, and achieve a similar result.

For the sake of simplicity, the same reference number will be given to identical constituent elements such as parts and materials having the same functions and redundant descriptions thereof omitted unless otherwise stated.

In accordance with some embodiments, a particle counting apparatus is provided that is capable of counting the number of particles contained in a discharged droplet with a high degree of accuracy.

Particle Counting Apparatus and Particle Counting Method

A particle counting apparatus according to an embodiment includes: a droplet discharger configured to discharge a droplet containing a luminescent particle capable of emitting light upon receiving light; a light irradiator configured to irradiate the droplet discharged by the droplet discharger with light; a light receiver configured to receive light emitted by the luminescent particle irradiated with the light emitted by the light irradiator; and a particle counter configured to count the luminescent particle contained in the droplet based on the light received by the light receiver. The particle counter includes: a first particle measuring device configured to measure a presence or absence of the luminescent particle contained in the droplet; and a second particle measuring device configured to measure the number of the luminescent particle contained in the droplet.

The present embodiments are achieved based on a finding that, in a conventional discharge apparatus, the number of particles contained in a liquid body immediately before starting flying is counted, instead of directly counting the number of particles contained in the flying droplet. Accordingly, the number of particles contained in the liquid body before flying does not necessarily coincide with the number of particles contained in the flying droplet, resulting in a low degree of accuracy in detecting the number of particles contained in the discharged droplet.

The present embodiments are also achieved based on another finding that a conventional microparticle measuring apparatus does measure the shape or fluorescence intensity of a droplet but does not measure the number of particles contained in the droplet.

A particle counting method according to an embodiment includes the processes of: discharging a droplet containing a luminescent particle capable of emitting light upon receiving light; irradiating the droplet discharged in the discharging process with light; receiving light emitted by the luminescent particle irradiated with the light; and counting the luminescent particle contained in the droplet based on the light received in the receiving process. The counting process includes: firstly measuring a presence or absence of the luminescent particle contained in the droplet; and secondly measuring the number of the luminescent particle contained in the droplet.

The particle counting method according to an embodiment is preferably performed by the particle counting apparatus according to an embodiment. When a counting procedure is carried out using the particle counting apparatus according an embodiment, the particle counting method according to an embodiment is carried out.

Hereinafter, embodiments are described with reference to the attached drawings. In the drawings, the same reference numerals are given to the same components, and redundant explanation may be omitted.

When the particle counting method is carried out, a counting procedure is carried out using the particle counting apparatus. Therefore, the particle counting method will be explained by explaining the particle counting apparatus.

First Embodiment

A particle counting apparatus according to a first embodiment includes: a droplet discharger configured to discharge a droplet containing a luminescent particle capable of emitting light upon receiving light; a light irradiator configured to irradiate the droplet discharged by the droplet discharger with light; a light receiver configured to receive light emitted by the luminescent particle irradiated with the light emitted by the light irradiator; and a particle counter configured to count the luminescent particle contained in the droplet based on the light received by the light receiver. The particle counter includes: a first particle measuring device configured to measure a presence or absence of the luminescent particle contained in the droplet; and a second particle measuring device configured to measure the number of the luminescent particle contained in the droplet. The particle counting apparatus may optionally include other members.

A particle counting method according to a first embodiment includes the processes of: discharging a droplet containing a luminescent particle capable of emitting light upon receiving light; irradiating the droplet discharged in the discharging process with light; receiving light emitted by the luminescent particle irradiated with the light; and counting the luminescent particle contained in the droplet based on the light received in the receiving process. The counting process includes: firstly measuring a presence or absence of the luminescent particle contained in the droplet; and secondly measuring the number of the luminescent particle contained in the droplet. The particle counting method may optionally include other processes.

The discharging process is preferably performed by the droplet discharger. The irradiating process is preferably performed by the light irradiator. The receiving process is preferably performed by the light receiver. The counting process is preferably performed by the particle counter. The firstly measuring process is preferably performed by the first particle measuring device. The secondly measuring process is preferably performed by the second particle measuring device. The other processes are preferably performed by the other respective members.

Preferably, the first particle measuring device includes a light emission amount acquisition unit configured to acquire an amount of light emitted by the luminescent particle, and the second particle measuring device includes a two-dimensional image acquisition unit configured to acquire a two-dimensional image based on the light emitted by the luminescent particle.

FIG. 1 is a schematic diagram of a particle counting apparatus according to the first embodiment. Referring to FIG. 1, a particle counting apparatus 100A includes a droplet discharger 10 equipped with a liquid chamber 11 and a nozzle 12, a driver 20, a light irradiator 30, light receivers 41 and 42, a first particle measuring device 51, and a second particle measuring device 52. A particle suspension 200 contains particles 201 capable of emitting light upon receiving light (hereinafter "luminescent particles 201"). A droplet 210 is discharged from the nozzle 12 of the droplet discharger 10 in a discharge direction 303. Laser beam 301 is emitted by the light irradiator 30. Light beam 302a is received by the light receiver 41. Light beam 302b is received by the light receiver 42. The light receiver 41 and the light receiver 42 are coupled to the first particle measuring device 51 and the second particle measuring device 52, respectively.

As illustrated in FIG. 1, the droplet discharger 10 stores the particle suspension 200 in which the luminescent particles 201 are suspended in the liquid chamber 11. As a piezoelectric element disposed in the liquid chamber 11 deforms, the droplet 210 in a spherical, ellipsoidal, or slightly-deformed spherical or ellipsoidal shape and containing the luminescent particle 201 is discharged in the discharge direction 303.

The droplet discharger 10 discharges a droplet containing a luminescent particle capable of emitting light upon receiving light. The droplet discharger 10 is not particularly limited and can be appropriately selected according to the purpose. Examples of the droplet discharger 10 include, but are not limited to, a piezoelectric pressure inkjet head using a piezoelectric element, a thermal inkjet head using a heater, an electrostatic inkjet head that guides a liquid by an electrostatic force, and a membrane vibration inkjet head using a piezoelectric element. Among these examples, a membrane vibration inkjet head is preferable. The membrane vibration inkjet head discharges droplets by an inertial force generated by vibration. Since the upper part of the inkjet head can be released to the atmosphere, damage to the particle caused by heat, electric field, pressure, or the like, can be reduced, particularly when the particle is a cell. The piezoelectric element used for the membrane vibration ink jet head is not particularly limited and can be appropriately selected according to the purpose. For example, an element using lead zirconate titanate (PZT) is preferable.

The liquid chamber 11 is a liquid retaining part that retains the particle suspension 200 in which the luminescent particles 201 are suspended. The nozzle 12 that is a through hole is formed on a lower surface of the liquid chamber 11. The liquid chamber 11 may be made of, for example, metal, silicon, or ceramic. The driver 20 is electrically coupled to the piezoelectric element of the droplet discharger 10. The driver 20 applies a drive voltage to the piezoelectric element to deform the piezoelectric element, thereby discharging the droplet 210 containing the luminescent particle 201 in the discharge direction 303. The luminescent particle 201 is capable of emitting fluorescence upon receiving illumination light. (Therefore, the luminescent particle 201 may be hereinafter also referred to as "fluorescent particle 201".) Examples of the fluorescent particle 201 include, but are not limited to, an inorganic particle stained with a fluorescent dye, an organic polymer particle stained with a fluorescent dye, a cell stained with a fluorescent dye, and a fluorescent protein. In addition, particles that emit Raman scattering light, not fluorescent light, may also be used as the luminescent particle 201.

The organic polymer particle stained with a fluorescent dye is not particularly limited and can be appropriately selected according to the purpose. Examples thereof include, but are not limited to, SPHERO™ FLUORESCENT NILE RED PARTICLES (manufactured by Bay bioscience Co., Ltd., 1% (w/v), having a diameter of 10 to 14 µm).

The cell to be stained with a fluorescent dye is not particularly limited and can be appropriately selected according to the purpose. All types of cells are usable regardless of whether the cells are, for example, eukaryotic cells, prokaryotic cells, multicellular organism cells, or unicellular organism cells. Each of these examples may be used alone, or two or more of the examples may be used in combination.

The eukaryotic cells are not particularly limited and can be appropriately selected according to the purpose. Examples of the eukaryotic cells include, but are not limited to, animal cells, insect cells, plant cells, fungi, algae, and protozoans. Each of these examples may be used alone, or two or more of the examples may be used in combination. Among these examples, animal cells and fungi are preferable.

Adherent cells, including either primary cells directly collected from tissues or organs or cells obtained by subculturing the primary cells directly collected from tissues or organs, may also be used. Examples of the adherent cells include, but are not limited to, differentiated cells and undifferentiated cells.

The differentiated cells are not particularly limited and can be appropriately selected according to the purpose. Examples of the differentiated cells include, but not limited to: hepatocytes that are parenchymal cells of the liver; stellate cells; Kupffer cells; vascular endothelial cells; endothelial cells, such as ductal endothelial cells and corneal endothelial cells; fibroblasts; osteoblasts; osteoclasts; periodontal ligament fibroblasts; epidermal cells, such as epidermal keratinocytes; tracheal epithelial cells; gastrointestinal epithelial cells; cervical epithelial cells; epithelial cells such as corneal epithelial cells; mammary gland cells; pericytes; muscle cells, such as smooth muscle cells and cardiac muscle cells; renal cells; pancreatic islets of Langerhans cells; nerve cells, such as peripheral nerve cells and optic nerve cells; cartilage cells; and bone cells.

The undifferentiated cells are not particularly limited and can be appropriately selected according to the purpose. Examples of the undifferentiated cells include, but not limited to: pluripotent stem cells, such as embryonic stem cells being undifferentiated cells and multipotent mesenchymal stem cells; unipotent stem cells, such as vascular endothelial progenitor cells having a differentiation potential; and iPS cells.

The fungi are not particularly limited and can be appropriately selected according to the purpose. Examples of the fungi include, but are not limited to, molds and yeasts. Each of these examples may be used alone, or two or more of the examples may be used in combination. Among these examples, yeasts are preferable because the cell cycle thereof is adjustable and haploid thereof can be used.

The cell cycle refers to a process in which cells (daughter cells) generated by cell division become cells (mother cells) that undergo cell division again to produce new daughter cells.

The yeasts are not particularly limited and can be appropriately selected according to the purpose. Preferred examples of the yeasts include, but are not limited to, a Bar-1 deficient yeast having an increased sensitivity to a pheromone (sex hormone) which controls the cell cycle to the G1 phase. When a Bar-1 deficient yeast is used, the abundance ratio of yeasts whose cell cycle are uncontrolled can be lowered, thereby preventing an increase of the number of specific nucleic acids of the cells accommodated in a container.

The prokaryotic cells are not particularly limited and can be appropriately selected according to the purpose. Examples of the prokaryotic cells include, but are not limited to, eubacteria and archaebacteria. Each of these examples may be used alone, or two or more of the examples may be used in combination.

Preferred examples of the cell further include dead cells. Dead cells can prevent the occurrence of cell division after sorting.

The fluorescent protein is not particularly limited and can be appropriately selected according to the purpose. Examples of the fluorescent protein include, but are not limited to, green fluorescent protein (GFP), red fluorescent protein (RFP), and yellow fluorescent protein (YFP). The fluorescent dye for staining cells is not particularly limited and can be appropriately selected according to the purpose. Examples of the fluorescent dye include, but are not limited to, Cell Tracker Orange and Cell Tracker Red.

In a case in which the fluorescent particles 201 aggregate in the suspension 200 filling the liquid chamber 11 of the droplet discharger 10, the number of the particles in the suspension can be adjusted to several particles or less by adjusting the concentration of the particles in the suspension, since the concentration and number of the particles in the suspension follow the Poisson distribution. The liquid component of the suspension is not particularly limited and can be appropriately selected according to the purpose. Examples thereof include, but are not limited to, ion-exchange water. The diameter of the droplet is not particularly limited and can be appropriately selected according to the purpose, but is preferably in a range of from 25 to 150 µm. When the diameter of the droplet is 25 µm or more, the size of the droplet is not small. Therefore, in this case, it is unlikely that the droplet contains only particles having a small diameter, and the number of types of applicable particles is unlikely to decrease. When the diameter of the droplet is 150 µm or less, the droplet has no problem as a droplet. It is not necessary to increase the hole diameter of the inkjet head through which the droplet is discharged, and discharging of the droplet is unlikely to become unstable. Further, it is preferable that the formula R>3r is satisfied, where R represents the diameter of the droplet and r represents the diameter of the particle. When the formula R>3r is satisfied, the diameter of the particle is not so larger than the diameter of the droplet. Therefore, it is unlikely that accuracy in counting the particles is lowered by an affect of the edge of the droplet.

The light irradiator 30 irradiates droplets discharged from the droplet discharger 10 with light. The light irradiator 30 is electrically coupled to the driver 20. The driver 20 inputs a synchronization signal to the light irradiator 30. As the synchronization signal is input to the light irradiator 30, the light irradiator 30 irradiates the droplet 210 with the laser beam 301, serving as illumination light, in synchronization with a discharge of the droplet 210 by the droplet discharger 10.

Preferably, the light irradiator 30 is capable of emitting light in synchronization with a discharge of the droplet 210 by the droplet discharger 10. Thus, the droplet 210 discharged from the droplet discharger 10 is more reliably irradiated with light. Here, the synchronization is achieved as the light irradiator 30 emits the laser beam 301 at the time when the discharged droplet 210 reaches a predetermined position. That is, the light irradiator 30 emits the laser beam 30 with a delay of a predetermined time period from the discharge of the droplet 210 by the droplet discharger 10.

The light irradiator 30 is not particularly limited and can be appropriately selected according to the purpose. Examples of the light irradiator 30 include, but are not limited to, a solid-state laser, a semiconductor laser, and a dye laser. Examples of solid-state lasers include YAG laser, ruby laser, and glass laser. Examples of commercially available products of YAG laser include, but are not limited to, EXPLORER ONE-532-200-KE (manufactured by Spectra-Physics KK, output wavelength is 532 nm due to SHG). Among these examples, those capable of emitting pulsed light by pulse oscillation are preferable.

The pulse width of the pulsed light is not particularly limited and can be appropriately selected according to the purpose, but is preferably 10 µs or less, more preferably 1 µs or less. The energy per unit pulse is not particularly limited and can be appropriately selected according to the purpose. Although largely depending on the optical system (e.g., whether a condenser is present or not), the energy per unit pulse is preferably 0.1 µJ or more, more preferably 1 µJ or more. However, in some cases in which the fluorescent particle undergoes photo bleaching, it is preferable that the energy per unit pulse or per unit time is limited. Also, in some cases in which light irradiation exerts an adverse affect depending on the use purpose of fluorescent particles or other luminescent particles, it is preferable that the energy per unit pulse or per unit time is limited.

The light receivers 41 and 42 each receive light emitted from the particles irradiated with light. Both the light receivers 41 and 42 are electrically coupled to the driver 20 via the light irradiator 30. The driver 20 inputs a synchronization signal to the light receivers 41 and 42. As the synchronization signal is input to the light receivers 41 and 42, the light receivers 41 and 42 receive the light beam 302a and the light beam 302b, respectively, in synchronization with light emission of the fluorescent particle 201 irradiated with the laser beam 301 emitted by the light irradiator 30.

The light receiver 41 is a light sensing device/module capable of measuring the presence or absence of the fluorescent particle 201 contained in the droplet 210. The light receiver 42 is a light sensing device/module capable of measuring the number of the fluorescent particle 201 contained in the droplet 210. The light receiver 41 and the light receiver 42 output light receiving information to the first particle measuring device 51 and the second particle measuring device 52, respectively, that are respectively electrically coupled thereto. Based on the information output from the light receivers 41 and 42, the first particle measuring device 51 measures the presence or absence of the fluorescent particle 201 contained in the droplet 210, and the second particle measuring device 52 measures the number of the fluorescent particle 201 contained in the droplet 210.

It is sufficient for the light receiver 41 to be capable of measuring only the presence or absence of the fluorescent particle 201 in cooperation with the first particle measuring device 51. Therefore, a light sensing device/unit which acquires a small amount of information may be used as the light receiver 41. Examples of such a light sensing device/unit include, but are not limited to, a photomultiplier tube (PMT), an avalanche photodiode (APD), a PIN photodiode (PIN-PD), and a low resolution CMOS (complementary metal oxide semiconductor) image sensor. These devices/units are capable of sampling at a high speed and a high frequency, and at the same time exhibits a high light use efficiency. Upon receiving weak fluorescence emitted by the fluorescent particle 201 contained in the droplet 210, the device/unit outputs an appropriate amount of information containing a required signal-noise ratio (SNR) to the first particle measuring device 51.

When an APD is used for the light receiver 41, the APD outputs the amount of light emitted by the fluorescent particle 201, being one-dimensional data, to the first particle measuring device 51. The APD can be appropriately selected considering bandwidth and sensitivity depending on the purpose and the type of illumination light to be used. Examples of the APD include, but are not limited to, APD modules such as APD410 (having a bandwidth of 100 MHz, a diameter of 1 mm, and a sensitivity of $1 \times 10^5$ V/W, manufactured by Matsusada Precision Inc.), APD130A (having a bandwidth of 50 MHz, a diameter of 1 mm, and a sensitivity of $2.5 \times 10^6$ V/W, manufactured by Thorlabs Japan Inc.), C10508-01 (having a bandwidth of 100 MHz, a diameter of 1 mm, and a sensitivity of $1.3 \times 10^7$ V/W, manufactured by Hamamatsu Photonics K.K.), and APD410A (having a bandwidth of 10 MHz, a diameter of 1 mm, and a sensitivity of $2.7 \times 10^7$ V/W, manufactured by Thorlabs Japan Inc.).

The first particle measuring device 51 may include, for example, a digitizer, a data logger, or an oscilloscope as a part thereof. The digitizer is a module (product) equipped with an analog/digital converter (ADC). Examples of the digitizer include, but are not limited to, APX-510 (16 bit, 100 MHz sampling, manufactured by AVAL DATA CORPORATION) and DIG-100M1002-PCI (10 bit, 100 MHz sampling, manufactured by CONTEC Co., Ltd.), each provided as an expansion board of a personal computer (PC). In the first particle measuring device 51, the digitizer or the like digitizes analog information output from the light receiver 41 and outputs the digitized information to an information processor that is coupled to the digitizer and constituting a part of the first particle measuring device 51. Even though the digitized acquired information on the fluorescent particle is one-dimensional data with a small amount of information, the information processor is able to measure the presence or absence of fluorescent particle based on the predetermined threshold value standard of the amount of emitted light and the time axis profile standard of the amount of emitted light. Consequently, the first particle measuring device 51 measures the presence or absence of the fluorescent particle. As the information processor that constitutes a part of the first particle measuring device 51, a personal computer (PC) or image processing software installed in PC may be used.

The measurement of the presence or absence of the fluorescent particle is a qualitative measurement that only needs to confirm light emission from the fluorescent particle. Therefore, even when the amount of acquired information is small, the measurement achieves a higher degree of accuracy, in other words, a higher rate of correct answers, compared to a measurement of the number of the fluorescent particle. As the amount of acquired information can be small, advantageously, both operations performed by the light receiver 41 for acquiring information on the light beam 302*a* and outputting the acquired information and an information processing performed by the first particle measuring device 51 for processing the acquired information are simplified, thus realizing a high-speed measurement.

Preferably, the light receiver 41 is capable of receiving the light beam 302*a* from the fluorescent particle 201 in synchronization with a discharge of the droplet 210 by the droplet discharger 10. Thus, the light receiver 41 more reliably receives the light beam 302*a* from the fluorescent particle 201 as the droplet 210 discharged from the droplet discharger 10 is irradiated with the laser beam 301 emitted from the light irradiator 30. Here, the synchronization is achieved as the light receiver 41 receives the light beam 302*a* at the time when the discharged droplet 210 reaches a predetermined position and irradiated with the laser beam 301 and the particle 201 emits the light beam 302*a*. That is, the light receiver 41 detects the light beam 302*a* with a delay of predetermined time periods each from the discharge of the droplet 210 by the droplet discharger 10 and from the irradiation of the laser beam 301 by the light irradiator 30. Such a delay adjustment may also be performed in cooperation with a function generator that outputs a synchronization signal considering each delay. The function of the function generator may be integrated with the droplet discharger 10. The above-described conditions are applied to the light receiver 42 to be described later.

When the light emitted from the particle is weaker than the laser beam 301 emitted by the light irradiator 30, it is preferable that the light receiver 41 is provided with a filter, on the light receiving surface side thereof, for attenuating light within the wavelength range of the laser beam 301. By providing the filter, the light receiver is able to receive the emitted light with little noise. Examples of the filter include, but are not limited to, a notch filter having an optical density of 6 or more that attenuates light within a specific wavelength range including the emitted light. The above-described conditions are applied to the light receiver 42 to be described later.

The light receiver 42 measures the number of the fluorescent particle 201 in cooperation with the second particle measuring device 52. This measurement is a quantitative measurement that provides a higher degree of accuracy compared to the qualitative measurement performed by the light receiver 41. Thus, it is preferable that the light receiver 42 is a light sensing device/unit which acquires a larger amount of information compared to the light receiver 41 and that the second particle measuring device 52 is capable of processing more complicated information compared to the first particle measuring device 51.

Examples of the light sensing device/unit which acquires a large amount of information include, but are not limited to, a two-dimensional light receiving sensor/module capable of acquiring image information being two-dimensional data. Specific examples of the two-dimensional light receiving sensor/module include, but are not limited to, a charge coupled device (CCD), a complementary metal oxide semiconductor (CMOS) image sensor, and a gate CCD. In recent years, the technology of scientific experimental CMOS image sensor has been developed, and the noise characteristic thereof against weak light is greatly improved. Examples of the CMOS image sensor include, but are not limited to, pco. edge 5.5 (manufactured by Tokyo Instruments, Inc.), C11440 (ORCA-Flash V2, manufactured by Hamamatsu Photonics K.K.), and C13440 (ORCA-Flash V3, manufactured by Hamamatsu Photonics K.K.). These CMOS image sensors provide a high photoelectric conversion quantum efficiency of several tens percent or more, a low reading noise of 3 electrons or less per pixel, a high-speed transmission at around 100 Hz, a high resolution of 2,000 lines or more, and 16-bit gradation. At the same time, they acquire a great amount of information with little noise and high quality as image information and output the acquired information to the second particle measuring device 52 at a high speed. There are quite a lot of types of two-dimensional light receiving sensors/modules. One having an appropriate resolution can be selected according to the purpose.

As the second particle measuring device 52, a personal computer (PC) or image processing software installed in PC may be used. A large amount of image information output from the two-dimensional light receiving sensor/module may be input to a memory of PC at a high speed by a camera link board provided as an expansion board of PC or by a universal serial bus (USB) 3.0 provided as an interface for PC. A protocol for measuring the number of fluorescent particle 201 contained in the droplet 210 based on this image information with high accuracy by PC and image processing software is not particularly limited. A highly accurate number measurement can be performed by selecting an appropriate protocol according to the purpose. A more highly accurate number measurement can be performed by combining multiple protocols.

Examples of the image processing protocol include, but are not limited to, (1) a process of obtaining radii of curvature of the shape on an emission light receiving surface and, among the obtained radii of curvature, counting the number of the centers of the circles having a radius of curvature within a predetermined range as the number of particles, (2) a process of counting the number of light emission whose outer circumferential length of the shape on the emission light receiving surface is within a predetermined range, (3) a process of counting the number of inflection points on the outer circumference of the shape on the emission light receiving surface, and (4) a process of counting the number of times the sign of the inclination of the tangent of the outer circumference of the shape on the emission light receiving surface changes as the number of particles.

In the above process (1), in a case in which the radius of curvature falls below the predetermined range, light other than the light emitted from the particle, such as refracted light and scattered light, is received. Therefore, light emission whose radius of curvature is smaller than the predetermined range is excluded. In addition, in a case in which the radius of curvature exceeds the predetermined range, when the particle is present in the vicinity of the outer periphery of the droplet, the light emitted from the particle upon irradiation with light is reflected on the inner spherical surface of the droplet, and therefore the outer edge of the droplet appears to emit light. Such a light emission is determined not to be light emitted from the particle, and excluded. Thus, it is possible that the number of the centers of the circles whose radius of curvature calculated based on the information on the shape on the emission light receiving surface is within the predetermined range is counted as the number of particles.

The above process (2) is a process in which the radius of curvature in the process (1) is replaced with the outer circumferential length of the shape on the emission light receiving surface.

In the above process (3), for example, the number of inflection points becomes two when two light emissions overlap and the number of inflection points becomes three when three light emissions overlap, so that the inflection point can be counted as the number of particles.

In the above process (4), for example, the sign of the inclination of the tangent changes twice when two light emissions overlap and the sign of the inclination of the tangent changes three times when three light emissions overlap, so that the number of times the sign of the inclination of the tangent changes can be counted as the number of particles.

Of these, the process (1) is preferable. Specifically, it is preferable that the particle counter performs a second counting process that calculates radii of curvature based on information on the shape on the emission light receiving surface and counts the number of the centers of the circles whose above-calculated radius of curvature is within the predetermined range as the number of particles. When the second counting process is the process (1), it is easy to count the number of multiple particles, improving the accuracy in counting particles.

In the above processes, the number counting is performed by controlling PC that includes a central processing unit (CPU) for controlling each related operation, a read only memory (ROM), a random access memory (RAM), and a main memory according to an image processing software. The image processing software may be general-purpose image processing software. Examples of general-purpose image processing software include, but are not limited to, ImageJ (open source manufactured by the National Institutes of Health). The image processing software is not limited to general-purpose image processing software, and image processing software created by a programming language such as C #, C++, and Phyton may also be used. In addition, a graphics processing unit (GPU) may also be used. In the case of using image processing software created by a programming language, control of the droplet discharger 10 can be performed by the same programming language. Therefore, a cooperative operation between the droplet discharge control and the number measurement of fluorescent particles becomes easy. The same applies to the case of measuring the presence or absence of fluorescent particles by a cooperative operation between the light receiver 41 and the first particle measuring device 51.

Referring to FIG. 1, the light receiver 42 used in combination with the second particle measuring device 52 for measuring the number is not limited to a two-dimensional light receiving sensor/module, and any other means which is capable of handling a large amount of information may be used, so that the measurement of the number of fluorescent particles can be carried out. In a case in which laser beam emitted from the light irradiator 30 has a pulse time longer than required, a high-band APD and a high-band digitizer are used for the light receiver 42, and a minute slit or a minute pinhole is provided in front of the APD, information corresponding to positional change of the discharged droplet 210 may be acquired as temporal change information of the voltage output from the APD.

For example, an APD module C5658 (having a bandwidth of 1 GHz, a diameter 0.5 mm, and a sensitivity $2.5 \times 10^5$ V/W, manufactured by Hamamatsu Photonics K.K.) may be used as the APD, a slit may be provided at an imaging position on an image plane of an imaging optical system being a part of the light receiver 42 and in front of the APD, and the width of the slit may be set so that the upper and lower widths become 10 μm. In a case in which the magnification of the imaging optical system is 5 times, the width of the slit corresponds to a width of 2 μm on an object plane of the droplet 210. In this case, a positional change of the droplet 210 having a diameter of about 80 μm being discharged downward at a velocity of about 1 m/s (=1 μm/μs) over a period of 80 μs may be acquired as spatial information highly correlated with shape information of 40 droplets spatially divided in the discharge direction with a resolution of about 2 μm. By analyzing the profile of the spatial information, the number of fluorescent particles 201 can be measured. By providing a pinhole rather than the slit, installing multiple APDs in a direction perpendicular to the discharge direction, and acquiring spatial information in a direction perpendicular to the discharge direction, the accuracy is further improved.

Figure 2:
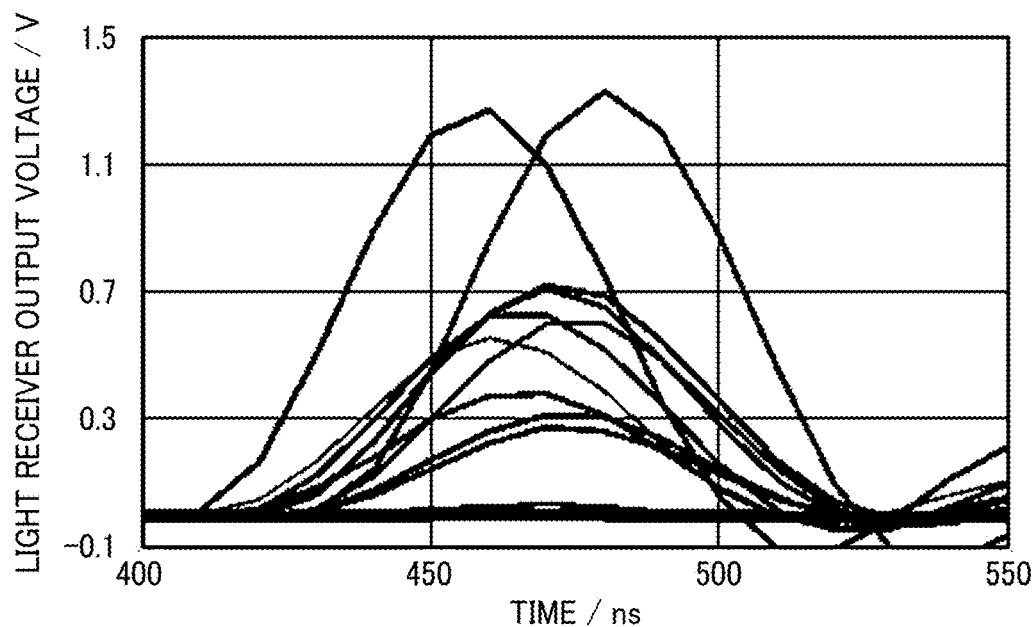
FIG. 2 is a graph illustrating data output from a light receiver 41 of the particle counting apparatus illustrated in FIG. 1.

FIG. 2 is a graph illustrating data output from the light receiver 41 of the particle counting apparatus 100A according to the first embodiment. Specifically, FIG. 2 illustrates data output from the digitizer to the information processor when 50 droplets 210 are discharged from the nozzle 12 of the droplet discharger 10 under the conditions that SPHERO FLUORESCENT NILE RED PARTICLES (having a diameter of 2.5 to 4.5 μm, manufactured by Bay bioscience Co., Ltd.) are used as the fluorescent particles 201, the concentration of the fluorescent particles 201 in the particle suspension 200 is adjusted to about 0.2 particles/droplet in average, EXPLORER ONE-532-200-KE capable of emitting pulsed light is used as a part of the light irradiator 30, the laser output is set to about 200 μJ per pulse, the light receiver 41 manufactured by Thorlabs Japan Inc. is used, and a digitizer DIG-100M1002-PCI (100 MHz sampling, impedance 50Ω setting) and a desktop PC are used as the first particle measuring device 51. In FIG. 2, the horizontal axis is a time axis representing relative values based on the trigger applied to the droplet discharger 10, and the vertical axis represents voltage values of an electric signal that is information output from the light receiver 41 to the digitizer.

As illustrated in FIG. 2, 10 polygonal lines corresponding to 10 droplets out of 50 discharged droplets are output as upwardly convex polygonal lines, and 40 polygonal lines corresponding to the remaining 40 droplets are output as polygonal lines densely overlapped with each other in the vicinity of the horizontal axis representing the voltage value of 0 V. As a result of comparing these data with the number of fluorescent particles measured with high accuracy using the aforementioned C11440 as the light receiver 42 together with the second particle measuring device 52, it is confirmed that 10 droplets represented by upwardly convex polygonal lines contain fluorescent particles and 40 droplets represented by polygonal lines in the vicinity of the horizontal axis representing the voltage value of 0 V contain no fluorescent particle. Accordingly, it is confirmed that the combination of the light receiver 41 and the first particle measuring device 51 is able to measure the presence or absence of the fluorescent particle 201 contained in the droplet 210 with high accuracy.

FIG. 2 indicates that the peak voltage for each of the 10 droplets 210 containing the fluorescent particle 201 ranges approximately from 0.3 to 1.3 V. The three major reasons for this are considered that: (1) there is a possibility that the number of fluorescent particles contained in the droplet varies from 1 to 3; (2) the irradiation intensity of the laser beam, serving as illumination light, emitted by the light irradiator 30 to the fluorescent particles 201 contained in the droplet 210 varies greatly depending on the position of the fluorescent particles 201 in the droplet 210; and (3) the light use efficiency for the light beam 302a emitted by the fluorescent particles and received by the light receiver 41 varies greatly. When the concentration of the fluorescent particles 201 in the particle suspension 200 is about 0.2 particles/droplet in average, among the droplets in which the fluorescent particle 201 is present, it is estimated based on the Poisson distribution that a probability that the droplet contains one to three fluorescent particles is 99.97% and a probability that the droplet contains two to three fluorescent particles is 9.6%. Therefore, it is not stochastically rare that one droplet or two droplets out of ten droplets containing the fluorescent particle each contain two to three fluorescent particles. In FIG. 2, there are two droplets having an output voltage exceeding 1.1 V. It is highly likely that each of these droplets contains two or more fluorescent particles.

Further, in FIG. 2, among the ten droplets containing the fluorescent particle 201, it is highly likely that eight droplets each contain one fluorescent particle. The output voltage thereof varies more than twice, i.e., in a range of about 0.3 to 0.7 V. It is considered that this variation depends on the above-described variations of the light irradiator 30 and the light receiver 41 exerted to the fluorescent particles 201.

In actual, however, the output voltage from the light receiver 41 for the eight droplets which are likely to contain one fluorescent particle has a variation, that is, a more-than-twice variation ranging about 0.3 to 0.7 V. Thus, it is difficult to quantitatively measure the number of fluorescent particles by discriminating the presence of one particle from that of two particles with high accuracy. On the other hand, it can be confirmed that when the droplet 210 contains the fluorescent particle 201, the peak output voltage thereof is always about 0.3 V or more; and when the droplet 210 contains no fluorescent particle 201, no clear peak exists and the output voltage thereof is 0.1 V or less at the maximum. Therefore, by simply setting the maximum voltage as a threshold, for example, setting the threshold to 0.2 V, and judging the threshold by the first particle measuring device 51, the presence or absence of the fluorescent particle 201 can be measured with high accuracy. This is because this measurement is a simple measurement for measuring the presence or absence of light emission.

The measurement of the presence or absence of the fluorescent particle 201 by the light receiver 41 and the first particle measuring device 51 is not limited to be performed based on a judgment on the output voltage threshold by the digitizer whose output voltage is described in FIG. 2, and may be more simply performed employing a logic judgment by transistor-transistor logic (TTL), low voltage transistor-transistor logic (LVTTL), CMOS, etc., in combination with an amplifier etc. In addition, when erroneous measurement occurs due to noise or the like and the accuracy decreases with only the judgment on the output voltage threshold, an integration circuit for the time axis window or the time axis gate may be provided to provide a threshold for the integrated amount and a logic judgment may be made by TTL, LVTTL, CMOS, etc. Furthermore, a normal waveform profile region or an abnormal waveform profile region may be provided in the set time axis window region, and the presence or absence of fluorescent particles may be determined by measuring whether it is inside or outside the region.

The measurement of the presence or absence of the fluorescent particle based on the output voltage presented in FIG. 2 can be performed at a high speed of 10 MHz at the maximum, since the width of the upward convex peak corresponding to the presence or absence of the fluorescent particle is about 100 ns. In FIG. 2, since an APD with a bandwidth of 10 MHz is used, the peak width is about 100 ns, which is wider than that of the pulsed light emitted by the light irradiator 30 that is about 15 ns. By using an APD with a high band spec, a higher-speed measurement can be performed. On the other hand, it is generally difficult for the droplet discharger 10 to discharge droplets at a high speed above its resonance frequency, and the speed is limited by the mechanical resonance frequency. In the embodiment illustrated in FIG. 2, the resonance frequency is 1 MHz or less, since the droplet 210 containing the fluorescent particles 201 having a size of several μm or more is desirably discharged and the liquid chamber 11 and the nozzle 12 are larger in size than a typical inkjet head for small droplets used for printing on paper. This is sufficiently fast for measuring the droplet 210 discharged from the droplet discharger 10.

When the drive frequency of the droplet discharger 10 is about 100 Hz, a low-resolution CMOS image sensor that is a two-dimensional light receiving sensor/module may be used as the light receiver 41 that receives information on the amount of emitted light being one-dimensional information. The light receiving operation of the CMOS image sensor is a shutter operation with a resolution of 1 ms, and therefore the CMOS image sensor can be driven at a frequency around 1 kHz. In the case of high resolution, however, it takes time to output a large amount of image information and a high-speed operation cannot be performed.

In place of the low-resolution CMOS image sensor, a high-resolution CMOS image sensor may transfer image information while reducing the number of pixels by binning or cropping, so that the minimum number of pixels for detecting the amount of light is transferred to the first particle measuring device 51, the first particle measuring device 51 calculates emitted light amount information based on image information, and the presence or absence of the fluorescent particle in the droplet is judged or measured based on the emitted light amount information.

When the low-resolution CMOS image sensor is used, the presence or absence of fluorescent particle in the droplet can be measured with high accuracy and at a high speed based on a threshold set based on the amount of emitted light from multiple pixels while using information on the multiple pixels as two-dimensional information, without performing an image processing focusing on the shape that requires time for output. This measurement is achieved by providing the second particle measuring device with a determination unit that determines the presence of the fluorescent particle when a certain number of multiple pixels with a certain level of luminance threshold value are confirmed. Here, the luminance is not a light quantity proportional to the total number of photons incident on the CMOS image sensor, but is a light quantity per unit area proportional to the incident number of photons per pixel expressed by a gradation of 16 bits. The light quantity relates only to a part of the multiple pixels. The operation is a special simplified calculation of light quantity that is completely different from typical image processing based on shape, and is equivalent to restricting the sensor region of a sensor which acquires one-dimensional data, such as APD, in advance or afterwards. It is possible to reduce noise from pixels in unnecessary regions, thus improving accuracy.

Figure 3A:
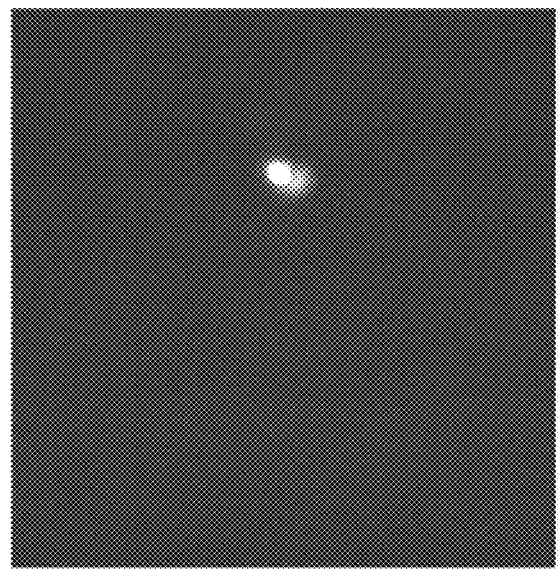
FIG. 3A is an illustration of data output from a light receiver 42 of the particle counting apparatus illustrated in FIG. 1.
Figure 3B:
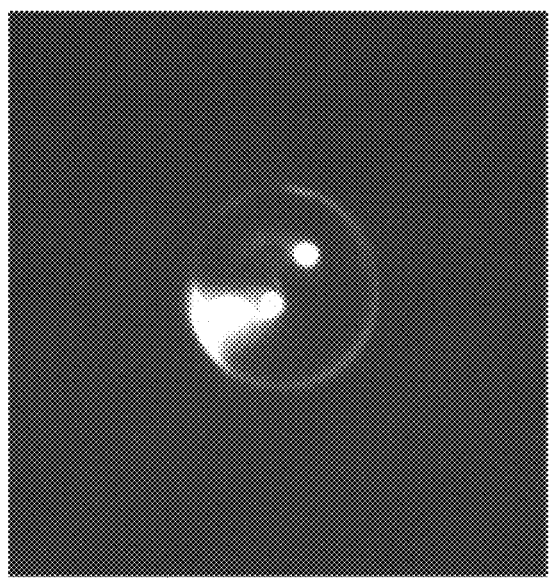
FIG. 3B is another illustration of data output from a light receiver 42 of the particle counting apparatus illustrated in FIG. 1.

FIGS. 3A and 3B are illustrations of data output from the light receiver 42 of the particle counting apparatus 100A according to the first embodiment. Specifically, FIGS. 3A and 3B illustrate images of fluorescent particles contained in a droplet with complicated image information, received by a two-dimensional light receiving sensor/module, under the conditions that SPHERO FLUORESCENT NILE RED PARTICLES (having a diameter of 10 to 14 μm, manufactured by Bay bioscience Co., Ltd.) are used as the fluorescent particles, the droplet 210 is discharged from the nozzle 12 of the droplet discharger 10, EXPLORER ONE-532-200-KE capable of emitting pulsed light having a width of about 15 ns is used as a part of the light irradiator 30, the laser output is set to about 200 μJ per pulse, pco. edge 5.5 (manufactured by Tokyo Instruments, Inc.) is used as the two-dimensional light receiving sensor/module, and a microscope objective lens M-PLAN APO 5× (manufactured by Mitutoyo Corporation) and a compliant imaging lens unit (manufactured by Mitutoyo Corporation) are used as an imaging system.

FIG. 3A is an illustration of data output from the light receiver 42 illustrated in FIG. 1. FIG. 3A is an image of a spherical or ellipsoidal droplet having a depth in a direction perpendicular to the surface of the paper on which FIG. 3A is drawn, containing two fluorescent particles. The image is received from a light receiving direction in which one of the particles is present on the surface side of the paper and the other particle is present on the back side of the paper. Since the luminance value of light emitted from the particle present on the back side of the paper attenuates due to refraction and/or scattering caused while the light passes through the droplet, the amount of emitted light may vary depending on the position of the particles in the droplet relative to the light receiver.

FIG. 3B is another illustration of data output from the light receiver 42 illustrated in FIG. 1. FIG. 3B is an image of a spherical or ellipsoidal droplet having a depth in a direction perpendicular to the surface of the paper on which FIG. 3B is drawn, containing three fluorescent particles. The image is received from a light receiving direction in which one of the particles is present in the vicinity of the outer periphery of the droplet. As illustrated in FIG. 3B, the light emitted from the fluorescent particle present in the vicinity of the outer periphery of the droplet is reflected on the inner spherical surface of the droplet in some cases.

In the both cases illustrated in FIGS. 3A and 3B, it is difficult to measure the number of the fluorescent particles based on the threshold of the amount of light emitted from the droplet, since the light emitted from the fluorescent particles is reflected on the inner spherical surface of the droplet. In such a case, a highly accurate measurement is optimally performed by an image processing focusing on shape, such as the above-described protocol.

However, such a measurement of the number of fluorescent particles based on an image processing focused on shape is difficult to perform at a high speed, even with high accuracy, because of processing a large amount of information. In the cases illustrated in FIGS. 3A and 3B in which the pco. edge 5.5 is used as the light receiver 42, merely outputting the large amount of information from the light receiver 42 to the second particle measuring device 52 is performed at about 100 Hz, and it is difficult for the particle measuring device to perform an operation including an image processing at about 100 Hz.

When a field programmable gate array (FPGA) is integrated as a two-dimensional light receiving sensor/module, an image processing focusing on shape can be performed before a large amount of information is output to the outside. Therefore, commercially-available products that perform a complicated image processing at 30 Hz, which is the video rate, or a simple image processing at a higher speed of 60 to 100 Hz are difficult to use as the two-dimensional light receiving sensor/module according to the purpose of the present embodiment, since they are noisy compared with scientific CMOS, have a low resolution specification at HDTV level with small information and high resolution, or have a low gradation of about 8 bits.

Accordingly, the particle counting apparatus 100A according to an embodiment illustrated in FIG. 1 includes two different particle measuring devices, i.e., the first particle measuring device 51 that measures the presence or absence of the fluorescent particle 201 contained in the droplet 210 and the second particle measuring device 52 that measures the number of the particles contained in the droplet 210, to improve the counting accuracy and measurement speed.

This operation is described below in a more detailed manner. When the concentration of the fluorescent particles is about 0.2 particles/droplet in average, it is estimated based on the Poisson distribution that the probability that the fluorescent particle is present in the droplet is 0.181, which is close to 0.2 but smaller than this. That is, the fluorescent particle is probably present in one droplet out of about 5.52 droplets in average (1/0.181≈5.52). Therefore, 4.42 droplets in average (excluding the one droplet) contain no fluorescent particle, and it is unnecessary for the second particle measuring device 52 to measure the number of the fluorescent particle contained therein. Therefore, in a case in which the presence or absence of fluorescent particle is measured by the first particle measuring device 51 and the number of fluorescent particle is measured by the second particle measuring device 52 only when the presence of the fluorescent particle is measured, the measurement speed can be improved 5.52 times in average compared to a case in which the presence or absence of fluorescent particle and the number of fluorescent particle are measured by a single measuring device equivalent to the second particle measuring device 52. This is because, in the case of measuring the presence or absence of fluorescent particle and the number of fluorescent particle only by a single measuring device equivalent to the second particle measuring device 52, the processing speed is low, as described above, since a large amount of image data is transferred and processed. For example, the possible measuring speed of pco. edge 5.5 having a high resolution is about 10 Hz, including control speed. On the other hand, according to an embodiment, the first particle measuring device 51 can perform a high speed measurement at a frequency of 55 Hz, corresponding to the droplet discharge frequency of 55 Hz that is 5.52 times the above, and the second particle measuring device 52 can successively perform a number measurement using image processing, thus achieving a measurement with high accuracy.

When the concentration of the fluorescent particles is about 0.02 particles/droplet in average, it is estimated based on the Poisson distribution that the probability that the fluorescent particle is present in the droplet is 0.0198, which is close to 0.02 but smaller than this. That is, the fluorescent particle is probably present in one droplet out of about 50.5 droplets in average (1/0.0198≈50.5). Therefore, 49.5 droplets in average (excluding the one droplet) contain no fluorescent particle, and it is unnecessary for the second particle measuring device 52 to measure the number of the fluorescent particle contained therein. In the same manner as in the above-described case in which the concentration of the fluorescent particle is about 0.2 particles/droplet, the first particle measuring device 51 can perform a very high speed measurement at a frequency of 505 Hz, corresponding to the droplet discharge frequency of 505 Hz that is 50.5 times the above, and the second particle measuring device 52 can successively perform a number measurement using image processing, thus achieving a measurement with high accuracy.

When the concentration of the fluorescent particles is large, i.e., about 1 particle/droplet in average, it is estimated based on the Poisson distribution that the probability that the fluorescent particle is present in the droplet is 0.632, which is not 1 and very smaller than this. That is, the fluorescent particle is probably present in one droplet out of about 1.58 droplets in average (1/0.632≈1.58). Therefore, 0.58 droplets in average (excluding the one droplet) contain no fluorescent particle, and it is unnecessary for the second particle measuring device 52 to measure the number of the fluorescent particle contained therein. In the same manner as in the above-described case in which the concentration of the fluorescent particle is about 0.2 particles/droplet, the first particle measuring device 51 can perform a high speed measurement at a frequency of about 16 Hz, corresponding to the droplet discharge frequency of about 16 Hz that is 1.58 times the above, and the second particle measuring device 52 can successively perform a number measurement using image processing, thus achieving a measurement with high accuracy.

Even in a case in which the concentration of fluorescent particles is much higher, it is estimated based on the Poisson distribution that the probability that the fluorescent particle is present in the droplet is 0.907 at most, when the concentration is about 2.4 particles/droplet at most in average. When combining the first particle measuring device 51 and the second particle measuring device 52 according to an embodiment, in the same manner as in the above-described case in which the concentration of the fluorescent particle is about 0.2 particles/droplet, a measurement can be performed at a 10% or more higher speed. It is more effective than the case of measuring the presence or absence and the number of fluorescent particles using the second particle measuring device alone at a wide range of fluorescent particle concentration.

Figure 4:
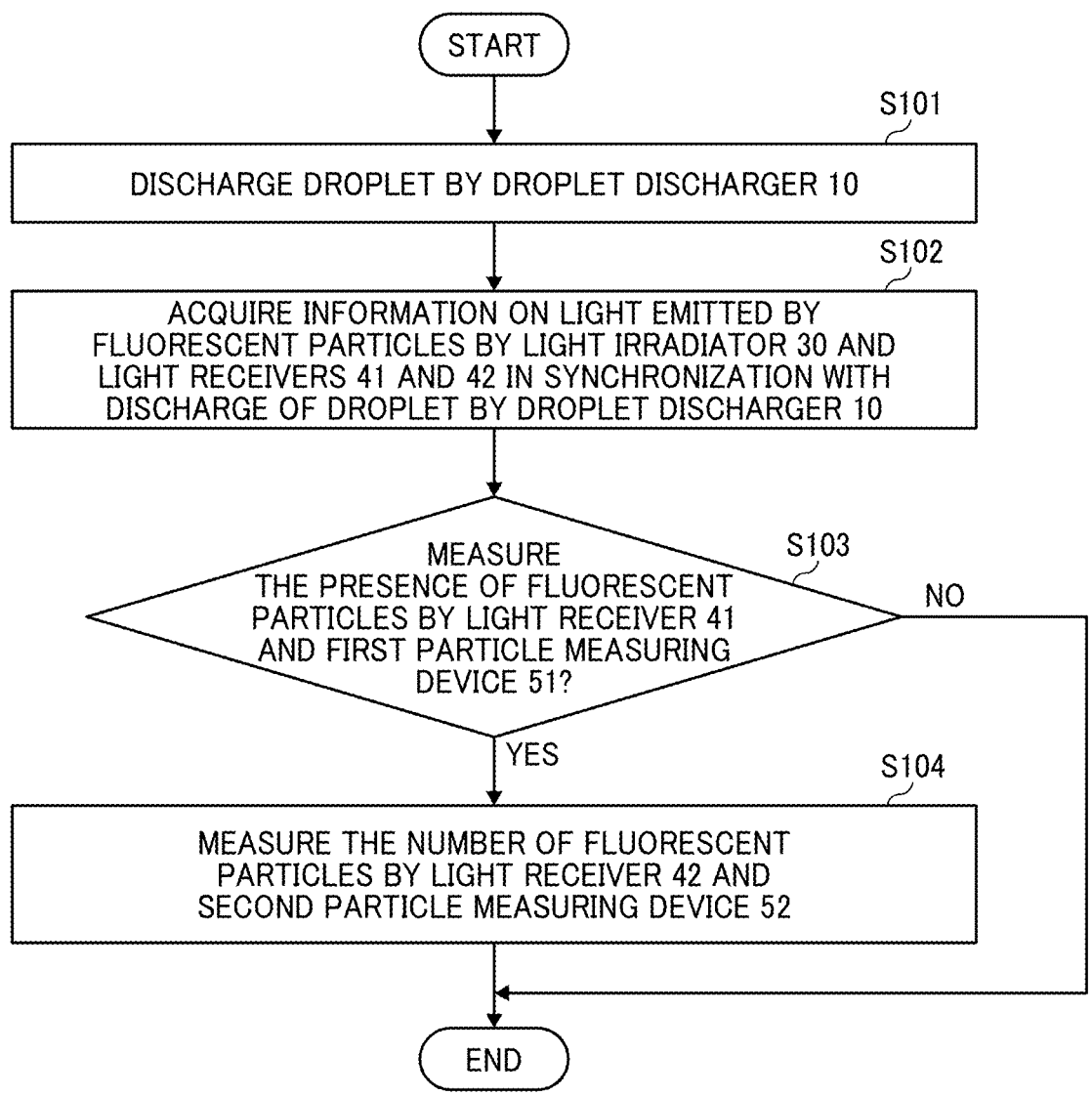
FIG. 4 is a flowchart of an operation of the particle counting apparatus according to the first embodiment.

FIG. 4 is a flowchart of an operation of the particle counting apparatus 100A including the first particle measuring device 51 and the second particle measuring device 52, illustrated in FIG. 1, that can improve the counting accuracy and measurement speed. As illustrated in FIG. 4, in S101, the droplet discharger 10 to which a drive voltage is applied from the driver 20 discharges the droplet 210 containing the fluorescent particle 201 in the discharge direction 303 illustrated in FIG. 1 from the nozzle 12. The driver 20 applies a drive voltage to the droplet discharger 10 and outputs a synchronization signal to the light irradiator 30 and the two light receivers 41 and 42. The particle counting apparatus 100A thereafter transits the processing to S102.

In S102, the droplet discharger 10, to which the synchronization signal is input from the driver 20, irradiates the droplet 210 with the laser beam 301 in synchronization with a discharge of the droplet 210. In addition, the light receiver 41 and 42, to which the synchronization signal is input, receive the light beam 302a and the light beam 302b, respectively, emitted by the fluorescent particles 201 upon irradiation with the laser beam 301 emitted from the light irradiator 30. As a result, the light receivers 41 and 42 acquire information on light emitted by the fluorescent particles 201. The particle counting apparatus 100A thereafter transits the processing to S103.

In S103, the first particle measuring device 51, to which information on the light beam 302a emitted by the fluorescent particle 201 is output from the light receiver 41, measures the presence or absence of the fluorescent particle 201 contained in the droplet 210 and determines the presence or absence of the fluorescent particle 201. When it is determined that the fluorescent particle 201 is present, the particle counting apparatus 100A transits the processing to S104. When it is determined that the fluorescent particle 201 is absent, the particle counting apparatus 100A terminates this processing.

In S104, the second particle measuring device 52, to which information on the light beam 302b emitted by the fluorescent particle 201 is output from the light receiver 42, measures the number of the fluorescent particles 201 contained in the droplet 210. The particle counting apparatus 100A thereafter terminates the processing. Through the series of operations S101 to S104, the particle counting apparatus 100A can improve the counting accuracy and measurement speed.

Second Embodiment

The particle counting apparatus according to the second embodiment further includes, in addition to the components of the particle counting apparatus according to the first embodiment: a particle counter controller configured to control the second particle measuring device to measure the number of the luminescent particle contained in the droplet, based on information from the first particle measuring device that the luminescent particle is present in the droplet; and a droplet discharger controller configured to control the droplet discharger, based on information from the second particle measuring device on the number of the luminescent particle contained in the droplet, or based on information from the first particle measuring device that the luminescent particle is absent in the droplet without using any information from the second particle measuring device.

The particle counting method according to the second embodiment further includes, in addition to the processes in the particle counting apparatus according to the first embodiment, the processes of: controlling the counting process such that the number of the luminescent particle contained in the droplet is measured in the secondly measuring process based on information from the firstly measuring process that the luminescent particle is present in the droplet; and controlling the discharging process, based on information from the secondly measuring process on the number of the luminescent particle contained in the droplet, or based on information from the firstly measuring process that the luminescent particle is absent in the droplet without using any information from the secondly measuring process.

The process of controlling the counting process is preferably performed by the particle counter controller, and the process of controlling the discharging process is preferably performed by the droplet discharger controller.

It is preferable that the process of controlling the discharging process is a process that accumulates the number of luminescent particle based on the information from the secondly measuring process on the number of the luminescent particle contained in the droplet.

Figure 5:
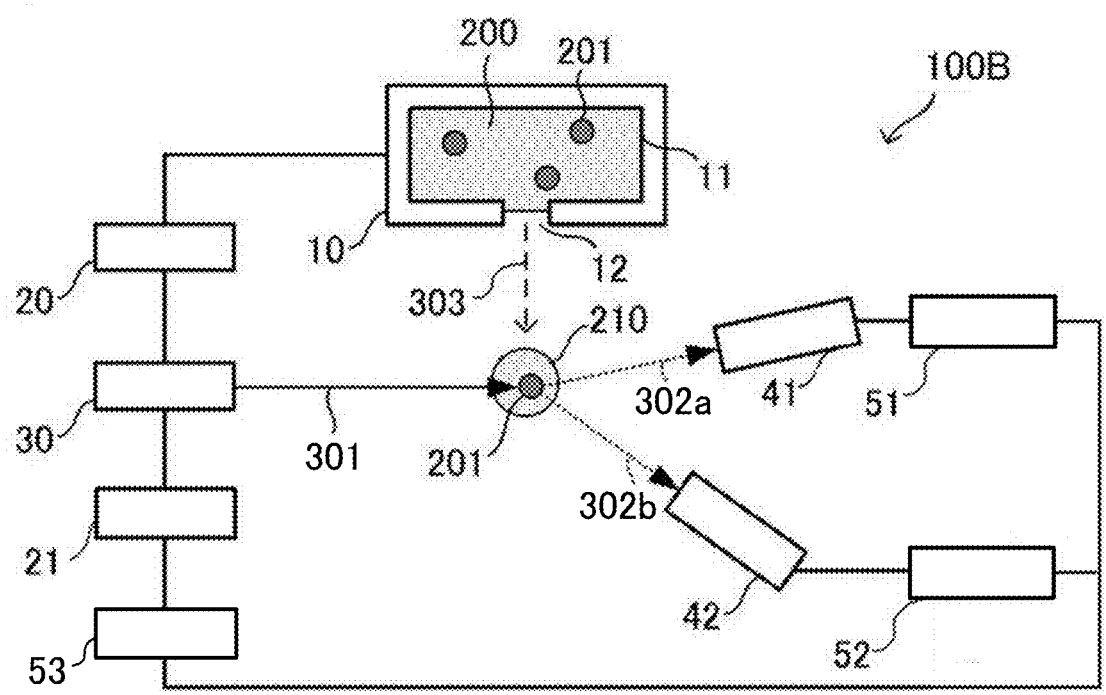
FIG. 5 is a schematic diagram of a particle counting apparatus according to a second embodiment.

FIG. 5 is a schematic diagram of a particle counting apparatus according to a second embodiment. The particle counting apparatus according to the second embodiment illustrated in FIG. 5 has a similar configuration to the particle counting apparatus according to the first embodiment illustrated in FIG. 1, but is different in that a particle counter controller and a droplet discharger controller is further provided. Referring to FIG. 5, a particle counting apparatus 100B includes a droplet discharger 10 equipped with a liquid chamber 11 and a nozzle 12, a driver 20, a light irradiator 30, light receivers 41 and 42, a first particle measuring device 51, a second particle measuring device 52, a particle counter controller 53, and a droplet discharger controller 21. A particle suspension 200 contains fluorescent particles 201. A droplet 210 is discharged from the nozzle 12 of the droplet discharger 10 in a discharge direction 303. Laser beam 301 is emitted by the light irradiator 30. Light beam 302a is received by the light receiver 41. Light beam 302b is received by the light receiver 42.

Hereinafter, with regard to the second embodiment illustrated in FIG. 5, a description for the same configuration as that in FIG. 1 will be partially omitted. As illustrated in FIG. 5, the droplet discharger 10 stores the particle suspension 200 in which the fluorescent particles 201 are suspended in the liquid chamber 11. As a piezoelectric element disposed in the liquid chamber 11 deforms, the droplet 210 in a spherical, ellipsoidal, or slightly-deformed spherical or ellipsoidal shape and containing the fluorescent particle 201 is discharged in the discharge direction 303.

The light irradiator 30 irradiates droplets discharged from the droplet discharger 10 with light. The light irradiator 30 is electrically coupled to the driver 20. The driver 20 inputs a synchronization signal to the light irradiator 30. As the synchronization signal is input to the light irradiator 30, the light irradiator 30 irradiates the droplet 210 with the laser beam 301, serving as illumination light, in synchronization with a discharge of the droplet 210 by the droplet discharger 10.

Both the light receivers 41 and 42 are electrically coupled to the driver 20 via the light irradiator 30. The driver 20 inputs a synchronization signal to the light receivers 41 and 42. As the synchronization signal is input to the light receivers 41 and 42, the light receivers 41 and 42 receive the light beam 302a and the light beam 302b, respectively, in synchronization with light emission of the fluorescent particle 201 irradiated with the laser beam 301 emitted by the light irradiator 30.

The light receiver 41 is a light sensing device/module capable of measuring the presence or absence of the fluorescent particle 201 contained in the droplet 210. The light receiver 42 is a light sensing device/module capable of measuring the number of the fluorescent particle 201 contained in the droplet 210. The light receiver 41 and the light receiver 42 output light receiving information to the first particle measuring device 51 and the second particle measuring device 52, respectively, that are respectively electrically coupled thereto. Based on the information output from the light receivers 41 and 42, the first particle measuring device 51 measures the presence or absence of the fluorescent particle 201 contained in the droplet 210, and the second particle measuring device 52 measures the number of the fluorescent particle 201 contained in the droplet 210.

The light receiver 42 measures the number of the fluorescent particle 201 in cooperation with the second particle measuring device 52. This measurement is a quantitative measurement that provides a higher degree of accuracy compared to the qualitative measurement performed by the light receiver 41. Thus, the light receiver 42 is a light sensing device/unit which acquires a larger amount of information compared to the light receiver 41 and the second particle measuring device 52 is capable of processing more complicated information compared to the first particle measuring device 51.

As the second particle measuring device 52, a personal computer (PC) or image processing software installed in PC may be used. A large amount of image information output from the two-dimensional light receiving sensor/module may be input to a memory of PC at a high speed via an input-output interface for PC.

When the first particle measuring device 51 outputs information that the fluorescent particle 201 is present in the droplet 210, the particle counter controller 53 controls the second particle measuring device 52 to measure the number of the fluorescent particle 201 in the same manner as in the first embodiment illustrated in FIGS. 1 and 4. When the first particle measuring device 51 outputs information that the fluorescent particle 201 is absent in the droplet 210, the droplet discharger controller 21 outputs signals at appropriate timing to cause the light irradiator 30 to emit the laser beam 301 again, the droplet discharger 10 to discharge a droplet again, the light receivers 41 and 42 to receive light, and the first particle measuring device 51 and the second particle measuring device 52 to perform the particle measurement again. As a result, the second discharge of the droplet 210 and the accompanied measurement of the fluorescent particle 201 in the droplet 210 are performed.

In measuring the fluorescent particle 201 contained in the droplet 210 discharged in the second discharge, when the first particle measuring device 51 outputs information that the fluorescent particle 201 is present in the droplet 210, the particle counter controller 53 controls the second particle measuring device 52 to measure the number of the fluorescent particle 201, in the same manner as in the first discharge, and thereafter terminates the measurement of the particles and the discharge of droplets. When the first particle measuring device 51 outputs information that the fluorescent particle 201 is absent in the droplet 210, the droplet discharger controller 21 outputs signals at appropriate timing to cause the light irradiator 30 to emit the laser beam 301 again, the droplet discharger 10 to discharge a droplet again, the light receivers 41 and 42 to receive light, and the first particle measuring device 51 and the second particle measuring device 52 to perform the particle measurement again, in the same manner as in the first discharge. As a result, the third discharge of the droplet 210 and the accompanied measurement of the fluorescent particle 201 in the droplet 210 are performed. Until the first particle measuring device 51 measures the presence of the fluorescent particle in the droplet 210, the droplet discharger controller 21 controls the droplet discharger 10 and the related modules so as to repeat the same operations. Repetition of the operations is terminated when the first particle measuring device 51 measures the presence of the fluorescent particle in the droplet 210 and the particle counting apparatus 100B acquires information on the number of the fluorescent particle measured by the second particle measuring device 52.

When one or more fluorescent particles are required at a predetermined droplet discharge position, by these operations, the particle counting apparatus is capable of measuring the number of fluorescent particle 201 in the droplet 210 discharged from the droplet discharger 10 with high accuracy and at a high speed. Even when two or more fluorescent particles are required at a predetermined droplet discharge position, the particle counting apparatus is capable of measuring the number of particle with high accuracy and at a high speed by, in addition to the above-described operations, continuing the droplet discharge control of the droplet discharger 10 by the droplet discharger controller 21 and the measurement by the first particle measuring device 51 and the second particle measurement means 52, until it is determined that particles are accumulated to a predetermined number by adding information on the number measured by the second particle measuring device 52.

The droplet discharger controller 21 is not limited to output a signal for controlling the droplet discharger 10 via the light irradiator 30 as illustrated in FIG. 5, and may be directly or indirectly cooperated with a function generator to output a synchronization signal considering each delay via the function generator. The function of the function generator may be integrated with the droplet discharger 10 or the droplet discharger controller 21. In addition, the droplet discharger controller 21 is not limited to acquire information only from the first particle measuring device 51 and the second particle measuring device 52, and may acquire information from other multiple constitutional elements, to control the droplet discharger 10.

As the particle counter controller 53, similar to the first particle measuring device 51, a personal computer (PC) and control software installed therein, a programmable logic controller (PLC), or an instrument dedicated for control called a sequencer and a sequence program installed therein may be used.

As the droplet discharger controller 21, similar to the first particle measuring device 51 or the particle counter controller 53, a personal computer (PC) and control software installed therein, a programmable logic controller (PLC), or an instrument dedicated for control called a sequencer and a sequence program installed therein may be used.

Figure 6:
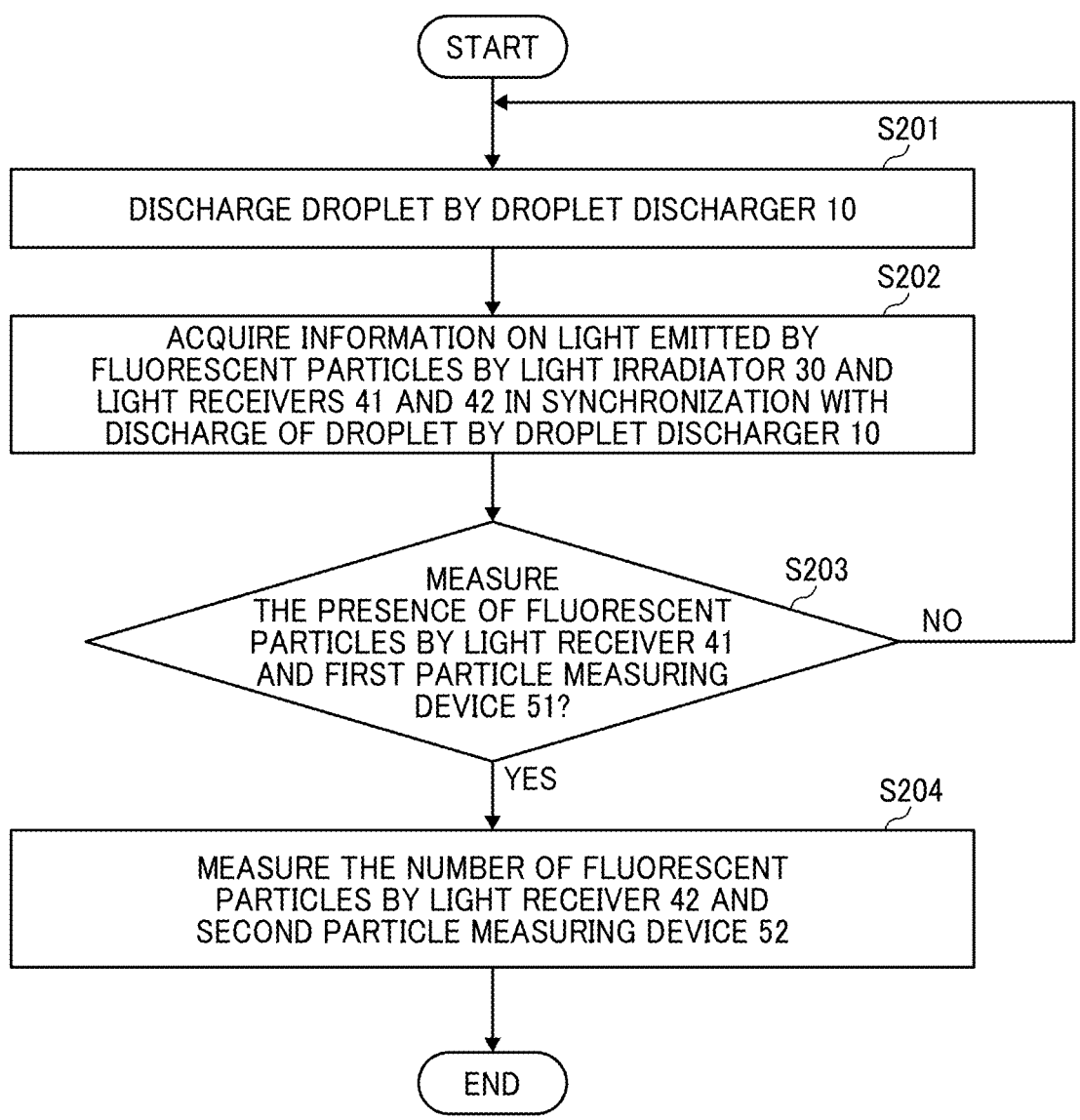
FIG. 6 is a flowchart of an operation of the particle counting apparatus according to the second embodiment.

FIG. 6 is a flowchart of an operation of the particle counting apparatus according to the second embodiment. Specifically, FIG. 6 illustrates an operation procedure of the particle counting apparatus 100B according to the second embodiment including the particle counter controller 53 and the droplet discharger controller 21, illustrated in FIG. 5, that can improve the counting accuracy and measurement speed. As illustrated in FIG. 6, in S201, the droplet discharger 10 to which a drive voltage is applied from the driver 20 discharges the droplet 210 containing the fluorescent particle 201 in the discharge direction 303 illustrated in FIG. 5 from the nozzle 12. The driver 20 applies a drive voltage to the droplet discharger 10 and outputs a synchronization signal to the light irradiator 30 and the two light receivers 41 and 42. The particle counting apparatus 100B thereafter transits the processing to S202.

In S202, the droplet discharger 10, to which the synchronization signal is input from the driver 20, irradiates the droplet 210 with the laser beam 301 in synchronization with a discharge of the droplet 210. As the synchronization signal is input to the light receivers 41 and 42, the light receivers 41 and 42 receive the light beam 302a and the light beam 302b, respectively, in synchronization with light emission of the fluorescent particle 201 irradiated with the laser beam 301 emitted by the light irradiator 30. As a result, the light receivers 41 and 42 acquire information on light emitted by the fluorescent particles 201. The particle counting apparatus 100B thereafter transits the processing to S203.

In S203, the first particle measuring device 51, to which information on the light beam 302a emitted by the fluorescent particle 201 is output from the light receiver 41, measures the presence or absence of the fluorescent particle 201 contained in the droplet 210 and determines the presence or absence of the fluorescent particle 201. When it is determined that the fluorescent particle 201 is present, the particle counting apparatus 100B transits the processing to S204. When it is determined that the fluorescent particle 201 is absent, the droplet discharger controller 21 operates to return the processing to S201.

In S204, the particle counter controller 53 controls the second particle measuring device 52, to which information on the light beam 302b emitted by the fluorescent particle 201 is output from the light receiver 42, to measure the number of the fluorescent particles 201 contained in the droplet 210. The particle counting apparatus 100B thereafter terminates the processing. Through the series of operations S201 to S204, the particle counting apparatus 100B can improve the counting accuracy and measurement speed.

Figure 7:
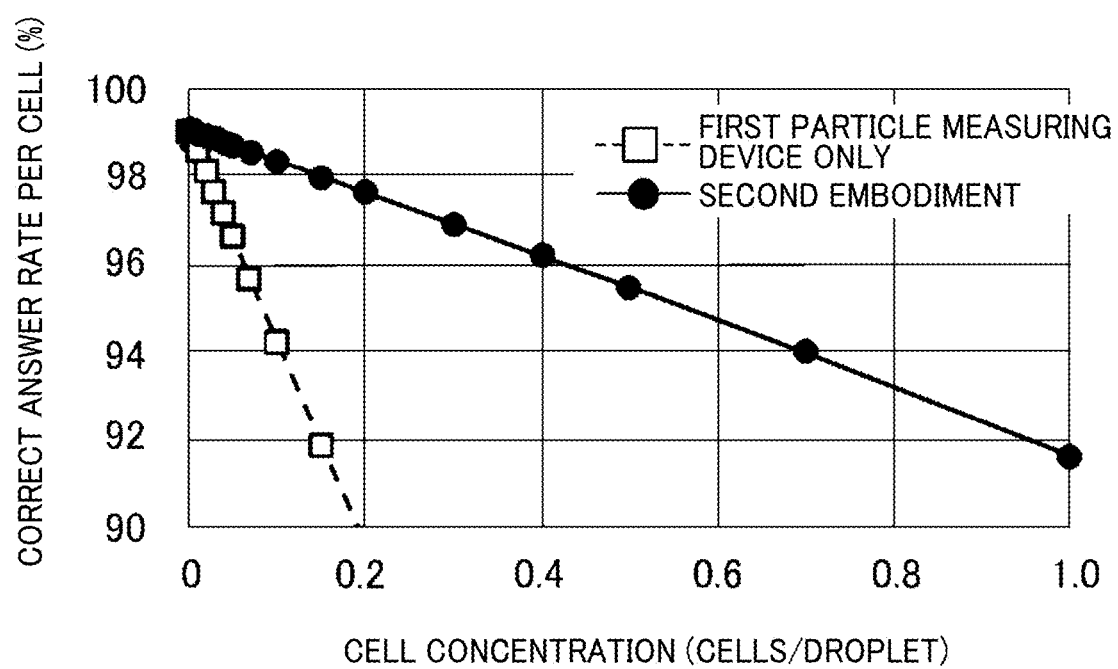
FIG. 7 is a graph illustrating measurement accuracy of the particle counting apparatus according to the second embodiment.

FIG. 7 is a graph illustrating measurement accuracy of the particle counting apparatus according to the second embodiment. FIG. 7 illustrates the measurement accuracy of the particle counting apparatus 100B illustrated in FIG. 5 when performing by the operation procedure illustrated in FIG. 6. In the evaluation of the measurement accuracy of the particle counting apparatus illustrated in FIG. 5, cells having an average diameter of 10 μm or less and stained with Evans Blue fluorescent dye are used as the fluorescent particles. Experimental conditions other than the above are almost the same as the experimental conditions for acquiring information on the emitted light presented in FIGS. 2, 3A, and 3B. Since the first particle measuring device 51 for measuring the presence or absence of the fluorescent particle 201 contained in the discharged droplet 210 and the second particle measuring device 52 for measuring the number of fluorescent particle contained in the discharged droplet 210 are compared, the light receiver 41 and the light receiver 42 that output information to the first particle measuring device 51 and the second particle measuring device 52, respectively, employ respective products having the same sensitivity level in order to reduce the influence of the difference therebetween.

The cell concentration represents the average number of fluorescent particles 201 contained in one discharged droplet 210, not the concentration of the fluorescent particles 201 in the particle suspension 200 per volume. The cell concentration is adjusted to be about 0.25 cells/droplet. However, since the particle suspension 200 in the liquid chamber 11 is not stirred during the discharge of droplets, concentration fluctuation occurs due to precipitation of the fluorescent particles during the experiment. The actual number of fluorescent particles contained in the discharged droplet 210 is determined by visually observing an image of the fluorescent particles contained in the landed droplet obtained with a fluorescence microscope (AXIO OBSERVER manufactured by Carl Zeiss Microscopy) using an objective lens having a magnification of 20 times.

Table 1 presents the results obtained with the first particle measuring device 51 only. That is, the results indicate only the presence or absence of cell, not the number of fluorescent particles 201 contained in the discharged droplet 210. The number of cells contained in the landed droplet represents that contained in the actually discharged droplet 210. The presence or absence of cell was measured for each of the droplets containing zero cell, one cell, two cells, three cells, or four cells. With respect to droplets containing zero cell, the rate of correct answers is 100% since there is no light emission from the droplet 210. However, with respect to droplets containing one cell, there is one wrong answer. The reason for this erroneous measurement that the fluorescent particle is absent is considered that the fluorescent particles have became dark due to at least one of the following causes: the amount of illumination light emitted by the light irradiator 30 has a distribution, the light use efficiency in receiving light by the light receiver 41 also has a distribution, and the light emission efficiency of the fluorescent particles themselves have fluctuations. However, the rate of correct answers is 99% or more.

With respect to droplets containing two or more cells, the presence of cell is confirmed in all the cases and the rate of correct answers is 100%. However, when preparing a particle containing sample by discharging one fluorescent particle to a predetermined well on a microplate, it is unknown whether the droplet in which the presence of fluorescent particle is confirmed contains one, two, three, or four fluorescent particles, thus affecting the measurement accuracy.

Table 2 presents the results obtained with the second particle measuring device 52 only. That is, unlike Table 1, the results indicate the measured number of fluorescent particles 201 contained in the discharged droplet 210. The number of cells contained in the landed droplet represents that contained in the actually discharged droplet 210. The number of cells was measured for each of the droplets containing zero cell, one cell, two cells, three cells, or four cells.

With respect to droplets containing zero cell, the rate of correct answers is 100% since there is no light emission from the droplet 210. This result depends on whether there is a signal based on light emitted by the fluorescent particle 201 or there is only noise and no signal. Since the same product was used for the light receivers 41 and 42, the result is the same as that in Table 1 because the sensitivity and the noise ratio thereof are the same.

In Table 2, there is one erroneous measurement in the case of the landed droplets containing one cell. This is because, similar to the case of droplets containing zero cells, the fluorescent particles may be dark, as already described above, which makes measurement difficult. In this case, since the light receiver is the same, the result is also the same. However, as in Table 1, the rate of correct answers is 99% or more.

In Table 2, there are five erroneous measurements in the case of the landed droplets containing one cell, in each of which the number of cells in the discharged droplet is measured to be two. This is because the image information becomes complicated depending on the position of the fluorescent particle 201 in the droplet 210, as illustrated in FIG. 3A, and there is a possibility that whether there is one cell or two cells is erroneously determined. Likewise, there are three erroneous measurements in the case of the landed droplets containing two cells, in each of which the number of cells in the discharged droplet is measured to be one. The rate of correct answers is 85%, which is relatively low.

There is one erroneous measurement in the case of the landed droplets containing three cells, in which the number of cells in the discharged droplet is measured to be four. There is one erroneous measurement in the case of the landed droplets containing four cells, in which the number of cells in the discharged droplet is measured to be three. Thus, there are multiple erroneous measurements with a relatively low rate of correct answers, although it is uncertain because the number of occurrences is low.

TABLE 1

Measurement of Cells in Landed Droplet

| | | | 0 cell | 1 cell | 2 cells | 3 cells | 4 cells |
|---|---|---|---|---|---|---|---|
| | | | | | Number of Cases | | |
| Measurement of Cells in Discharged Droplet | Absent | Number of Cases | 257 | 1 | 0 | 0 | 0 |
| | Present | | 0 | 108 | 20 | 4 | 2 |
| Subtotal | | | 257 | 109 | 20 | 4 | 2 |

TABLE 2

Measurement of Cells in Landed Droplet

| | | | 0 cell | 1 cell | 2 cells | 3 cells | 4 cells |
|---|---|---|---|---|---|---|---|
| | | | | | Number of Cases | | |
| Measurement of Cells in Discharged Droplet | 0 cell | Number of Cases | 257 | 1 | 0 | 0 | 0 |
| | 1 cell | | 0 | 103 | 3 | 0 | 0 |
| | 2 cells | | 0 | 5 | 17 | 0 | 0 |
| | 3 cells | | 0 | 0 | 0 | 3 | 1 |
| | 4 cells | | 0 | 0 | 0 | 1 | 1 |
| Subtotal | | | 257 | 109 | 20 | 4 | 2 |

It is necessary that the above-measured rate of correct answers is converted into the rate of correct answers (hereinafter "correct answer rate T") when one cell is discharged, in stead of one droplet is discharged, at a cell concentration to be applied according to the actual purpose, based on the results presented in Tables 1 and 2, because of the following reasons: 1) the results presented in Tables 1 and 2 are obtained with the suspension with a cell concentration of about 0.25 cells/droplet; 2) the results are obtained under the condition that only one droplet is discharged, in which the droplet obviously contains zero cell at a high probability; 3) the cell concentration in the landed droplet is unknown in actual droplet discharge; and/or 4) it is necessary to consider the rate of correct answers with respect to the measurement of the discharged droplet in stead of the measurement of the landed droplet.

The converted value of the correct answer rate T when one cell is discharged can be obtained in the following manner. First, the results presented in Tables 1 and 2, obtained under the cell concentration of about 0.25 cells/droplet, are converted into those obtained under a cell concentration value to be applied according to the purpose. Since the ratio at which each cell number occurs in the landed droplet stochastically follows the Poisson distribution determined depending on the cell concentration, the Poisson distribution at the cell concentration applied according to purpose is taken as the frequency of appearance of each cell number. Here, each cell number means the actual number of cells measured for each landed droplet. Then, the ratios are allocated based on the measured presence or absence of cells or the measured number of cells, so that the frequency of appearance of each cell number becomes the sum value. This value indicates the occurrence ratio of each element of the matrix allocated for each actual cell number and for the measured presence/absence or number of cells, on the premise that the total of all the values becomes 1.

Next, the correct answer rate in the measurement of each discharged droplet is determined. The sum of the occurrence ratio for each element is calculated with respect to all actual cell numbers for the focused measurement condition, either the presence or absence of cells or the number of cells. (This is the sum of the occurrence ratio for each element in the row, that is, the sum of the occurrence ratio for each element in the horizontal direction). The result is taken as the sum of the occurrence ratio for the focused measurement condition. Among the elements constituting the sum, the element in which the measured number under the focused measurement condition and the actual cell number coincide is a correct answer. Thus, the correct answer rate in the measurement is calculated by dividing the occurrence ratio of such an element with the above-obtained sum of the occurrence ratio for the focused measurement condition.

The correct answer rate in the measurement of flying droplets are denoted as r(OFF) and r(ON) when the cell is absent and present, respectively, in Table 1 (in which only the first particle measuring device is used); and r(0)=r(OFF), r(1), r(2), r(3), and r(4) when the number of cell is zero, one, two, three, and four, respectively, in Table 2 (in which only the second particle measuring device is used). In addition, the above-described sum for each measurement condition, which is the occurrence ratio of the focused measurement, is denoted as p(OFF) and p(ON) when the cell is absent and present, respectively, in Table 1; and p(0)=p(OFF), p(1), p(2), p(3), and p(4) when the number of cell is zero, one, two, three, and four, respectively, in Table 2.

Based on the occurrence ratio of this measurement and the correct answer rate in the occurrence of the measurement, the correct answer rate T at which the presence of at least one cell is measured or the number of cells is measured to be one after one or more times of droplet discharge can be obtained. The correct answer rate T is calculated by calculating the occurrence ratio and correct answer rate are for each event with respect to the possibility up to the number of times of droplet discharge. In order to achieve an accuracy of approximately 98% or more for the correct answer rate T, it is preferable to accumulate the product of the occurrence ratio and the correct answer rate (in the measurement of flying droplets) for each event with respect to the possibility up to the number of times of droplet discharge that is 5 to 10 times or more the reciprocal of the cell density. For example, when the cell concentration is 0.02 cells/droplet, the reciprocal thereof is 50 and 5 times of the reciprocal is 5×50=250. Therefore, it is preferable that the calculation is continued until the event in which the presence of cell is measured in the 250th droplet discharge for the first time occurs.

However, the elements of the sum of the product of the occurrence ratio and the correct answer rate consist mainly of repetition of measurement of the absence of cell (0 cell). The accumulation thereof can be analytically approximated focusing on the fact that the elements are in a geometric progression with common ratio being the product of the occurrence ratio and the correct answer rate when the cell is absent. i.e., p(OFF)×r(OFF). The correct answer rate T in the comparative case in which only the first particle measuring device 51 is used can be obtained by the following formula (1).

$$\text{Correct Answer Rate } T = \frac{p(\text{ON}) \times r(\text{ON})}{1 - (p(\text{OFF}) \times r(\text{OFF}))} \quad \text{Formula (1)}$$

In the second embodiment in which both the first particle measuring device 51 and the second particle measuring device 52 are used, when two or more cells are measured by the second particle measuring device 52, the above formula (1) is corrected to the following formula (2).

$$\text{Correct Answer Rate } T = \frac{p(\text{ON}) \times r(1)}{1 - (p(0) \times r(0))} \quad \text{Formula (2)}$$

FIG. 7 is a graph indicating the relation between the correct answer rate T when measuring the presence of cell or the number of cell being one and the cell concentration set optimally according to the purpose (on the horizontal axis), for the case in which only the first particle measuring device 51 is used and the case of the second embodiment, using the above-described formulae 1 and 2, based on the measurement results presented in Tables 1 and 2.

As illustrated in FIG. 7, there is no big difference in the correct answer rate T as measurement accuracy between the case of using the first particle measuring device 51 only and the case of the second embodiment, when the cell concentration is small. For example, when the cell concentration is 0.001 cells/droplet, the correct answer rate T in the second embodiment is 99.1%, and that of the case of using the first particle measuring device 51 only is 99.0%. This is because, in a case in which the cell concentration is low, almost no droplet containing 2 cells/droplet or more is discharged in theory, due to the probability according to the Poisson distribution.

However, in such a case in which the cell concentration is 0.001 cells/droplet, which is low, in order to obtain one cell by discharging the droplet 210, it is necessary that the droplet 210 is discharged 1,000 times in average. In particular, in order to maintain accuracy, 5,000 times of discharging of the droplet 210, which is about 5 times of the above case, should be accepted. Therefore, a low cell concentration such as 0.001 cells/droplet results in a high industrial cost.

In a case in which the cell concentration is 0.02 cells/droplet, which is a 20-times concentrated concentration, the correct answer rate T in the case of using the first particle measuring device 51 only is 98.1% whereas the correct answer rate T in the second embodiment is 98.9%. Thus, the difference in correct answer rate T expands to 0.8% or more, which makes the advantage of the second embodiment clear. When the correct answer rate T is converted into the error rate that is the inverse thereof, the error rate in the second embodiment is 1.1%, while the error rate in the case of using the first particle measuring device 51 only is 1.9%, which is about 2 times that in the second embodiment. At this cell concentration, the average number of discharging of the droplet 210 is 51. When the droplet discharger 10 is operated at 100 Hz, one cell is discharged in 0.5 seconds, providing a sufficiently low industrial cost. In addition, since the second particle measuring device 52 has been performed the number measurement for droplets containing cells, although the measurement is one time, a high level of accuracy is achieved similar to the case of only the second particle measuring device 52 is used.

Both the particle counting apparatus 100B according to the second embodiment capable of high-speed measurement and the first particle measuring device 51 alone have a frequency sufficient for responding to the operation of the droplet discharger 10 at 100 Hz. On the other hand, it is very difficult for the second particle measuring device 52 alone to complete the number measurement at a frequency of 100 Hz by outputting (transferring) a large amount of information and performing image processing, because it takes a lot of time to complete these processes, although the correct answer rate T of the second particle measuring device 52 alone is almost the same as that of the particle counting apparatus 100B according to the second embodiment. Thus, the particle counting apparatus 100B according to the second embodiment has an advantage in terms of processing speed. With respect to droplets containing cells, the correct answer rate T of the second particle measuring device 52 alone is the same level as that of the second embodiment in which the second particle measuring device 52 performs the number measurement at the last stage.

The advantage of the second embodiment increases as the cell concentration increases. For example, when the cell concentration is 0.2 cells/droplet, the correct answer rate T of the second embodiment is 97.6% whereas that of the first particle measuring device 51 alone is 89.5% (not shown in the graph because of being smaller than 90%). The difference therebetween is very large. In the industrial field, for example, samples for analytical instruments, etc. may require 1 to 100 cells and small tissue samples for evaluating medicines may require several ten thousands of cells. It requires under 10 minutes to obtain 10,000 cells by discharging droplets at 100 Hz and a cell concentration of 0.2 cells/droplet. In terms of industrial cost, the cell concentration is as high as this level. However, in the comparative case in which only the first particle measuring device 51 is used, the accuracy greatly deteriorates at this cell concentration. Thus, it is understood that the second embodiment is extremely effective.

However, in the case of using the first particle measuring device 51 only, when the cell concentration is low, specifically, when the cell concentration is 0.02 cells/droplet or less, the correct answer rate T is 97%, which is sufficiently high. This is almost the same level as that in the case of using the second particle measuring device 52 only. The first particle measuring device 51 alone has an advantage over the second particle measuring device 52 alone in that the configuration can be more simplified such that the light receiver 41 is provided only with APD and that higher speed and lower cost can be achieved. FIG. 7 does not compare the superiority or inferiority of the first particle measuring device 51 alone and the second particle measuring device 52 alone.

Figure 8:
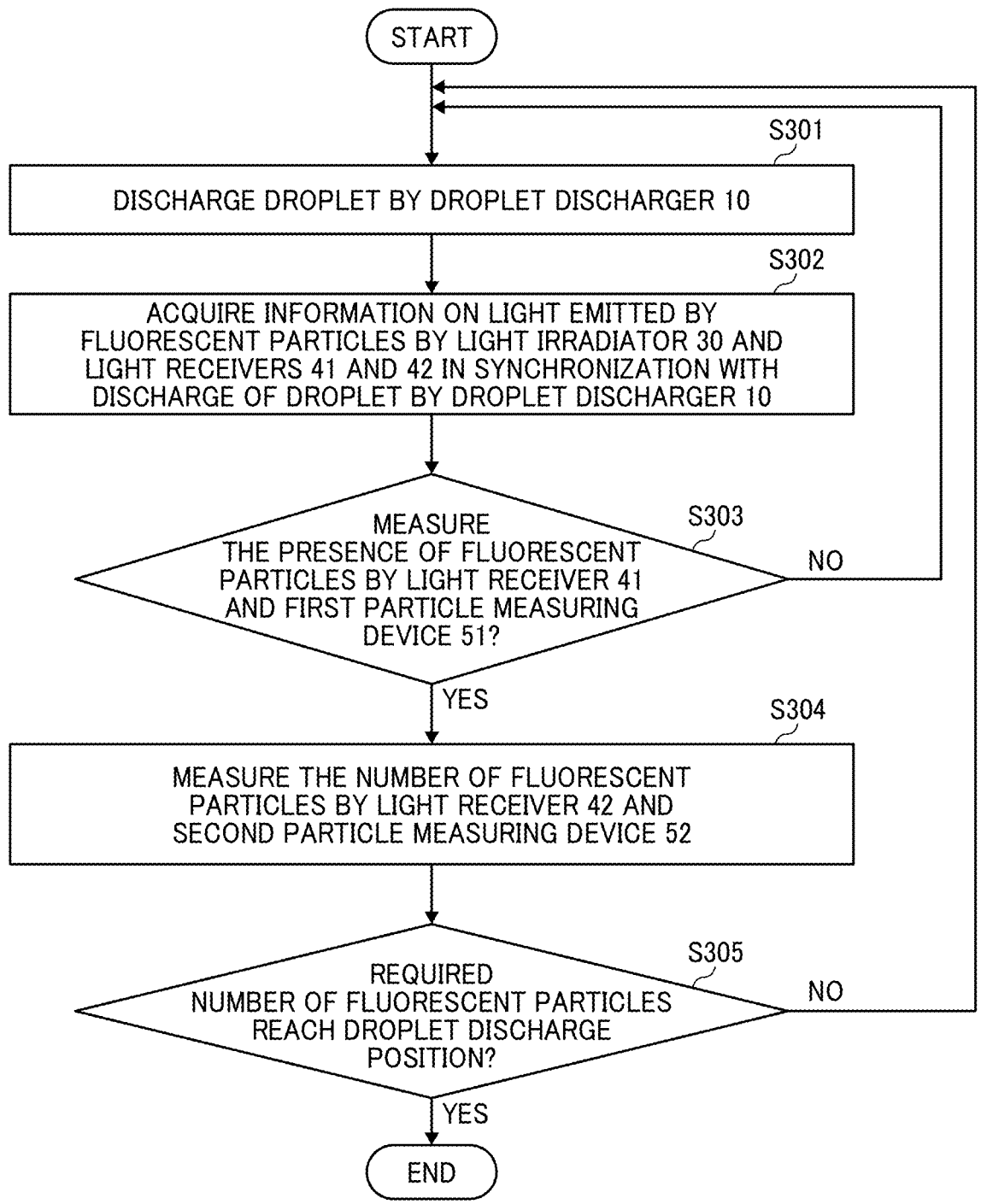
FIG. 8 is a flowchart of another operation of the particle counting apparatus according to the second embodiment.

FIG. 8 is a flowchart of another operation of the particle counting apparatus according to the second embodiment. Specifically, FIG. 8 illustrates an operation procedure, other than that illustrated in FIG. 6, of the particle counting apparatus 100B according to the second embodiment that can improve the counting accuracy and measurement speed in measuring multiple fluorescent particles. As illustrated in FIG. 7, in S301, the droplet discharger 10 to which a drive voltage is applied from the driver 20 discharges the droplet 210 containing the fluorescent particle 201 in the discharge direction 303 illustrated in FIG. 5 from the nozzle 12. The driver 20 applies a drive voltage to the droplet discharger 10 and outputs a synchronization signal to the light irradiator 30 and the two light receivers 41 and 42. The particle counting apparatus 100B thereafter transits the processing to S302.

In S302, the droplet discharger 10, to which the synchronization signal is input from the driver 20, irradiates the droplet 210 with the laser beam 301 in synchronization with a discharge of the droplet 210. As the synchronization signal is input to the light receivers 41 and 42, the light receivers 41 and 42 receive the light beam 302a and the light beam 302b, respectively, in synchronization with light emission of the fluorescent particle 201 irradiated with the laser beam 301 emitted by the light irradiator 30. As a result, the light receivers 41 and 42 acquire information on light emitted by the fluorescent particles 201. The particle counting apparatus 100B thereafter transits the processing to S303.

In S303, the first particle measuring device 51, to which information on the light beam 302a emitted by the fluorescent particle 201 is output from the light receiver 41, measures the presence or absence of the fluorescent particle 201 contained in the droplet 210 and determines the presence or absence of the fluorescent particle 201. When it is determined that the fluorescent particle 201 is present, the particle counting apparatus 100B transits the processing to S304. When it is determined that the fluorescent particle 201 is absent, the droplet discharger controller 21 operates to return the processing to S301.

In S304, the second particle measuring device 52, to which information on the light beam 302b emitted by the fluorescent particle 201 is output from the light receiver 42, measures the number of the fluorescent particles 201 contained in the droplet 210. The particle counting apparatus 100B thereafter transits the processing to S305.

In S305, the droplet discharger controller 21 accumulates the number of the fluorescent particles 201 contained in the droplet 210 measured by the second particle measuring device 52. It is determined whether or not the accumulated number has reached the number of fluorescent particles required at a predetermined droplet discharge position. When it is determined that the accumulated number has reached the required number of fluorescent particles, the particle counting apparatus 100B terminates the processing. When it is determined that the accumulated number has not reached the required number of fluorescent particles, the droplet discharger controller 21 operates to return the processing to S301. Through the series of operations S301 to S305, the particle counting apparatus 100B can improve the counting accuracy and measurement speed in measuring multiple fluorescent particles.

Third Embodiment

Figure 9:
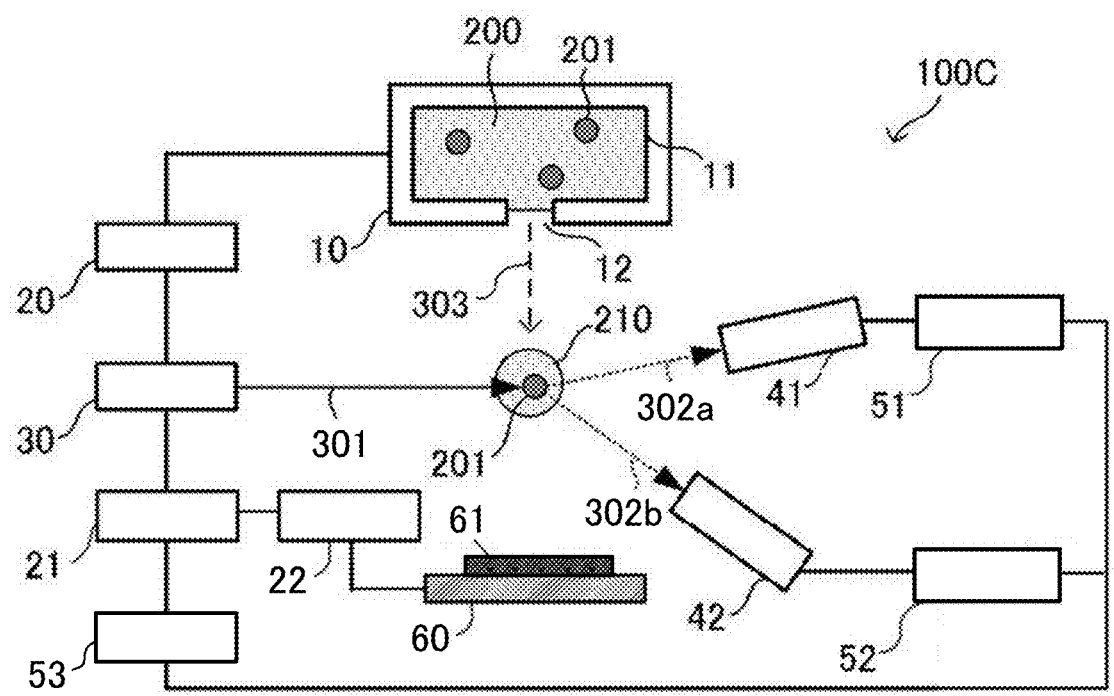
FIG. 9 is a diagram of a particle counting apparatus according to a third embodiment.

FIG. 9 is a schematic diagram of a particle counting apparatus according to a third embodiment. The particle counting apparatus according to the third embodiment illustrated in FIG. 9 has a similar configuration to the particle counting apparatus according to the second embodiment illustrated in FIG. 5, but is different in that a continuous discharge position controller is provided. The continuous discharge position controller is configured to control a droplet discharge position such that droplets are continuously discharged to a substantially same position based on information from the first particle measuring device that the luminescent particle is absent in the droplet.

The particle counting method according to the third embodiment further includes, in addition to the processes in the particle counting apparatus according to the second embodiment, the processes of: controlling a droplet discharge position such that droplets are continuously discharged to a substantially same position based on information from the firstly measuring that the luminescent particle is absent in the droplet; and moving the droplet discharge position based on information from the controlling process.

The process of controlling the droplet discharge position is preferably performed by the continuous discharge position controller.

Referring to FIG. 9, a particle counting apparatus 100C includes a droplet discharger 10 equipped with a liquid chamber 11 and a nozzle 12, a driver 20, a light irradiator 30, light receivers 41 and 42, a first particle measuring device 51, a second particle measuring device 52, a particle counter controller 53, a droplet discharger controller 21, a continuous discharge position controller 22, a droplet discharge position mover 60 carrying a microplate 61. A particle suspension 200 contains fluorescent particles 201. A droplet 210 is discharged from the nozzle 12 of the droplet discharger 10 in a discharge direction 303. Laser beam 301 is emitted by the light irradiator 30. Light beam 302a is received by the light receiver 41. Light beam 302b is received by the light receiver 42.

Hereinafter, with regard to the third embodiment illustrated in FIG. 9, a description for the same configuration as that in FIG. 5 will be partially omitted. When the first particle measuring device 51 outputs information that the fluorescent particle 201 is present in the droplet 210, the droplet discharger controller 21 controls the second particle measuring device 52 to measure the number of the fluorescent particle 201 in the same manner as in the first embodiment illustrated in FIGS. 1 and 5. When the first particle measuring device 51 outputs information that the fluorescent particle 201 is absent in the droplet 210, the droplet discharger controller 21 outputs signals at appropriate timing to cause the light irradiator 30 to emit the laser beam 301 again, the droplet discharger 10 to discharge a droplet again, the light receivers 41 and 42 to receive light, and the first particle measuring device 51 and the second particle measuring device 52 to perform the particle measurement again. As a result, the second discharge of the droplet 210 and the accompanied measurement of the fluorescent particle 201 in the droplet 210 are performed.

In measuring the fluorescent particle 201 contained in the droplet 210 discharged in the second discharge, when the first particle measuring device 51 outputs information that the fluorescent particle 201 is present in the droplet 210, the particle counter controller 53 controls the second particle measuring device 52 to measure the number of the fluorescent particle 201, in the same manner as in the first discharge, and thereafter terminates the measurement of the particles and the discharge of droplets. When the first particle measuring device 51 outputs information that the fluorescent particle 201 is absent in the droplet 210, the droplet discharger controller 21 outputs signals at appropriate timing to cause the light irradiator 30 to emit the laser beam 301 again, the droplet discharger 10 to discharge a droplet again, the light receivers 41 and 42 to receive light, and the first particle measuring device 51 and the second particle measuring device 52 to perform the particle measurement again, in the same manner as in the first discharge. As a result, the third discharge of the droplet 210 and the accompanied measurement of the fluorescent particle 201 in the droplet 210 are performed. Until the first particle measuring device 51 measures the presence of the fluorescent particle in the droplet 210, the droplet discharger controller 21 controls the droplet discharger 10 and the related modules so as to repeat the same operations. Repetition of the operations is terminated when the first particle measuring device 51 measures the presence of the fluorescent particle in the droplet 210 and the particle counting apparatus 100C thereafter acquires information on the number of the fluorescent particle measured by the second particle measuring device 52.

When one or more fluorescent particles are required at a predetermined droplet discharge position, i.e., a specific well on the microplate 61 being an adherend target of the fluorescent particles, by these operations, the particle counting apparatus is capable of measuring the number of fluorescent particle 201 in the droplet 210 discharged from the droplet discharger 10 with high accuracy and at a high speed. Even when two or more fluorescent particles are required at a predetermined droplet discharge position, i.e., a specific well on the microplate 61, the particle counting apparatus is capable of measuring the particle with high accuracy and at a high speed by, in addition to the above-described operations, continuing the droplet discharge control of the droplet discharger 10 by the droplet discharger controller 21 and the measurement by the first particle measuring device 51 and the second particle measurement means 52, until it is determined that particles are accumulated to a predetermined number by adding information on the number measured by the second particle measuring device 52. During continuous discharge to a predetermined droplet discharge position, i.e., to the specific well on the microplate 61, the continuous discharge position controller 22 controls the droplet discharge position mover 60 carrying the microplate 61 so as not to move its position.

The microplate 61 is not particularly limited and can be appropriately selected according to the purpose. Examples of the microplate 61 include, but are not limited to, a single-hole microtube, an eight-tandem tube, a 96-hole well plate, and a 384-hole well plate.

After completion of landing of the predetermined number of fluorescent particles measured at high accuracy by continuous discharge to a predetermined droplet discharge position, i.e., to the specific well on the microplate 61, the droplet discharger controller 21 operates such that, while the droplet discharger 10 suspends discharging droplets, the continuous discharge position controller 22 controls the droplet discharge position mover 60 carrying the microplate 61 to shift the continuous discharge position being a part of the microplate 61 from the landed position on the microplate 61 where the florescent particles have been landed to a new landing position being another specific well.

After that, the number of fluorescent particles landed on the continuous discharge position being a part of the microplate 61 is set to zero. When the first particle measuring device 51 outputs information that the fluorescent particle 201 is present in the droplet 210, the particle counter controller 53 controls the second particle measuring device 52 to measure the number of the fluorescent particle 201 in the same manner as in the second embodiment illustrated in FIG. 5. When the first particle measuring device 51 outputs information that the fluorescent particle 201 is absent in the droplet 210, the droplet discharger controller 21 outputs signals at appropriate timing to cause the light irradiator 30 to emit the laser beam 301 again, the droplet discharger 10 to discharge a droplet again, the light receivers 41 and 42 to receive light, and the first particle measuring device 51 and the second particle measuring device 52 to perform the particle measurement again. As a result, the second discharge of the droplet 210 to a specific well on the microplate 61 being a new predetermined droplet discharge position and the accompanied measurement of the fluorescent particle 201 in the droplet 210 are performed. By continuing the same operation, when one or more fluorescent particles are required at the predetermined droplet discharge position, i.e., a specific well on the microplate 61, the number of fluorescent particle 201 in the droplet 210 discharged from the droplet discharger 10 can be measured with high accuracy and at a high speed.

Figure 10:
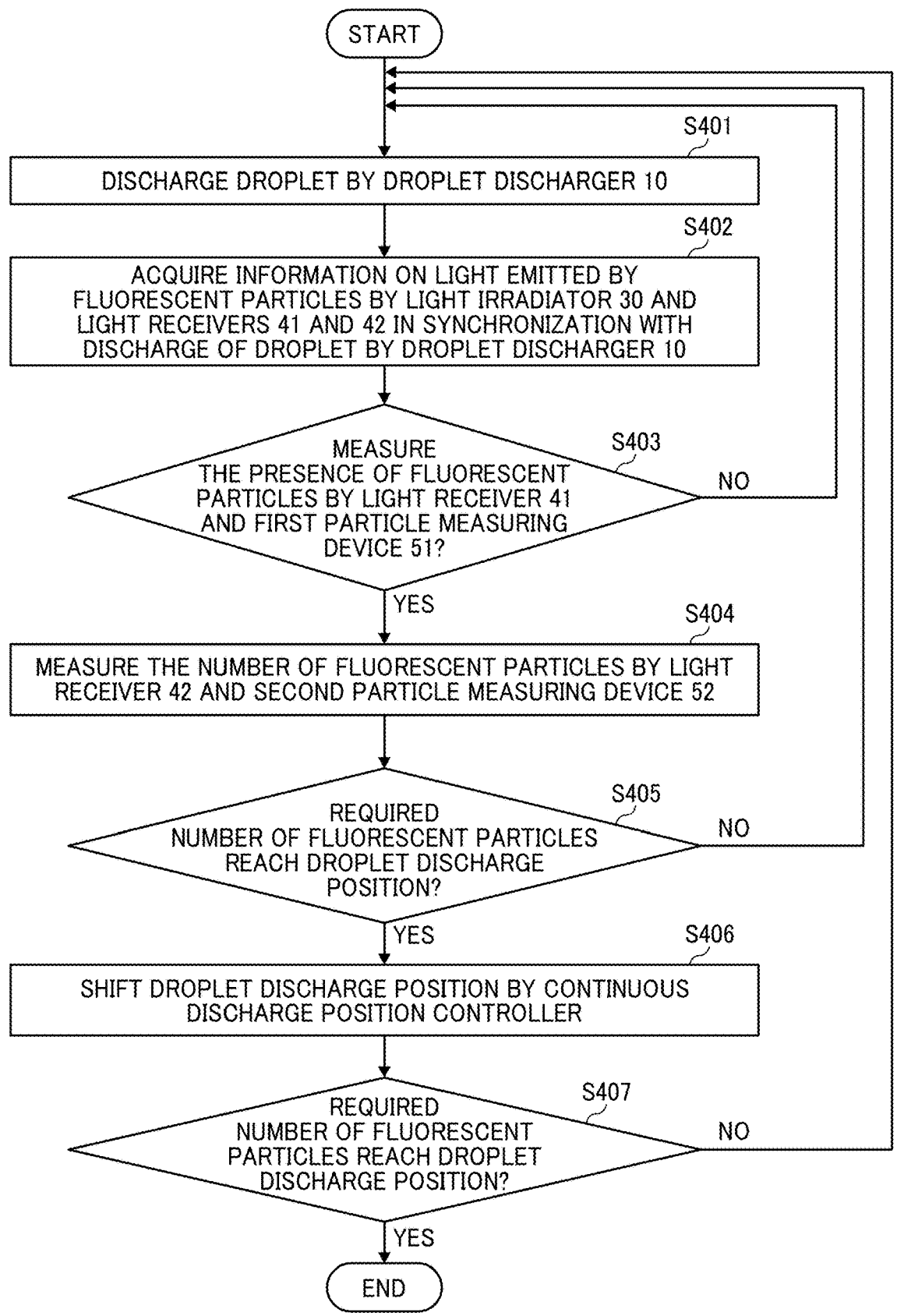
FIG. 10 is a flowchart of an operation of the particle counting apparatus according to the third embodiment.

FIG. 10 is a flowchart of an operation of the particle counting apparatus according to the third embodiment. Specifically, FIG. 10 illustrates an operation procedure of the particle counting apparatus 100C according to the third embodiment that can improve the counting accuracy and measurement speed in measuring multiple fluorescent particles. As illustrated in FIG. 10, in S401, the droplet discharger 10 to which a drive voltage is applied from the driver 20 discharges the droplet 210 containing the fluorescent particle 201 in the discharge direction 303 illustrated in FIG. 9 from the nozzle 12. The driver 20 applies a drive voltage to the droplet discharger 10 and outputs a synchronization signal to the light irradiator 30 and the two light receivers 41 and 42. The particle counting apparatus 100C thereafter transits the processing to S402.

In S402, the droplet discharger 10, to which the synchronization signal is input from the driver 20, irradiates the droplet 210 with the laser beam 301 in synchronization with a discharge of the droplet 210. As the synchronization signal is input to the light receivers 41 and 42, the light receivers 41 and 42 receive the light beam 302a and the light beam 302b, respectively, in synchronization with light emission of the fluorescent particle 201 irradiated with the laser beam 301 emitted by the light irradiator 30. As a result, the light receivers 41 and 42 acquire information on light emitted by the fluorescent particles 201. The particle counting apparatus 100C thereafter transits the processing to S403.

In S403, the first particle measuring device 51, to which information on the light beam 302a emitted by the fluorescent particle 201 is output from the light receiver 41, measures the presence or absence of the fluorescent particle 201 contained in the droplet 210 and determines the presence or absence of the fluorescent particle 201. When it is determined that the fluorescent particle 201 is present, the particle counting apparatus 100C transits the processing to S404. When it is determined that the fluorescent particle 201 is absent, the droplet discharger controller 21 operates to return the processing to S401.

In S404, the second particle measuring device 52, to which information on the light beam 302b emitted by the fluorescent particle 201 is output from the light receiver 42, measures the number of the fluorescent particles 201 contained in the droplet 210. The particle counting apparatus 100C thereafter transits the processing to S405.

In S405, the droplet discharger controller 21 accumulates the number of the fluorescent particles 201 contained in the droplet 210 measured by the second particle measuring device 52. It is determined whether or not the accumulated number has reached the number of fluorescent particles required at a predetermined droplet discharge position. When it is determined that the accumulated number has reached the required number of fluorescent particles, the particle counting apparatus 100C transits the processing to S406. When it is determined that the accumulated number has not reached the required number of fluorescent particles, the droplet discharger controller 21 operates to return the processing to S401.

In S406, the continuous discharge position controller 22 moves the droplet discharge position mover 60 to shift a continuous discharge position being a part of the microplate 61 so that a droplet is landed at another droplet discharge position being a part of the microplate 61. The particle counting apparatus 100C thereafter transits the processing to S407.

In S407, it is determined whether the fluorescent particles required at the predetermined droplet discharge position have all been landed or not. When it is determined that all the fluorescent particles have been landed, the particle counting apparatus 100C terminates the processing. When it is determined that the required number of fluorescent particles have not been landed, the droplet discharger controller 21 and the continuous discharge position controller 22 operate to return the processing to S401.

Fourth Embodiment

Figure 11:
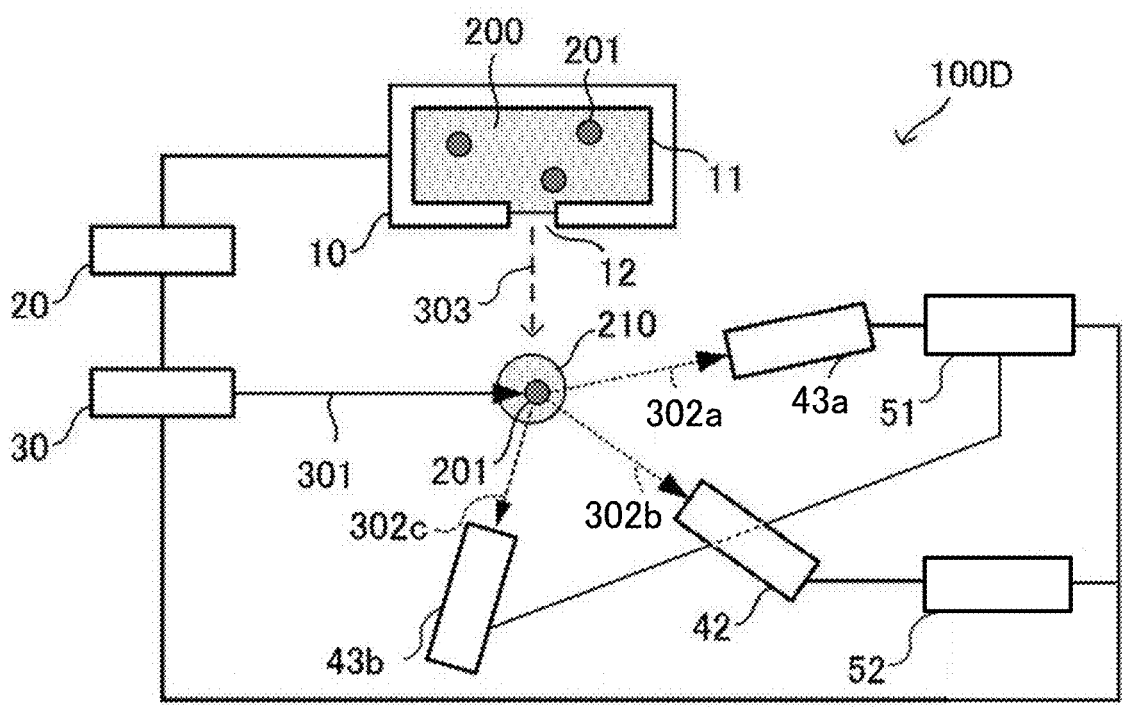
FIG. 11 is a schematic diagram of a particle counting apparatus according to a fourth embodiment.

FIG. 11 is a schematic diagram of a particle counting apparatus according to a fourth embodiment.

The particle counting apparatus according to the fourth embodiment includes two or more light receivers, each coupled to the first particle measuring device, that respectively receives light beams emitted in two or more different directions.

The particle counting apparatus according to the fourth embodiment illustrated in FIG. 11 has a similar configuration to the particle counting apparatus according to the first embodiment illustrated in FIG. 1, but is different in that two light receivers that output information to the first particle measuring device are disposed in different directions. Referring to FIG. 11, a particle counting apparatus 100D includes a droplet discharger 10 equipped with a liquid chamber 11 and a nozzle 12, a driver 20, a light irradiator 30, light receivers 42, 43a, and 43b, a first particle measuring device 51, and a second particle measuring device 52. A particle suspension 200 contains fluorescent particles 201. A droplet 210 is discharged from the nozzle 12 of the droplet discharger 10 in a discharge direction 303. Laser beam 301 is emitted by the light irradiator 30. Light beam 302a is received by the light receiver 43a. Light beam 302b is received by the light receiver 42. Light 302c is received by the light receiver 43b.

Hereinafter, with regard to the fourth embodiment illustrated in FIG. 11, a description for the same configuration as that in FIG. 1 will be partially omitted. As illustrated in FIG. 11, the three light receivers 43a, 43b, and 42 are electrically coupled to the driver 20 via the light irradiator 30. The driver 20 inputs a synchronization signal to the light receivers 43a, 43b, and 42. As the synchronization signal is input to the light receivers 43a, 43b, and 42, the light receivers 43a, 43b, and 42 receive the light beam 302a, the light 302c, and the light beam 302b, respectively, in synchronization with light emission of the fluorescent particle 201 irradiated with the laser beam 301 emitted by the light irradiator 30.

Each of the light receivers 43a and 43b is a light sensing device/module capable of measuring the presence or absence of the fluorescent particle 201 contained in the droplet 210. The light receiver 42 is a light sensing device/module capable of measuring the number of the fluorescent particle 201 contained in the droplet 210. The light receivers 43a and 43b and the light receiver 42 output light receiving information to the first particle measuring device 51 and the second particle measuring device 52, respectively, that are respectively electrically coupled thereto. Based on the information output from the light receivers 43a, 43b, and 42, the first particle measuring device 51 measures the presence or absence of the fluorescent particle 201 contained in the droplet 210, and the second particle measuring device 52 measures the number of the fluorescent particle 201 contained in the droplet 210.

The light receiver 42 measures the number of the fluorescent particle 201 in cooperation with the second particle measuring device 52. This measurement is a quantitative measurement that provides a higher degree of accuracy compared to the qualitative measurement performed by the light receivers 43a and 43b. Thus, the light receiver 42 is a light sensing device/unit which acquires a larger amount of information compared to the light receivers 43a and 43b and the second particle measuring device 52 is capable of processing more complicated information compared to the first particle measuring device 51.

The received amount of light emitted by the fluorescent particle 201 contained in the droplet 210 by the light receivers 43a and 43b largely fluctuates depending on the disposition direction of the light receivers 43a and 43b.

This phenomenon is based on the lens action of the droplet 210 that is caused by the fact that the droplet 210 is composed mainly of water having a refractive index n of 1.333 and has a very small curvature due to its diameter of about 40 to 100 μm. Since the disposition directions of the light receivers 43a and 43b are different, the relative positions of the fluorescent particles in the droplet 210 with respect to the light receivers 43a and 43 are different and the lens action thereof are different. Thus, the received amount of light emitted from the fluorescent particle 201 contained in the droplet 210 is different between the light receivers 43a and 43b.

For the above reason, in the first embodiment, there is a case that the received amount of light emitted by the fluorescent particles 201 by the light receiver 41 largely varies for each droplet 210, which causes a deterioration in measurement accuracy. This variation may be a problem in setting the dynamic range or the threshold value in the measurement. With regard to the lens action of the droplet 210, when the amount of emitted light becomes very small due to this variation and comes close to the level of noise, there may be a problem that measurement accuracy deteriorates, although depending on the performances of the laser beam irradiated as illumination light and the fluorescent particles.

The particle counting apparatus 100D according to the fourth embodiment illustrated in FIG. 11 solves this problem. That is, since the light receivers 43a and 43b that output information to the first particle measuring device 51 are disposed in different directions, the frequency with which the amount of light emitted from the fluorescent particles 201 decreases due to the lens action of the droplet 210 is largely reduced. Accordingly, the accuracy of measurement on the presence or absence of fluorescent particles by the first particle measuring device 51, having received information on the received light from the light receivers 43a and 43b, is improved.

The number of light receivers disposed in different directions for outputting information to the first particle measuring device 51 is not limited to two. As the number is increased to three, four, and more, the frequency with which the amount of light emitted from the fluorescent particles 201 decreases due to the lens action of the droplet 210 is more reduced and the measurement accuracy is more improved. The different directions are not limited to differ in horizontal direction. It is also effective to differ the directions in vertical direction.

FIGS. 12A and 12B are diagrams illustrating distributions of the received amount of light emitted from the fluorescent particles by a camera lens, obtained by an optical simulation, as an example that indicates the degree of reduction of the frequency with which the amount of emitted light decreases due to the provision of two or more light receivers for outputting information to the first particle measuring device 51 in different directions. FIG. 12A illustrates a case corresponding to the first embodiment illustrated in FIG. 1 in which one light receiver for outputting information to the first particle measuring device 51 is disposed. FIG. 12B illustrates a case corresponding to the fourth embodiment illustrated in FIG. 11 in which two light receivers for outputting information to the first particle measuring device 51 are disposed in different directions. The center of the cross section of the droplet 210 is taken as the origin of the zy axis, the horizontal z axis (unit: μm) represents the optical axis direction in which the right side of the drawing is positive, and the vertical y axis (unit: μm) represents the image height direction in which the upper side of the drawings is positive. Factors for the decrease of the amount of emitted light include, other than the above-described lens action of the droplet with respect to the direction of the light receiver, variations in fluorescence characteristics of the fluorescent particles, the lens action of the droplets with respect to the direction of the light irradiator, and the like. Since it is difficult to measure the position of the fluorescent particle 201 in the droplet 210, it is also difficult to conduct accurate quantitative comparison of two of the above three factors by experiment. Therefore, it is appropriate to conduct comparison by optical simulation.

The optical simulation was conducted as follows. The optical simulation was conducted by a PC using an optical simulation tool LightTools 8.4.0 (manufactured by Cybernet Systems Co., Ltd.). In an optical model, it is assumed that the diameter of the droplet 210 is 80 μm, the diameter of the fluorescent particle 201 is 5 μm, the refractive index of water constituting the droplet is 1.333, and the light receiver 41 for receiving light emitted from the fluorescent particle 201 in the droplet 210 is composed of a 6× camera lens (NA=0.68) disposed separated with a working distance of 220 mm and a light receiving element having a diameter of 1 mm disposed on the imaging plane of the camera lens. At the interface of the droplets, transmission reflection was set based on the Fresnel coefficient and light beams up to three incidences were traced. As the 6× camera lens, a nearly-aberration-free virtual lens was designed assuming VS-TC6-220CO (manufactured by VS Technology). The light receiving diameter was set assuming that the light receiving element was an APD manufactured by Thorlabs Japan Inc.

The center of the cross section of the droplet 210 is taken as the origin of the zy axis, the horizontal z axis (unit: µm) represents the optical axis direction in which the right side of the drawing is positive, and the vertical y axis (unit: µm) represents the image height direction in which the upper side of the drawings is positive. The front surface of the camera lens is on the position where z=220 mm. The center positions of the fluorescent particles 201 in the droplet 210 were allocated at a pitch of 5 µm around the origin. The amount of light received at each position of the fluorescent particle 201 when a certain amount of light was emitted from the fluorescent particles 201 was calculated. Since the fluorescent particles serve as omnidirectional divergent light sources, the calculation was performed while setting the number of light beams to 50 million lines, thus ensuring necessary accuracy on the imaging plane of the camera lens. For comparison, the distribution illustrated in FIG. 12A has been normalized such that the amount of light received at the position (z, y)=(35, 0) on the right end of the droplet 210 on the side of the camera lens, where the lens action of the droplet is relatively small, is 1.0.

As illustrated in FIG. 12A, as the position of the fluorescent particle 201 comes closer to the left end of the droplet 210 opposite to the camera lens on the optical axis, the amount of received light is increased up to 12 times compared to that on the right end where the lens action is small. This is because the droplet 210 acts as a convex lens and the solid angle that can be received by the camera lens is increased. On the other hand, as the position of the fluorescent particle 201 comes closer to the upper or lower end of the droplet at which the distance from the optical axis is large, the amount of received light is decreased to $\frac{1}{10}$ at minimum compared to that on the right end where the lens action is small. The amount of light received at the positions (z, y)=(−25, −25) and (−25, 25) is zero.

The droplet 210, acting as a convex lens, also acts similar to a collimator lens against light emitted at a large emission angle, so that most of the light emitted from the fluorescent particle 201 propagates in a direction different from the direction in which the camera lens is located. Depending on the position of the fluorescent particle 201 in the droplet 210, there may be a case in which the amount of received light is very small even if the amount of emitted light at the position is the same. Even when the fluorescent particle is present inside the droplet 210, the presence of the fluorescent particle cannot be measured at the position where the amount of received light is zero.

FIG. 12B illustrates a distribution of the total amount of light received by the light receivers 43a and 43b in a case in which the light receivers 43a and 43b are disposed in different directions, more specifically, at opposite positions (180 degrees apart around the droplet 210). As the position of the fluorescent particle 201 comes closer to the left or right end of the droplet 210 from the origin, the amount of received light is increased up to 13 times compared to that on the right end in the case of FIG. 12A where the lens action is small. However, this value is almost the same as in the case of FIG. 12A. On the other hand, in the case of FIG. 12B, as the position of the fluorescent particle 201 comes closer to the upper or lower end of the droplet at which the distance from the optical axis is large, the amount of received light is decreased to ½ at most compared to that on the right end where the lens action is small. Thus, it is clear that when the lower limit of the amount of received light is set to about one-half of that in a case in which there is no lens action of the droplet, a measurement with high accuracy can be performed. Also, the upper limit of the amount of received light may be substantially the same as in the case of FIG. 12A.

In FIG. 11, when the number of light receivers for outputting information to the first particle measuring device 51 is two or more, it is effective that at least two of the light receivers are disposed in substantially opposite directions (the angle therebetween is approximately 180 degrees, here, 160 to 200 degrees). This is the above-described case of FIG. 12B in which the position where the amount of received light is zero has been eliminated and, at the same time, the minimum amount of received light has been increased compared to the case of FIG. 12A. However, for example, in a case in which two light receivers are disposed in orthogonal directions (the angle therebetween is approximately 90 degrees, here, 80 to 100 degrees), the position where the amount of received light is zero may remain, which is less effective. However, even in this case, the minimum amount of received light is 0.4 at positions other than the position where the amount of received light is zero, which has been improved from the case of only one light receiver.

In FIG. 11, the number of light receivers disposed in different directions for outputting information to the first particle measuring device 51 is not limited to two. As the number is increased, the frequency with which the amount of emitted light decreases is more reduced. The different directions are not limited to differ in horizontal direction. It is also effective to differ the directions in vertical direction. It is effective to optimize these conditions based on required detection accuracy, layout limitation, cost, and the like.

Fifth Embodiment

Figure 13:
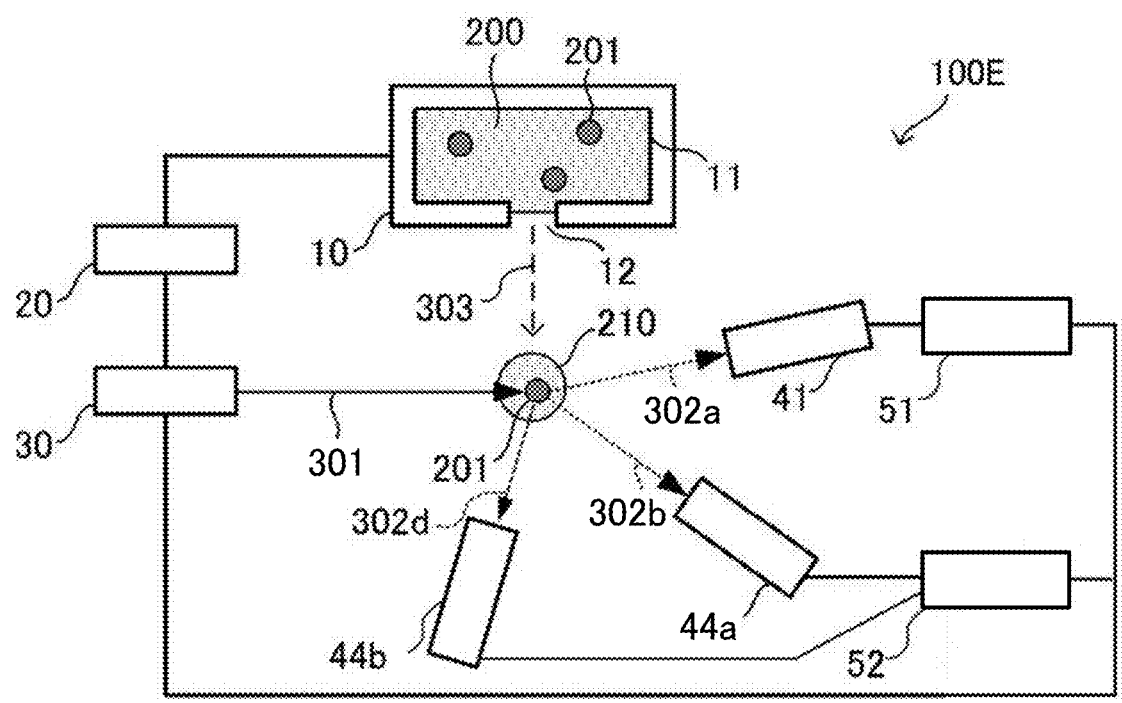
FIG. 13 is a schematic diagram of a particle counting apparatus according to a fifth embodiment.

FIG. 13 is a schematic diagram of a particle counting apparatus according to a fifth embodiment.

The particle counting apparatus according to the fifth embodiment includes two or more light receivers, each coupled to the second particle measuring device, that respectively receives light emitted in two or more different directions.

The particle counting apparatus according to the fifth embodiment illustrated in FIG. 13 has a similar configuration to the particle counting apparatus according to the first embodiment illustrated in FIG. 1, but is different in that two light receivers that output information to the second particle measuring device are disposed in different directions. Referring to FIG. 13, a particle counting apparatus 100E includes a droplet discharger 10 equipped with a liquid chamber 11 and a nozzle 12, a driver 20, a light irradiator 30, light receivers 41, 44a, and 44b, a first particle measuring device 51, and a second particle measuring device 52. A particle suspension 200 contains fluorescent particles 201. A droplet 210 is discharged from the nozzle 12 of the droplet discharger 10 in a discharge direction 303. Laser beam 301 is emitted by the light irradiator 30. Light beam 302a is received by the light receiver 41. Light beam 302b is received by the light receiver 44a. Light 302d is received by the light receiver 44b.

Hereinafter, with regard to the fifth embodiment illustrated in FIG. 13, a description for the same configuration as that in FIG. 1 will be partially omitted. As illustrated in FIG. 13, the three light receivers 41, 44a, and 44b are electrically coupled to the driver 20 via the light irradiator 30. The driver 20 inputs a synchronization signal to the light receivers 41, 44a, and 44b. As the synchronization signal is input to the light receivers 41, 44a, and 44b, the light receivers 41, 44a, and 44b receive the light beam 302a, the light beam 302b, and the light 302d, respectively, in synchronization with light emission of the fluorescent particle 201 irradiated with the laser beam 301 emitted by the light irradiator 30.

The light receiver 41 is a light sensing device/module capable of measuring the presence or absence of the fluorescent particle 201 contained in the droplet 210. Each of the light receivers 44a and 44b is a light sensing device/module capable of measuring the number of the fluorescent particle 201 contained in the droplet 210. The light receiver 41 and the light receivers 44a and 44b output light receiving information to the first particle measuring device 51 and the second particle measuring device 52, respectively, that are respectively electrically coupled thereto. Based on the information output from the light receivers 41, 44a, and 44b, the first particle measuring device 51 measures the presence or absence of the fluorescent particle 201 contained in the droplet 210, and the second particle measuring device 52 measures the number of the fluorescent particle 201 contained in the droplet 210.

The light receivers 44a and 44b measure the number of the fluorescent particle 201 in cooperation with the second particle measuring device 52. This measurement is a quantitative measurement that provides a higher degree of accuracy compared to the qualitative measurement performed by the light receiver 41. Thus, each of the light receivers 44a and 44b is a light sensing device/unit which acquires a larger amount of information compared to the light receiver 41 and the second particle measuring device 52 is capable of processing more complicated information compared to the first particle measuring device 51.

Since two or more light receivers for outputting information to the second particle measuring device 52 are provided, even when one of the light receiver receives light emissions in an overlapping manner, other one of the light receiver may receive light emissions in a non-overlapping manner, so that the fluorescent particles 201 contained in the droplet 210 are counted at high accuracy based on the light received by the other one of the light receiver.

The fluorescent particles irradiated with laser beam emit light in all directions. Therefore, the two or more light receivers are not particularly limited as long as they are disposed at a position capable of receiving emitted light, and can be appropriately selected according to the purpose. Preferably, the light receivers are disposed such that the angle formed between the light receiving directions thereof is not zero degree. In this case, information is obtained in a state of less overlapping of light emission, which is advantageous.

Preferably, at least one of the two or more light receivers for outputting information to the second particle measuring device 52 is disposed such that the light receiving direction thereof is substantially orthogonal to the light receiving direction of the other light receivers. Thus, among information received by the one of the light receivers and the other light receivers, information in a state of less overlapping of light emission can be selected. Here, "substantially orthogonal" refers to a state in which the angle therebetween ranges from 80 to 100 degrees.

The light receiving directions of the two or more light receivers for outputting information to the second particle measuring device 52 are not particularly limited and can be appropriately selected according to the purpose. When two or more light receivers are disposed on the same plane, it is preferable that the angle formed between the light receiving directions of the adjacent light receivers is an angle obtained by equally dividing 360 degrees by the number of light receivers. For example, when four light receivers are disposed on the same plane, it is preferable that the angle formed between the light receiving directions of the adjacent light receivers is 90 degrees. In this case, the combination of the light receivers in the opposite direction is effective because it is possible to reduce the frequency with which the amount of emitted light decreases depending on the position of the fluorescent particles 201 in the droplet 210. For the purpose of reducing the frequency with which the amount of emitted light decreases, when the number of light receivers for outputting information to the second particle measuring device 52 is two, it is effective that the light receivers are disposed substantially opposite to each other, instead of substantially orthogonal to each other, similar to the case of the light receivers for outputting information to the first particle measuring device 51. It is also effective to increase the light receiving directions of illumination light by using a micro optical element in the vicinity of the droplet discharger 10.

The light receiver for outputting information to the first particle measuring device and the light receiver for outputting information to the second particle measuring device may be disposed in the same direction. When these light receivers are disposed in the same direction, since a change in the amount of emitted light depending on the position of the fluorescent particles 201 in the droplet 210 is the same, information with reduced influence due to difference in position may be output to the first particle measuring device and the second particle measuring device. This configuration can be achieved by distributing light emitted from fluorescent particles by a beam splitter, a slit, or the like.

Sixth Embodiment

Figure 14:
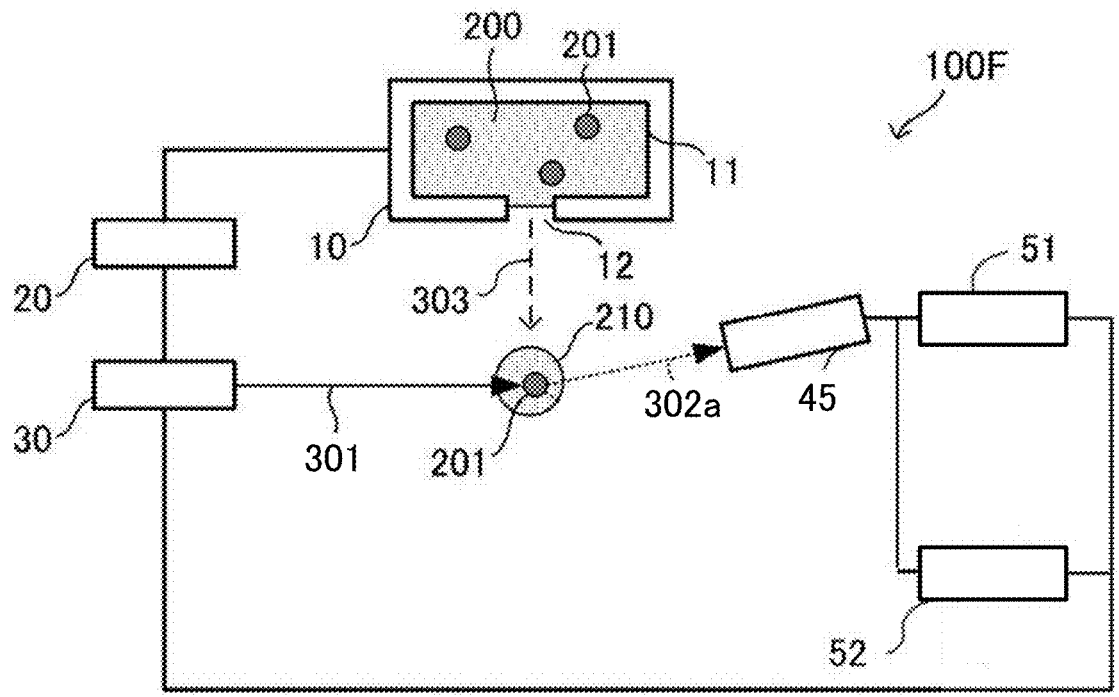
FIG. 14 is a schematic diagram of a particle counting apparatus according to a sixth embodiment.

FIG. 14 is a schematic diagram of a particle counting apparatus according to a sixth embodiment. The particle counting apparatus according to the sixth embodiment illustrated in FIG. 14 has a similar configuration to the particle counting apparatus according to the first embodiment illustrated in FIG. 1, but is different in that a single light receiver outputs information on the amount of emitted light to the first particle measuring device and the second particle measuring device. Referring to FIG. 14, a particle counting apparatus 100F includes a droplet discharger 10 equipped with a liquid chamber 11 and a nozzle 12, a driver 20, a light irradiator 30, a light receiver 45, a first particle measuring device 51, and a second particle measuring device 52. A particle suspension 200 contains fluorescent particles 201. A droplet 210 is discharged from the nozzle 12 of the droplet discharger 10 in a discharge direction 303. Laser beam 301 is emitted by the light irradiator 30. Light beam 302a is received by the light receiver 45.

In the particle counting apparatus according to the sixth embodiment, the light emission amount acquisition unit of the first particle measuring device acquires information on the amount of light emitted by the particles based on two-dimensional image information acquired by the two-dimensional image acquisition unit of the second particle measuring device.

Hereinafter, with regard to the sixth embodiment illustrated in FIG. 14, a description for the same configuration as that in FIG. 1 will be partially omitted. As illustrated in FIG. 14, the light receiver 45 is electrically coupled to the driver 20 via the light irradiator 30. The driver 20 inputs a synchronization signal to the light receiver 45. As the synchronization signal is input to the light receiver 45, the light receiver 45 receives the light beam 302$a$ in synchronization with light emission of the fluorescent particle 201 irradiated with the laser beam 301 emitted by the light irradiator 30.

The light receiver 45 is a light sensing device/module capable of measuring the presence or absence of the fluorescent particle 201 contained in the droplet 210. At the same time, the light receiver 45 is a light sensing device/module capable of measuring the number of the fluorescent particle 201 contained in the droplet 210. The light receiver 45 outputs light receiving information to the first particle measuring device 51 and the second particle measuring device 52 that are respectively electrically coupled thereto. Based on the information output from the light receiver 45, the first particle measuring device 51 measures the presence or absence of the fluorescent particle 201 contained in the droplet 210, and the second particle measuring device 52 measures the number of the fluorescent particle 201 contained in the droplet 210.

The light receiver 45 needs to measure the number of the fluorescent particle 201 in cooperation with the second particle measuring device 52. This measurement is a quantitative measurement that provides a higher degree of accuracy compared to the qualitative measurement also performed by the light receiver 45. Thus, a light sensing device/unit which acquires a large amount of information is sufficient for the required specification for the light receiver 45. The second particle measuring device 52 is capable of processing more complicated information compared to the first particle measuring device 51. In the present embodiment, the light receiver 45 capable of performing a quantitative measurement by outputting a large amount of information to the second particle measuring device 52 is also utilized as a light receiver for outputting information to the first particle measuring device 51 by reducing the amount of the information.

The operation of the particle counting apparatus of the present embodiment illustrated in FIG. 14 is described below. In a case in which a high-resolution 16-bit CMOS is used for the light receiver 45, a large amount of information, specifically, 8 MB of image information of 2,048 pixels×2,048 pixels=about 4 million pixels can be acquired. In order to output this image information to the first particle measuring device or the second particle measuring device at 100 Hz, a high-speed transmission speed of 800 MB/s=6.4 GB/s is necessary, which can be achieved by using a camera link. A transmission at 100 Hz can be performed by, for example, pco. edge 5.5 (manufactured by Tokyo Instruments, Inc.), C11440 (ORCA-Flash V2, manufactured by Hamamatsu Photonics K.K.), or C13440 (ORCA-Flash V3, manufactured by Hamamatsu Photonics K.K.). However, as it has already been explained, it is difficult for a normal PC and the like to measure the number of fluorescent particles by performing an image processing at 100 Hz on a large amount of image information. However, in some cases, a simple image processing can be performed at 100 Hz when the amount of image information has been reduced by extracting a part of image information.

The first particle measuring device 51 illustrated in FIG. 14 utilizes the above-described process. The first particle measuring device 51 having acquired a large amount of image information from the light receiver 45 can measure the presence or absence of fluorescent particle at a high speed in cooperation with the GPU by extracting only 8-bit image being a part of 16 bits/pixel constituting the image information, determining the number of pixels equal to or larger than the threshold value of the constant count value for the 8-bit image by numerical judgment of the high order bit, and setting a threshold value for the number of pixels equal to or larger than the calculated threshold value of the constant count value.

In the case of measuring the number of fluorescent particles by image processing using the second particle measuring device 52, after normal preprocessing such as median filtering, expansion/contraction processing, and binarization processing for 16-bit and about 4 million pixels, it is necessary to perform a complicated processing according to divided cases, since the light emission shape is complicated depending on the number of fluorescent particles as illustrated in FIGS. 3A and 3B. Therefore, the processing time is greatly different from that in the case of measuring the presence or absence of fluorescent particles from a part of a large amount of image information by the first particle measuring device 51.

After the first particle measuring device 51 has measured the presence or absence of the fluorescent particle at a high speed, when the fluorescent particle is absent, the processing is terminated or the droplet discharge is performed again. When the fluorescent particle is present, a large amount of information originally acquired from the light receiver 45 is transmitted to the second particle measuring device 52 or shared in a memory, so that the second particle measuring device 52 can perform an image processing. The second particle measuring device 52 thereafter performs normal preprocessing such as median filtering, expansion/contraction processing, and binarization processing for 16-bit and about 4 million pixels, and subsequently a complicated processing according to divided cases depending on the shape, thus performing a number measurement with high accuracy.

Such a configuration in which image information from a single light receiver is shared by the first particle measuring device and the second particle measuring device is effective when the average cell concentration is less than 1 cell/droplet, since the frequency with which the second particle measuring device processes is statistically smaller than the frequency with which the first particle measuring device processes. When the cell concentration is 0.2 cells/droplet or less, the frequency required for image processing by the second particle measuring device can be reduced to ⅕, that is, 20 Hz, which is preferable, and when the cell concentration is 0.1 cells/droplet or less, the frequency required for image processing by the second particle measuring device is reduced to 1/10, that is, 10 Hz, which is more preferable.

As a result, the number of parts required for the particle counting apparatus 100F can be reduced, downsizing can be achieved, the price can be reduced, and at the same time, the reliability can be improved. In addition, due to downsizing, it is possible to arrange multiple light receivers in different directions to improve accuracy.

The process of reducing a large amount of image information from the light receiver 45 and using it for the first particle measuring device is not limited to the process described above, and a process (e.g., cropping, extraction) of reducing the number of pixels by reducing the image processing area and/or a process (e.g., binning) of reducing the number of pixels by integrating a plurality of pixels can also be used. Further, the first particle measuring device 51 and the second particle measuring device 52 may be either separate devices or a single device executed by separate sequence configurations or program configurations.

Seventh Embodiment

Figure 15:
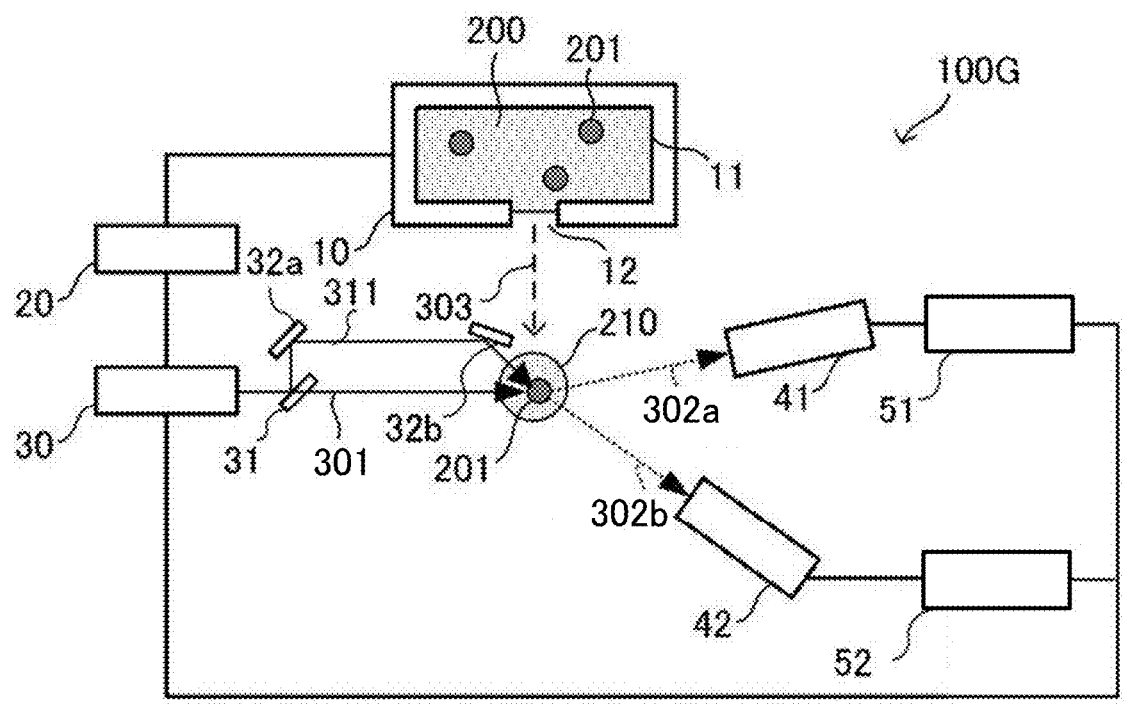
FIG. 15 is a schematic diagram of a particle counting apparatus according to a seventh embodiment.

FIG. 15 is a schematic diagram of a particle counting apparatus according to a seventh embodiment. The particle counting apparatus according to the seventh embodiment illustrated in FIG. 15 has a similar configuration to the particle counting apparatus according to the first embodiment illustrated in FIG. 1, but is different in that the light irradiator emits light beams from two or more different directions. Referring to FIG. 15, a particle counting apparatus 100G includes a droplet discharger 10 equipped with a liquid chamber 11 and a nozzle 12, a driver 20, a light irradiator 30, a beam splitter 31, deflectors 32a and 32b, light receivers 41 and 42, a first particle measuring device 51, and a second particle measuring device 52. A particle suspension 200 contains fluorescent particles 201. A droplet 210 is discharged from the nozzle 12 of the droplet discharger 10 in a discharge direction 303. Laser beams 301 and 311 are emitted by the light irradiator 30. Light beam 302a is received by the light receiver 41. Light beam 302b is received by the light receiver 42.

Hereinafter, with regard to the seventh embodiment illustrated in FIG. 15, a description for the same configuration as that in FIG. 1 will be partially omitted. As illustrated in FIG. 15, the droplet discharger 10 stores the particle suspension 200 in which the fluorescent particles 201 are suspended in the liquid chamber 11. As a piezoelectric element disposed in the liquid chamber 11 deforms, the droplet 210 in a spherical, ellipsoidal, or slightly-deformed spherical or ellipsoidal shape and containing the fluorescent particle 201 is discharged in the discharge direction 303.

The light irradiator 30 irradiates droplets discharged from the droplet discharger 10 with light. The light irradiator 30 is electrically coupled to the driver 20. The driver 20 inputs a synchronization signal to the light irradiator 30. As the synchronization signal is input to the light irradiator 30, the light irradiator 30 irradiates the droplet 210 with the laser beams 301 and 311, serving as illumination light, in synchronization with a discharge of the droplet 210 by the droplet discharger 10.

Both the light receivers 41 and 42 are electrically coupled to the driver 20 via the light irradiator 30. The driver 20 inputs a synchronization signal to the light receivers 41 and 42. As the synchronization signal is input to the light receivers 41 and 42, the light receivers 41 and 42 receive the light beam 302a and the light beam 302b, respectively, in synchronization with light emission of the fluorescent particle 201 irradiated with the laser beams 301 and 311 emitted by the light irradiator 30.

The light receiver 41 is a light sensing device/module capable of measuring the presence or absence of the fluorescent particle 201 contained in the droplet 210. The light receiver 42 is a light sensing device/module capable of measuring the number of the fluorescent particle 201 contained in the droplet 210. The light receiver 41 and the light receiver 42 output light receiving information to the first particle measuring device 51 and the second particle measuring device 52, respectively, that are respectively electrically coupled thereto. Based on the information output from the light receivers 41 and 42, the first particle measuring device 51 measures the presence or absence of the fluorescent particle 201 contained in the droplet 210, and the second particle measuring device 52 measures the number of the fluorescent particle 201 contained in the droplet 210.

The light receiver 42 measures the number of the fluorescent particle 201 in cooperation with the second particle measuring device 52. This measurement is a quantitative measurement that provides a higher degree of accuracy compared to the qualitative measurement performed by the light receiver 41. Thus, the light receiver 42 is a light sensing device/unit which acquires a larger amount of information compared to the light receiver 41 and the second particle measuring device 52 is capable of processing more complicated information compared to the first particle measuring device 51.

As the second particle measuring device 52, a personal computer (PC) or image processing software installed in PC may be used. A large amount of image information output from the two-dimensional light receiving sensor/module may be input to a memory of PC at a high speed via an input-output interface for PC.

The beam splitter 31 and the deflectors 32a and 32b each constitute a part of the light irradiator 30 that irradiates the droplet 210 with laser beam. The beam splitter 31 splits the irradiation light such that the light amount of each split light becomes one-half. One of the split light that is a rectilinear component illuminates the droplet 210 as an illumination light composed of the laser beam 301 and causes the fluorescent particles 201 contained in the droplet 210 to emit light. The other one of the split light that is a deflected component is deflected again by the deflector 32a and again by the deflector 32b and then illuminates the droplet 210 as an illumination light composed of the laser beam 311. The illumination light composed of the laser beam 311 has an angle of 45 degrees with respect to the laser beam 301 serving as the rectilinear component of the light split by the beam splitter 31. The deflectors 32a and 32b are capable of performing laser beam propagation with almost no loss of illumination light amount when they are made of a multilayer mirror having a reflectance of 99.9% that has been optimized for the wavelength of the laser beam 311, for example, 532 nm in the present embodiment.

In the particle counting apparatus 100G illustrated in FIG. 15, the frequency with which the amount of light illuminating the fluorescent particles 201 contained in the droplet 210 becomes extremely small although the original amount of emitted laser beam is the same can be more reduced compared to the case of the first embodiment illustrated in FIG. 1 in which the illumination light is composed only of the laser beam 301, thus improving the measurement accuracy. When the illumination light is composed only of the laser beam 301, the reason why the amount of light illuminating the fluorescent particles 201 contained in the droplet 210 becomes very small is due to the lens action of the droplet. Since the droplet 210 is composed mainly of water having a refractive index n of 1.333 and has a very small curvature due to its diameter of about 40 to 100 µm, a condensing power is generated due to the lens action of the droplet. As a result, the amount of illumination light relatively increases in the vicinity of the optical axis passing through the center of the cross section of the droplet 210, but the amount of illumination light relatively decreases accordingly in the region apart from the optical axis.

Figure 16:
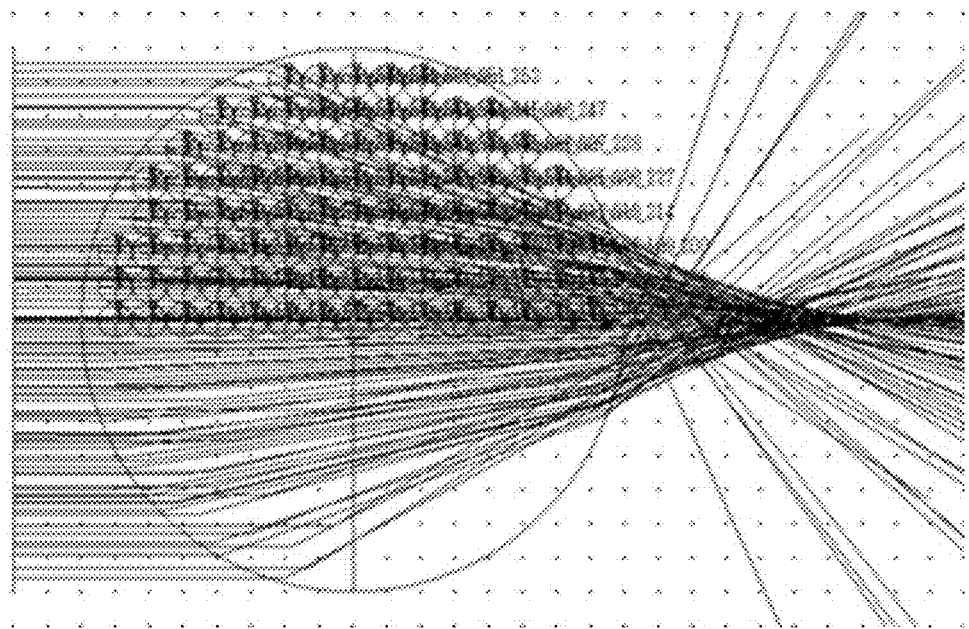
FIG. 16 is a diagram illustrating an illumination state of the particle counting apparatus according to the first embodiment in which the illumination light is composed only of a laser beam 301.

FIG. 16 is a schematic diagram illustrating an illumination state of the fluorescent particle 201 by the laser beam 301 in the embodiment illustrated in FIG. 1 in which the illumination light is composed only of the laser beam 301, obtained by an optical simulation, explaining that the amount of light illuminating the fluorescent particle 201 contained in the droplet 210 has large variations depending on the position of the fluorescent particle 201 in the droplet 210.

The optical simulation was conducted as follows. The optical simulation was conducted by a PC using an optical simulation tool LightTools 8.4.0 (manufactured by Cybernet Systems Co., Ltd.). In an optical model, it is assumed that the diameter of the droplet 210 is 80 µm, the diameter of the fluorescent particle 201 is 5 µm, the refractive index of water constituting the droplet is 1.333; and the fluorescent particles 201 contained in the droplet 210 are all located at coordinate positions within the droplet 210 at a pitch of 5 μm around the origin, when the center of the cross section of the droplet 210 is taken as the origin of the zy axis, the horizontal z axis (unit: μm) represents the optical axis direction, and the vertical y axis (unit: μm) represents the image height direction. Since the fluorescent particles 201 in the droplet 210 are rotationally symmetric about the z axis with respect to the illumination light, only the case in which the y axis is zero or above is illustrated. The laser beam 301 is a parallel light flux having a uniform illumination light amount distribution that propagates from the negative side to the positive side on the z axis, that is, from the left side to the right side in FIG. 16. The actual calculation was preformed with the number of light beams being 10 million or more. FIG. 16 illustrates only a part of the light beams in order to present an example of the illumination state by light beams as a result of ray tracing. The portion where light beams are dense represents a portion with a large amount of illumination light per unit area. The optical model is a three-dimensional (3D) model. FIG. 16 is a diagram viewed from the front surface side of the paper on which FIG. 16 is drawn in the x-axis direction, illustrating cross-sections of the droplet 210 and the fluorescent particles 201 at x=0 and projections of the light beams on the cross-sections.

As illustrated in FIG. 16, even when the illumination light has a uniform illumination light amount distribution, in a positive-side region on the z axis, i.e., in a travel-direction-side of the illumination light within the droplet 210, that is, on the right side in FIG. 16, there are a portion where the illumination light is concentrated due to the lens action of the droplet 210 to increase the amount of illumination light per unit area and another portion where the amount of illumination light per unit area is decreased. There is a region where no light beam exists in the portion where the amount of illumination light per unit area is small. Assuming that the number of light beams illustrated in FIG. 16 is 10 million levels, the region where no light beam exists has a small area but reliably exists in the upper right and lower right of the liquid droplet 210. From this, it can be seen that there are areas not illuminated by a parallel light flux from one direction or areas where the amount of illumination light is very small. The amount of light emitted from the fluorescent particles existing in such regions is zero or very small. In this case, the light receivers 41 and 42 are required to have a very high sensitivity. When the amount of illuminating light is zero and the amount of emitted light is zero, the presence or absence or the number of the fluorescent particles cannot be determined by any types of the light receivers 41 and 42. Therefore, there is a problem that the measurement accuracy deteriorates based on the frequency at which the fluorescent particles 201 in the droplet 210 are located in these areas. The particle counting apparatus according to the seventh embodiment illustrated in FIG. 15 solves this problem.

By changing the illumination light from the parallel light flux to an illumination light having an illumination angle described by the numerical aperture (NA), it is possible to reduce the region that is not illuminated or where the illumination light amount is very small. For example, in order to eliminate the region that is not illuminated from the droplet 210 containing water as a main component, it is necessary to set NA to 0.4 or more and to use an illumination or laser beam using a halogen lamp or a xenon lamp by a condenser lens of microscope, a diffuser, and a condenser lens having a high NA such as an objective lens of microscope. However, each of these is large in size and it is difficult to adjust their positions in the optical system. Another problem is that the amount of illuminating light per unit area decreases. Therefore, it is difficult to use such an illumination light for the purposed of the present embodiment.

FIGS. 17A, 17B, and 17C are diagrams each illustrating an illumination light amount distribution of the fluorescent particles 201 contained in the droplet 210, obtained by an optical simulation, for quantitatively explaining the effect of the particle counting apparatus according to the seventh embodiment illustrated in FIG. 15. FIG. 17A represents a case of the first embodiment illustrated in FIG. 1 in which the illumination light is the laser beam 301 emitted by the light irradiator 30. FIG. 17B represents a case of the seventh embodiment illustrated in FIG. 15 in which the illumination light is only the laser beam 311 emitted from the light irradiator 30 incident at 45 degrees to the z axis. In FIG. 17B, the total amount of illumination light is doubled to be the same as that in FIG. 17A for comparison with FIG. 17A. FIG. 17C represents a case of the seventh embodiment illustrated in FIG. 15 in which the laser beam 301 and the laser beam 311 are combined as the illumination light. In each of FIGS. 17A, 17B, and 17C, the center of the cross section of the droplet 210 is taken as the origin of the zy axis, the horizontal z axis (unit: μm) represents the optical axis direction in which the right side of the drawing is positive, and the vertical y axis (unit: μm) represents the image height direction in which the upper side of the drawings is positive.

FIGS. 17A and 17C were obtained using an optical model in which the center positions of the fluorescent particles 201 in the droplet 210 illustrated in FIG. 16 were allocated at a pitch of 5 μm around the origin. The amount of light received at each position of the fluorescent particle 201 when the fluorescent particles 201 is illuminated with an illumination light composed of laser beam was calculated. Since the fluorescent particles serve as omnidirectional divergent light sources, the calculation was performed while setting the number of light beams to 10 million lines or more, thus ensuring necessary accuracy for each fluorescent particle. For comparison, the distribution illustrated in FIG. 17A has been normalized such that the amount of light received at the position (z, y)=(−35, 0) on the left end of the droplet 210 on the side where the laser beam 301 is incident at zero degrees that is parallel with the optical axis, where the lens action of the droplet is relatively small, is 1.0. FIG. 17B was obtained based on FIG. 17A by rotating the coordinate axis by 45 degrees and then performing interpolation calculation for each coordinate of the fluorescent particle having a pitch of 5 μm around the origin.

As illustrated in FIG. 17A, as the position of the fluorescent particle 201 comes closer to the right end of the droplet 210 opposite to the side where the laser beam 301 is incident on the optical axis, the amount of received light is increased up to 6.7 times compared to that on the left end where the lens action is small. As the droplet 210 acts as a convex lens, light is focused in the vicinity of the optical axis and, at the same time, a large aberration is generated due to a very strong curvature. As a combined result, the amount of received light becomes maximum at the positions of (z, y)=(30, −15) and (30, 15) that are close to the light collecting surface and near the optical axis but not on the optical axis. On the other hand, there is a region where the illumination light decreases as a trade-off with formation of the region where the illumination light is focused. Such a region include the positions where y=−35, −30, 30, and 35, and (z, y)=(25, −25), (30, −20), (25, 25), and (30, 20) that are on the periphery of the droplet 210 with respect to the optical axis. The regions where y=−35, −30, 30, and 35 are illustrated by a cross-section as a two-dimensional (2D) distribution in FIG. 17A. In an actual three-dimensional (3D) distribution, the proportion of the fluorescent particles 201 in this region increases. In addition, the amount of illumination light is zero for 10 fluorescent particles at the respective positions (z, y)=(25, −25), (30, −20), (25, 25), (30, 20), (15, −30), (20, −30), (15, 30), (20, 30), (10, 35), and (10, −35). It is a problem that the particle measurement cannot be performed at a frequency of the presence of fluorescent particles at these positions.

FIG. 17B represents a case of the seventh embodiment illustrated in FIG. 15 in which the laser beam 311 emitted by the light irradiator 30 is incident only at 45 degrees with respect to the z axis. Similar to FIG. 17A, it can be seen in FIG. 17B that there are fluorescent particles which are not illuminated or fluorescent particles illuminated with a very small amount of light depending on the position of the fluorescent particles 211 in the droplet 210, although there is a positional difference from FIG. 17A since FIG. 17B is obtained by rotating FIG. 17A by 45 degrees.

It is to be noted that the reason why the number of the positions of fluorescent particles where the amount of received light is zero is more reduced in FIG. 17B compared to FIG. 17A is that calculation accuracy is relatively decreased since FIG. 17B is obtained by interpolation calculation based on the result of FIG. 17A. In each of FIGS. 17A and 17B, the illumination light is a parallel light flux in one direction in the same level of illumination state. It is a problem that there are 10 fluorescence positions where the amount of received light is 0 to 0.2.

FIG. 17C represents a case of the seventh embodiment illustrated in FIG. 15 in which the laser beam 301 and the laser beam 311 both emitted from the light irradiator 30 are combined. In this embodiment, although the total amount of received light is the same, the number of positions where fluorescent particles are not illuminated or where fluorescent particles are illuminated with a very small amount of illumination light is decreased. This is because, since the droplet 210 is irradiated from two different directions, the influence of the condensing action due to the lens action of the droplet 210 is divided into two, and the amount of illumination light is increased by extreme focusing, and at the same time, reduction of the amount of illumination light is decreased as a trade-off. At this time, the frequency with which fluorescent particles are illuminated with an extremely small amount of illumination light is decreased and the accuracy of particle measurement can be improved. Thus, the particle counting apparatus 100G can provide higher measurement accuracy.

In FIG. 15, the angle between the laser beams 301 and 311, serving as the illumination light to irradiate the droplet particles 210 from different directions, is not limited to 45 degrees. In addition, the number of laser beams serving as illuminations to irradiate the droplet particles 210 from different directions is not limited to two as illustrated in FIG. 15. As the number is increased to 3, 4, or more, the influence of the lens action of the droplet is divided, which is more effective. These conditions are optimized in consideration of required accuracy, layout of the optical system, cost, and the like. It is also effective to increase the illuminating directions of the illumination light by using a micro optical element in the vicinity of the droplet discharger 10.

The particle counting apparatus according to the seventh embodiment illustrated in FIG. 15 includes: a droplet discharger configured to discharge a droplet containing a luminescent particle capable of emitting light upon receiving light; a light irradiator configured to irradiate the droplet discharged by the droplet discharger with light; a light receiver configured to receive light emitted by the luminescent particle irradiated with the light emitted by the light irradiator; and a particle counter configured to count the luminescent particle contained in the droplet based on the light received by the light receiver, including a first particle measuring device configured to measure a presence or absence of the luminescent particle contained in the droplet and a second particle measuring device configured to measure the number of the luminescent particle contained in the droplet. However, the effect of the seventh embodiment can be exerted even without the first particle measuring device and/or the second particle measuring device.

This is because the seventh embodiment illustrated in FIG. 15, in which the droplet containing the luminescent particle is irradiated with illumination light from two or more directions and therefore the frequency with which the amount of illumination light is decreased depending on the position of the luminescent particle is reduced, is effective for both for the first particle measuring device that measures the presence or absence of the luminescent particle contained in the droplet and the second particle measuring device that measures the number of the luminescent particles contained in the droplet. Therefore, the seventh embodiment is effective not only for the first embodiment illustrated in FIG. 1 in which the first particle measuring device and the second particle measuring device are combined but for the particle counting apparatus provided with only the first particle measuring device or the second particle measuring device.

Figure 18:
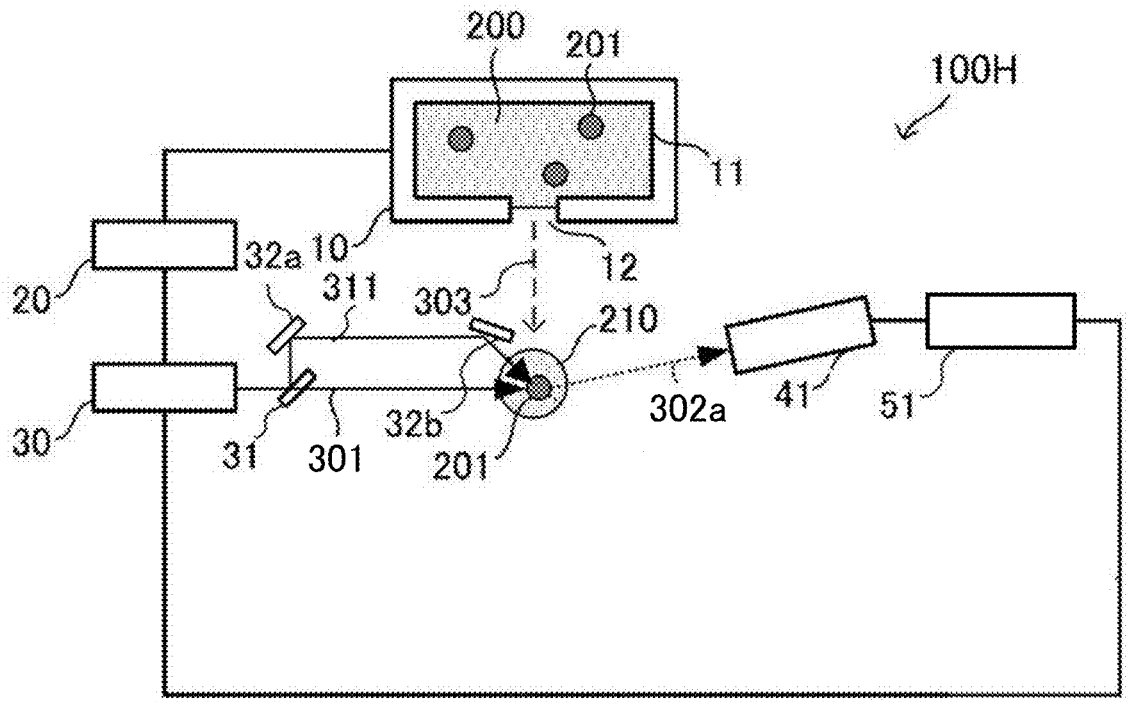
FIG. 18 is a reference diagram illustrating a particle counting apparatus provided only with a first particle measuring device.

FIG. 18 is a schematic diagram illustrating a particle counting apparatus 100H provided with only the first particle measuring device. Hereinafter, with regard to the embodiment illustrated in FIG. 18, a description for the same configuration as that in FIG. 15 will be partially omitted. As illustrated in FIG. 18, the light irradiator 30 irradiates droplets discharged from the droplet discharger 10 with light. The light irradiator 30 is electrically coupled to the driver 20. The driver 20 inputs a synchronization signal to the light irradiator 30. As the synchronization signal is input to the light irradiator 30, the light irradiator 30 irradiates the droplet 210 with the laser beams 301 and 311, serving as illumination light, in synchronization with a discharge of the droplet 210 by the droplet discharger 10.

The single light receiver 41 is electrically coupled to the driver 20 via the light irradiator 30. The driver 20 inputs a synchronization signal to the light receiver 41. As the synchronization signal is input to the light receiver 41, the light receiver 41 receives the light beam 302a in synchronization with light emission of the fluorescent particle 201 irradiated with the laser beams 301 and 311 emitted by the light irradiator 30.

The light receiver 41 is a light sensing device/module capable of measuring the presence or absence of the fluorescent particle 201 contained in the droplet 210. The light receiver 41 outputs light receiving information to the first particle measuring device 51 that is electrically coupled thereto. Based on the information output from the light receiver 41, the first particle measuring device 51 measures the presence or absence of the fluorescent particle 201 contained in the droplet 210.

Similar to the seventh embodiment illustrated in FIG. 15, the beam splitter 31 and the deflectors 32a and 32b each constitute a part of the light irradiator 30 that irradiates the droplet 210 with laser beam. The beam splitter 31 splits the irradiation light such that the light amount of each split light becomes one-half. One of the split light that is a rectilinear component illuminates the droplet 210 as an illumination light composed of the laser beam 301 and causes the fluorescent particles 201 contained in the droplet 210 to emit light. The other one of the split light that is a deflected component is deflected again by the deflector 32*a* and again by the deflector 32*b* and then illuminates the droplet 210 as an illumination light composed of the laser beam 311. The illumination light composed of the laser beam 311 has an angle of 45 degrees with respect to the laser beam 301 serving as the rectilinear component of the light split by the beam splitter 31. The deflectors 32*a* and 32*b* are capable of performing laser beam propagation with almost no loss of illumination light amount when they are made of a multi-layer mirror having a reflectance of 99.9% that has been optimized for the wavelength of the laser beam 311, for example, 532 nm in the present embodiment.

In the particle counting apparatus 100H illustrated in FIG. 18, the frequency with which the amount of light illuminating the fluorescent particles 201 contained in the droplet 210 becomes extremely small although the original amount of emitted laser beam is the same can be more reduced compared to the case of the first embodiment illustrated in FIG. 1 in which the illumination light is composed only of the laser beam 301, thus improving the measurement accuracy. When the illumination light is composed only of the laser beam 301, the reason why the amount of light illuminating the fluorescent particles 201 contained in the droplet 210 becomes very small is due to the lens action of the droplet. Since the droplet 210 is composed mainly of water having a refractive index n of 1.333 and has a very small curvature due to its diameter of about 40 to 100 μm, a condensing power is generated due to the lens action of the droplet. As a result, the amount of illumination light relatively increases in the vicinity of the optical axis passing through the center of the cross section of the droplet 210, but the amount of illumination light relatively decreases accordingly in the region apart from the optical axis.

The embodiment illustrated in FIG. 18 is effective in a case in which the above-described condensing power due to the lens action of the droplet is generated. The configuration and operation thereof are completely different from those of a measuring apparatus for measuring fluorescent particles or cells present in a flow channel filled with liquid, such as such as flow cytometry, and are peculiar for measuring fluorescent particles or cells present in the discharged droplets.

The particle counting apparatus according to the seventh embodiment illustrated in FIG. 15 includes: a droplet discharger configured to discharge a droplet containing a luminescent particle capable of emitting light upon receiving light; a light irradiator configured to irradiate the droplet discharged by the droplet discharger with light; a light receiver configured to receive light emitted by the luminescent particle irradiated with the light emitted by the light irradiator; and a particle counter configured to count the luminescent particle contained in the droplet based on the light received by the light receiver, wherein the light irradiator emits light beams from two or more different directions.

Here, in the particle counting apparatus 100G according the seventh embodiment illustrated in FIG. 15, similarly to the first embodiment illustrated in FIG. 1, at least two (multiple) light receivers, i.e., the light receiver 41 that outputs information to the first particle measuring device 51 and the light receiver 42 that outputs information to the second particle measuring device 52, are combined. It is preferable that the droplet 210 discharged from the droplet discharger 10 is measured in the vicinity of the nozzle 12 of the droplet discharger 10, for example, at a position 0.5 to 1 mm away from the nozzle 12. In this case, it is necessary that the light receivers 41 and 42 are compact in size. By using compact light receivers in the present embodiment, even when the light use efficiency of the optical element of the light receivers or the photoelectric conversion efficiency of the light receiving element of the light receivers are decreased, it is possible to increase the amount of illumination light and compensate the decrease in efficiency due to miniaturization of the light receivers, which is preferable.

Eighth Embodiment

Figure 19:
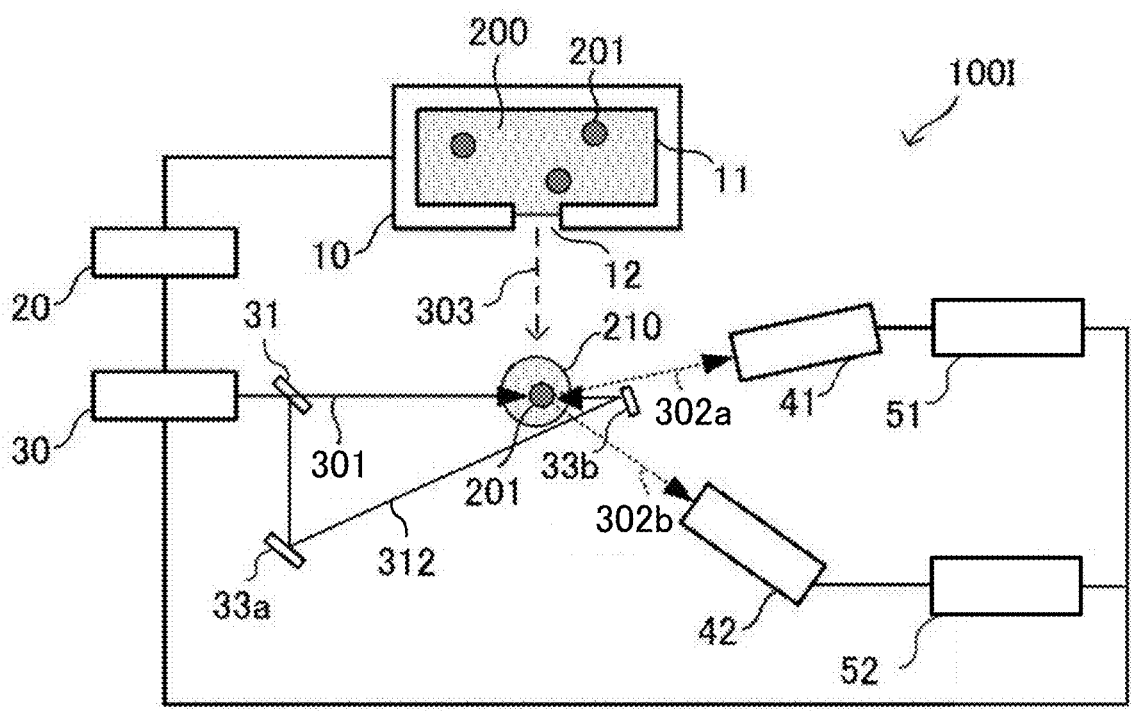
FIG. 19 is a schematic diagram of a particle counting apparatus according to an eighth embodiment.

FIG. 19 is a schematic diagram of a particle counting apparatus according to an eighth embodiment. The particle counting apparatus according to the eighth embodiment illustrated in FIG. 19 has a similar configuration to the particle counting apparatus according to the seventh embodiment illustrated in FIG. 15, but is different in that the light irradiator emits light from two or more different directions that are substantially opposite directions. Referring to FIG. 19, a particle counting apparatus 100I includes a droplet discharger 10 equipped with a liquid chamber 11 and a nozzle 12, a driver 20, a light irradiator 30, a beam splitter 31, deflectors 33*a* and 33*b*, light receivers 41 and 42, a first particle measuring device 51, and a second particle measuring device 52. A particle suspension 200 contains fluorescent particles 201. A droplet 210 is discharged from the nozzle 12 of the droplet discharger 10 in a discharge direction 303. Laser beams 301 and 312 are emitted by the light irradiator 30. Light beam 302*a* is received by the light receiver 41. Light beam 302*b* is received by the light receiver 42.

Hereinafter, with regard to the seventh embodiment illustrated in FIG. 19, a description for the same configuration as that in FIG. 15 will be partially omitted. As illustrated in FIG. 19, the light irradiator 30 irradiates droplets discharged from the droplet discharger 10 with light. The light irradiator 30 is electrically coupled to the driver 20. The driver 20 inputs a synchronization signal to the light irradiator 30. As the synchronization signal is input to the light irradiator 30, the light irradiator 30 irradiates the droplet 210 with the laser beams 301 and 312, serving as illumination light, in synchronization with a discharge of the droplet 210 by the droplet discharger 10.

The beam splitter 31 and the deflectors 33*a* and 33*b* each constitute a part of the light irradiator 30 that irradiates the droplet 210 with laser beam. The beam splitter 31 splits the irradiation light such that the light amount of each split light becomes one-half. One of the split light that is a rectilinear component illuminates the droplet 210 as an illumination light composed of the laser beam 301 and causes the fluorescent particles 201 contained in the droplet 210 to emit light. The other one of the split light that is a deflected component is deflected again by the deflector 33*a* and again by the deflector 33*b* and then illuminates the droplet 210 as an illumination light composed of the laser beam 311. The illumination light composed of the laser beam 312 has an angle of 180 degrees with respect to the laser beam 301 serving as the rectilinear component of the light split by the beam splitter 31. That is, the laser beam 312 and the laser beam 301 are opposed to each other.

In the particle counting apparatus 100I illustrated in FIG. 19, the frequency with which the amount of light illuminating the fluorescent particles 201 contained in the droplet 210 becomes extremely small although the original amount of emitted laser beam is the same can be more reduced compared to the case of the seventh embodiment illustrated in FIG. 15 in which the laser beam 301 and the laser beam 311 are emitted from two different directions forming an angle of 45 degrees therebetween, thus improving the measurement accuracy.

Figures 20, 21:
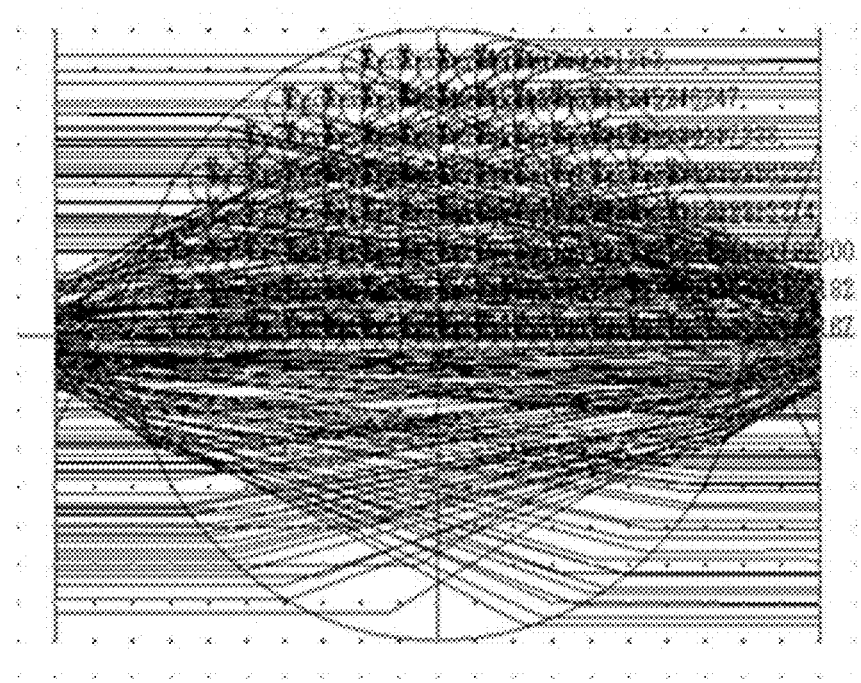
FIG. 20 is a diagram illustrating an illumination state of the particle counting apparatus according to the eighth embodiment.
FIG. 21 is a diagram illustrating a distribution of the amount of illumination light in the particle counting apparatus according to a ninth embodiment.

FIG. 20 is a schematic diagram obtained by an optical simulation for qualitatively explaining the reason for the above-described phenomenon. Specifically, FIG. 20 is a schematic diagram illustrating an illumination state of the fluorescent particle 201 by the laser beams 301 and 312 in the eighth embodiment illustrated in FIG. 19 in which the laser beam 301 and the laser beam 312 are emitted from two different directions forming an angle of 180 degrees therebetween, explaining that the amount of light illuminating the fluorescent particle 201 contained in the droplet 210 has large variations depending on the position of the fluorescent particle 201 in the droplet 210.

The optical simulation was conducted based on an optical model and conditions described below. The conditions were basically the same as those in the seventh embodiment illustrated in FIG. 16 and FIGS. 17A and 17B. The laser beam 301 is a parallel light flux having a uniform illumination light amount distribution that propagates from the negative side to the positive side on the z axis, that is, from the left side to the right side in FIG. 20. The laser beam 312 is a parallel light flux having a uniform illumination light amount distribution, the propagation direction of which is different from that of the laser beam 301 by 180 degrees, i.e., the laser beam 312 propagates from the positive to the negative side of the z axis, that is, from the right side to the left side in FIG. 20. The actual calculation was preformed with the number of light beams being 20 million or more. FIG. 20 illustrates only a part of the light beams in order to present an example of the illumination state by light beams as a result of ray tracing. The portion where light beams are dense represents a portion with a large amount of illumination light per unit area.

As illustrated in FIG. 20, in both the laser beam 301 and the laser beam 312, there are a portion where the illumination light is concentrated due to the lens action of the droplet 210 to increase the amount of illumination light per unit area and another portion where the amount of illumination light per unit area is decreased. In the hemisphere in which the one of the illumination light beams exit, there is a region where one of the illumination light beams does not propagate due to the lens action of the droplet 210. However, the other one of the illumination light beams propagates almost throughout that region, since the region is in the hemisphere in which the other one of the illumination light beams is incident. This means that irregularities in illumination light amount distribution are interpolated in units of hemisphere by illumination light beams emitted from two different angles which are substantially opposite directions. As a result, in the interior of the droplet 210, the non-illuminated region is eliminated and the region where the illumination light amount is very small is reduced. It is possible to illuminate the spherical surface like a moon all with illumination light consisting of parallel light fluxes forming an angle of 180 degrees therebetween. Similarly, the interior of the sphere can be illuminated with illumination light consisting of parallel light fluxes forming an angle of 180 degrees therebetween. Assuming that the number of light beams illustrated in FIG. 20 is 20 million levels, it can be visually confirmed that the region where no light beam exists is eliminated. On the other hand, it is necessary that the region where the amount of illumination light is small is quantitatively compared.

FIG. 21 is a diagram illustrating an illumination light amount distribution of the fluorescent particles 201 contained in the droplet 210, obtained by an optical simulation, for quantitatively explaining the effect of the particle counting apparatus according to the eighth embodiment illustrated in FIG. 19 in which the light irradiator 30 combines the laser beam 301 and the laser beam 312. In FIG. 21, the center of the cross section of the droplet 210 is taken as the origin of the zy axis, the horizontal z axis (unit: μm) represents the optical axis direction in which the right side of the drawing is positive, and the vertical y axis (unit: μm) represents the image height direction in which the upper side of the drawings is positive. FIG. 21 was obtained using an optical model in which the center positions of the fluorescent particles 201 in the droplet 210 were allocated at a pitch of 5 μm around the origin. The amount of light received at each position of the fluorescent particle 201 when the fluorescent particles 201 is illuminated with an illumination light composed of laser beam was calculated. Since the fluorescent particles serve as omnidirectional divergent light sources, the calculation was performed while setting the number of light beams to 20 million lines or more, thus ensuring necessary accuracy for each fluorescent particle. For comparison, the distribution has been normalized such that the amount of light received at the position (z, y)=(−35, 0) in the embodiment illustrated in FIG. 17A on the left end of the droplet 210 on the side where the laser beam 301 is incident at zero degrees that is parallel with the optical axis, where the lens action of the droplet is relatively small, is 1.0. Therefore, the amount of light illuminating the fluorescent particle 201 at each position can be directly compared with those in FIGS. 17A, 17B, and 17C.

As illustrated in FIG. 21, there is no position where the amount of light illuminating the fluorescent particle 201 is zero in the droplet 210. Therefore, the particle counting apparatus 100I according to the eighth embodiment illustrated in FIG. 21 performs, in principle, a measurement without defective detection when the amplification sensitivity of the light receiver is sufficiently increased. Although the amount of light illuminating the fluorescent particle 201 decreases as the position of the fluorescent particle 201 is apart from the optical axis, the amount of illuminating light remains 0.1 to 0.2 without becoming extremely small. As a result, the amplification sensitivity of the light receiver is provided with a margin and the noise accompanying the amplification is reduced. Thus, the accuracy of the particle counting apparatus 100I has improved or will be easily improved.

Although there are a lot of the fluorescent particles 201 which are at the positions where the illumination light amount distribution has increased because parallel luminous fluxes of the illumination light are condensed due to the lens action of the droplet, the maximum value thereof is 3.9, which is one third to one half of that in the first embodiment illustrated in FIG. 17A in which the maximum value is 6.7 or the seventh embodiment illustrated in FIG. 17C in which the maximum value is 5.1. Variations in illumination light is greatly reduced in the present embodiment. Thus, when PMT is used as the light receiver or a digitizer is used as a part of the particle measuring device, the dynamic range required at the time of measurement can be reduced. In the case of using PMT, the amplification factor can be increased and the accuracy can be further improved because the risk of saturation by amplification is reduced. As the digitizer, a

Ninth Embodiment

Figures 22, 23:
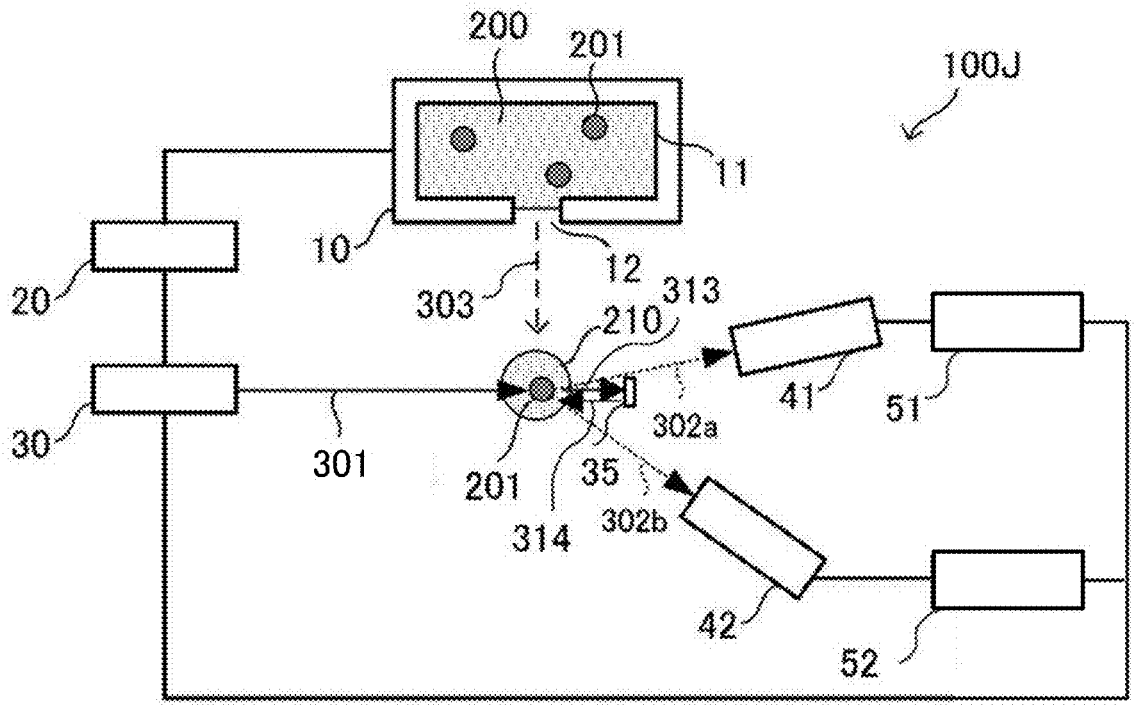
FIG. 22 is a schematic diagram of a particle counting apparatus according to the ninth embodiment.
FIG. 23 is a diagram illustrating another distribution of the amount of illumination light in the particle counting apparatus according to the ninth embodiment.

FIG. 22 is a schematic diagram of a particle counting apparatus according to a ninth embodiment. The particle counting apparatus according to the ninth embodiment illustrated in FIG. 22 has a similar configuration to the particle counting apparatus according to the eighth embodiment illustrated in FIG. 19, but is different in that the light irradiator emits light from two or more different directions that are substantially opposite directions. Referring to FIG. 22, a particle counting apparatus 100J includes a droplet discharger 10 equipped with a liquid chamber 11 and a nozzle 12, a driver 20, a light irradiator 30, a deflector 35, light receivers 41 and 42, a first particle measuring device 51, and a second particle measuring device 52. A particle suspension 200 contains fluorescent particles 201. A droplet 210 is discharged from the nozzle 12 of the droplet discharger 10 in a discharge direction 303. Laser beams 301, 313, and 314 are emitted by the light irradiator 30. Light beam 302a is received by the light receiver 41. Light beam 302b is received by the light receiver 42.

In the particle counting apparatus according to the ninth embodiment, the light irradiator that emits light beams from two or more different directions includes: a first light irradiator configured to irradiate the droplet with a substantially parallel light flux; and a second light irradiator including an optical deflector element, configured to deflect the substantially parallel light flux transmitted the droplet, in response to irradiation of the droplet with a part of the substantially parallel light flux, to irradiate the droplet again.

Hereinafter, with regard to the ninth embodiment illustrated in FIG. 22, a description for the same configuration as that in FIG. 19 will be partially omitted. As illustrated in FIG. 22, the light irradiator 30 irradiates droplets discharged from the droplet discharger 10 with light. The light irradiator 30 is electrically coupled to the driver 20. The driver 20 inputs a synchronization signal to the light irradiator 30. As the synchronization signal is input to the light irradiator 30, the light irradiator 30 irradiates the droplet 210 with the laser beams 301 and 314, serving as illumination light, in synchronization with a discharge of the droplet 210 by the droplet discharger 10.

The deflector 35 constitutes a part of the light irradiator 30 (first light irradiator). The deflector 35 is disposed in such a manner that, after the light irradiator 30 irradiates the droplet 210 with the laser beam 301, the deflector 35 (second light irradiator) reflects the laser beam 313 that propagates behind the droplet 210 to deflect the laser beam 313 by 180 degrees in the propagation direction thereof. As a result, the laser beam 313 becomes a laser beam 314 propagating toward the droplet 210 again. The laser beam 314 irradiates the droplet 210 again, and furthermore, illuminates the fluorescent particles 201 existing in the droplet 210 again with illumination light from a direction different from the laser beam 301 by 180 degrees, thus greatly increasing the amount of light illuminating the fluorescent particles 201.

In the particle counting apparatus 100J illustrated in FIG. 22, the frequency with which the amount of light illuminating the fluorescent particles 201 contained in the droplet 210 becomes extremely small although the original amount of emitted laser beam is the same can be more reduced compared to the seventh embodiment illustrated in FIG. 15 in which the laser beam 301 and the laser beam 311 are emitted from two different directions forming an angle of 45 degrees therebetween and the eighth embodiment illustrated in FIG. 19 in which the laser beams are emitted from two different directions forming an angle of 180 degrees therebetween, thus improving the measurement accuracy.

In the embodiments illustrated in FIGS. 15 and 19, the laser beam 313 propagating behind the droplet 210 after the laser beam 301 has irradiated the droplet 210 and the fluorescent particle 201 contained in the droplet 210 is not utilized in the optical system of the particle counting apparatus 100J. Rather, since the laser beam 313 is possible to become noise light, the output thereof is greatly reduced by a light absorbing damper or the like provided in its propagation direction. By contrast, since this laser beam 313 is reused in the embodiment illustrated in FIG. 22, the illumination light amount becomes the same level as when using a laser beam source corresponding to twice the light output.

For example, even when the beam diameter of the laser beam 301 is set to 1 mm, which is relatively thin as a space propagation beam, the ratio of the cross-sectional area of the droplet 210 having a diameter of 80 μm to the cross-sectional area corresponding to the beam diameter is about 0.6%. Even when the droplet 210 and the fluorescent particles 201 contained in the droplet 210 absorb all the light corresponding to the diameter of 80 μm and become a loss, the loss as the illumination light is small. Also, with respect to the deflector 35, when a commercially available multilayer film mirror having a reflectance of 99.9% is used therefor, the loss as the illumination light is small. For this reason, the illumination light amount in the present embodiment illustrated in FIG. 22 can be increased about twice that in the eighth embodiment illustrated in FIG. 19.

Actually, since the diameter of the droplet 210 is as relatively small as 80 μm, the light loss due to diffraction becomes a problem. However, since the light absorption related to the droplet 210 the fluorescence emission by the droplet 210 is small, light loss due to this light absorption is small and does not become a big problem. In addition, since it is unnecessary to make the optical axis of the laser beam 301 completely coincide with that of the laser beam 314 incident on the droplet from a direction different by 180 degrees. Therefore, by adjusting the deflector 35 so that the actual optical axis slightly differs in such a manner that the position in the droplet 210 corresponding to the incidence of the laser beam 301 is displaced, it is easy to provide illumination light having substantially the same illumination light amount distribution by laser beam 314. In actual, the loss due to diffraction may not be a problem, and the amount of illumination light can be increased about twice.

FIG. 23 is a diagram illustrating an illumination light amount distribution of the fluorescent particles 201 contained in the droplet 210, obtained by an optical simulation, for quantitatively explaining the effect of the particle counting apparatus according to the ninth embodiment illustrated in FIG. 22. The coordinates and units in FIG. 23 and the conditions for the optical simulation are the same as those in FIGS. 17A, 17B, 17C, and 21. In the optical model, the deflector 35 is treated as a mirror and the reflectance thereof has been rounded beforehand to 100% in consideration of the effective digit number of the reflectance of 99.9% on a commercial product thereof. Therefore, the amount of illumination light in FIG. 23 is doubled compared to that in FIG. 21.

Similar to FIG. 21, for comparison, the distribution has been normalized such that the amount of light received at the position (z, y)=(−35, 0) in the embodiment illustrated in FIG. 17A on the left end of the droplet 210 on the side where the laser beam 301 is incident at zero degrees that is parallel with the optical axis, where the lens action of the droplet is relatively small, is 1.0. Therefore, the amount of light illuminating the fluorescent particle 201 at each position can be directly compared with those in FIGS. 17A, 17B, 17C, and 21.

In the ninth embodiment illustrated in FIG. 23, similar to the eighth embodiment illustrated in FIG. 21, there is no position where the amount of light illuminating the fluorescent particle 201 is zero in the droplet 210. Although the amount of light illuminating the fluorescent particle 201 decreases as the position of the fluorescent particle 201 is apart from the optical axis, the amount of illuminating light remains 0.6 or more, which is 60 percent that when there is little effect of the lens action of the droplet 210. As a result, the amplification sensitivity of the light receiver is provided with a margin and the noise accompanying the amplification is reduced. Thus, the accuracy of the particle counting apparatus 100J has improved or will be easily improved.

In the ninth embodiment illustrated in FIG. 23, the output of the laser beam emitted from the light irradiator 30 is the same as that in the eighth embodiment illustrated in FIG. 21. Therefore, the cost of the laser beam source can be greatly lowered, which is very effective. After the droplet 210 is firstly irradiated with laser beam, the laser beam is deflected by the deflector so that the droplet 210 is secondly irradiated with the laser beam again from a different direction. The irradiation directions in the first and second irradiations are different, and the angle formed between the different directions are not limited to approximately 180 degrees as illustrated in FIG. 23. It is preferable that the angle is optimized using a plurality of deflectors, such as to approximately 90 degrees (substantial orthogonal to each other), to approximately 45 degrees, or to approximately 30 degrees, in accordance with the layout restriction in the particle counting apparatus 100J.

Further, the number of times of irradiating the droplet 210 again with laser beam from different angles (directions) by using a plurality of deflectors is not limited to twice as illustrated in FIG. 23, and may be three times or more. In this case, it is preferable that at least two of the above three or more times of irradiation be performed from different directions that are substantially opposite to each other, thereby effectively reducing the frequency with which the amount of illumination light is decreased due to the lens action of the droplet 210 depending on the position of the fluorescent particles 201.

In the ninth embodiment illustrated in FIGS. 22 and 23, since the laser beam 313 that has been irradiated the droplet 210 is deflected by the deflector 35 and irradiates the droplet 210 again, an accurate optical system adjustment including optical axis adjustment is performed. For example, a measurement unit that measures beam profile or beam center position of the laser beam and an adjustment unit that appropriately or automatically adjusts the optical system based on the information from the measurement unit may be provided, so as to prevent reduction if the illumination light amount due to defective optical system adjustment. In the optical system adjustment, preferably, not simply the position of the optical axis is optimized, but the optical system that has been optimally designed to achieve a high light utilization efficiency, a high luminous efficiency with respect to the fluorescent particles, and a high light utilization efficiency of the light receiver, is adjusted to function as initially designed, in consideration of beam waist position and time delay of light irradiation.

In the ninth embodiment illustrated in FIGS. 22 and 23 in which the deflector 35 is provided for deflecting the laser beam 313 after irradiating the droplet 210, it is effective to optimize the light transmission spectrum of the deflector to extract a part of the laser beam 313 after irradiating the droplet 210 and provide a separate light receiver in the propagation direction of the extracted laser beam for measuring the presence or absence of the liquid droplet 210 itself. In a case in which a multilayer mirror having a reflectance of 99.9% is used as the deflector 35, even when the transmittance is about 0.01% due to the factors other than surface scattering of the mirror and light absorption inside the mirror among 0.1% of the light loss, the presence or absence of the droplet 210 itself can be measured by the separately provided light receiver since the original laser beam has a large light energy. Examples of the separately provided light receiver include, but are not limited to, CCD, CMOS, PMT, and APD.

Figure 24:
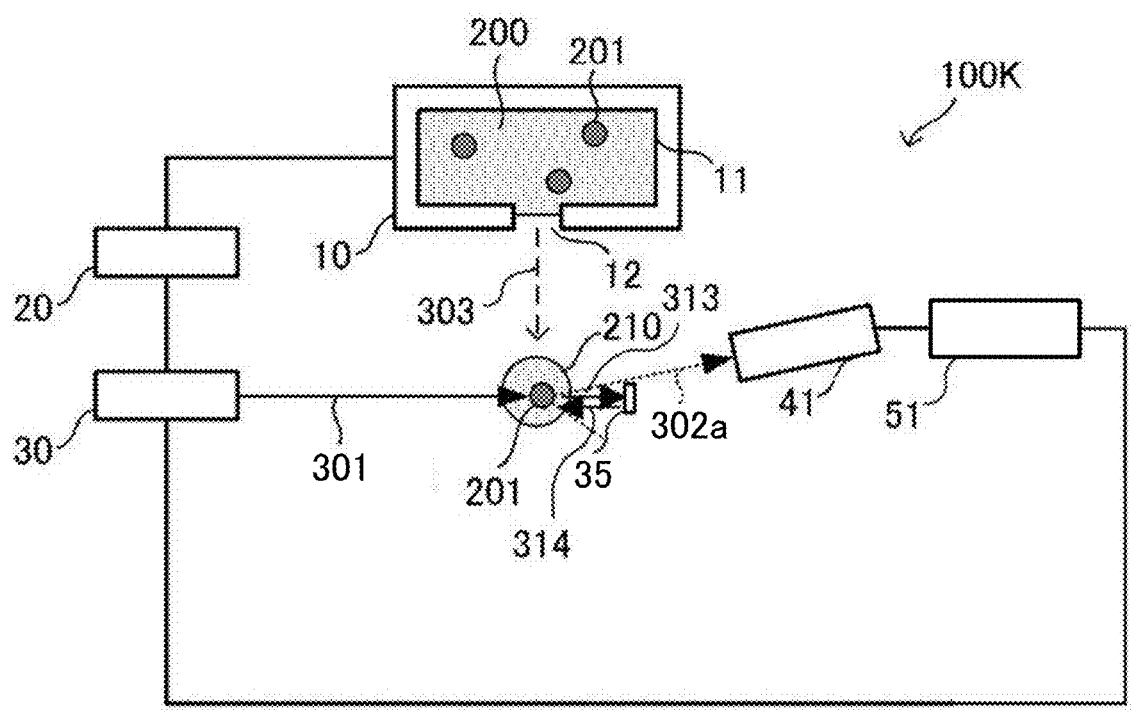
FIG. 24 is a reference diagram illustrating a particle counting apparatus provided only with a first particle measuring device.

The configuration of the ninth embodiment illustrated in FIG. 22 in which the light irradiator emits light from two or more different directions that are substantially opposite directions is effective for the particle counting apparatus 100J in which the first particle measuring device and the second particle measuring device are provided, similar to the configuration illustrated in FIG. 18 in which only the first particle measuring device 51 is provided. FIG. 24 is a schematic diagram illustrating a particle counting apparatus 100K provided with only the first particle measuring device. Hereinafter, with regard to the embodiment illustrated in FIG. 24, a description for the same configuration as that in FIG. 22 will be partially omitted.

As illustrated in FIG. 24, the light irradiator 30 irradiates droplets discharged from the droplet discharger 10 with light. The light irradiator 30 is electrically coupled to the driver 20. The driver 20 inputs a synchronization signal to the light irradiator 30. As the synchronization signal is input to the light irradiator 30, the light irradiator 30 irradiates the droplet 210 with the laser beams 301 and 314, serving as illumination light, in synchronization with a discharge of the droplet 210 by the droplet discharger 10.

The light irradiator 30 includes the deflector 35 as a part thereof. After the light irradiator 30 irradiates the droplet 210 with the laser beam 301, the deflector 35 reflects the laser beam 313 that propagates behind the droplet 210 to deflect the laser beam 313 by 180 degrees in the propagation direction thereof. As a result, the laser beam 313 becomes a laser beam 314 propagating toward the droplet 210 again. The laser beam 314 irradiates the droplet 210 again, and furthermore, illuminates the fluorescent particles 201 existing in the droplet 210 again with illumination light from a direction different from the laser beam 301 by 180 degrees, thus greatly increasing the amount of light illuminating the fluorescent particles 201.

In the particle counting apparatus 100K illustrated in FIG. 24, the frequency with which the amount of light illuminating the fluorescent particles 201 contained in the droplet 210 becomes extremely small although the original amount of emitted laser light is the same can be more reduced compared to the case of the embodiment illustrated in FIG. 18 in which the laser beam 301 and the laser beam 311 are emitted from two different directions forming an angle of 45 degrees therebetween, thus improving the measurement accuracy.

Tenth Embodiment

Figure 25A:
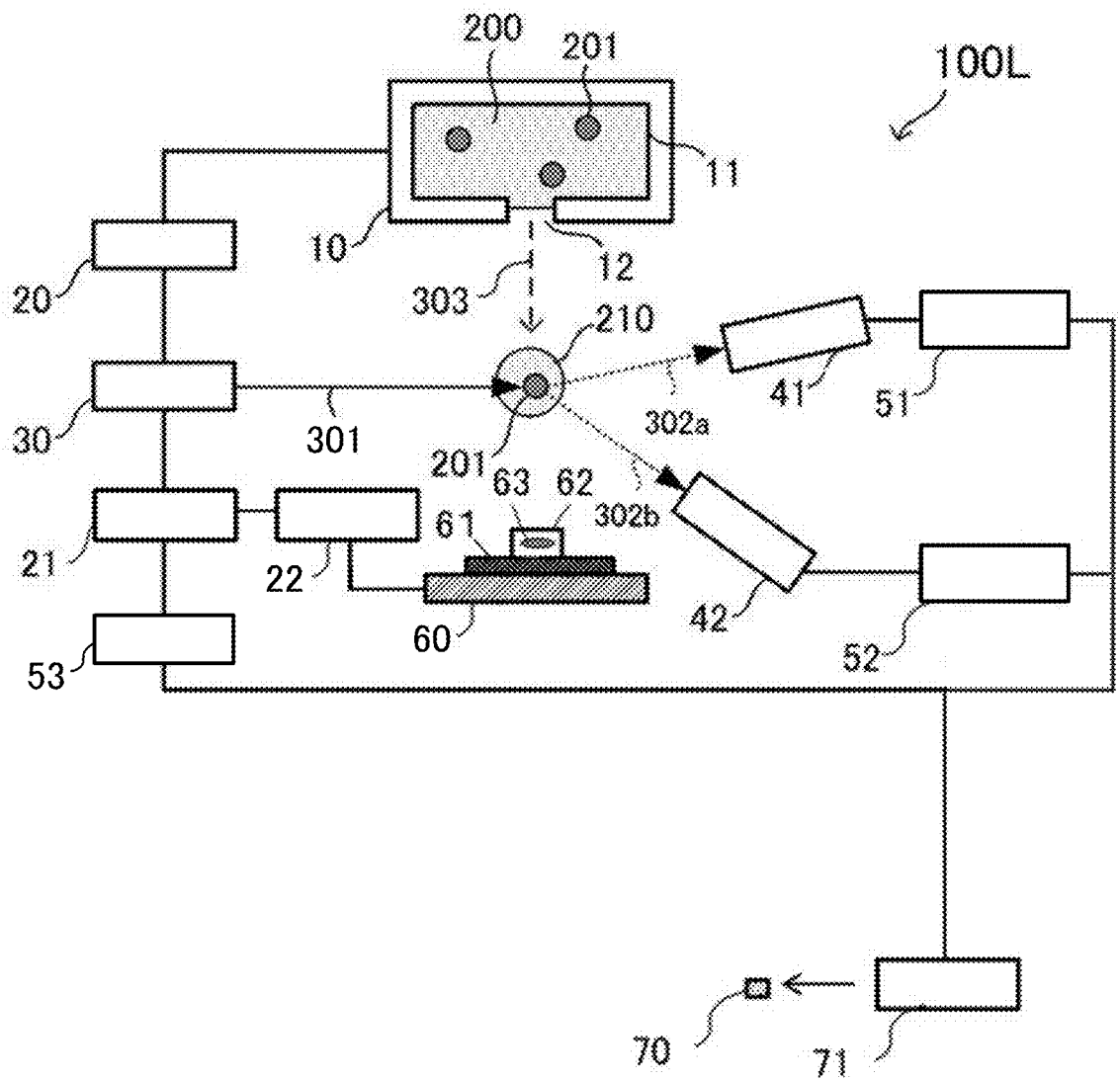
FIG. 25A is a schematic diagram of a particle counting apparatus according to a tenth embodiment.
Figure 25B:
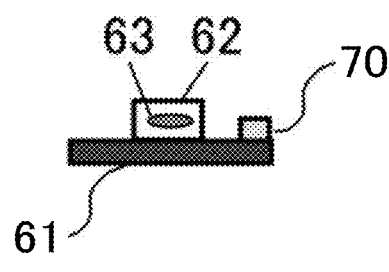
FIG. 25B is a schematic diagram of a particle containing sample according to the tenth embodiment.
Figure 25C:
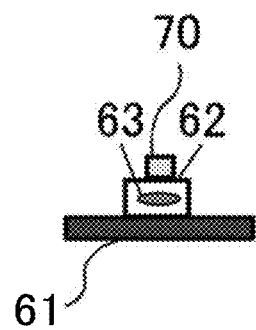
FIG. 25C is a schematic diagram of another particle containing sample according to the tenth embodiment.

FIGS. 25A, 25B, and 25C are schematic diagrams of a particle counting apparatus according to a tenth embodiment. The particle counting apparatus according to the tenth embodiment illustrated in FIGS. 25A, 25B, and 25C has a similar configuration to the particle counting apparatus according to the third embodiment illustrated in FIG. 9, but is different in that the microplate onto which droplets containing fluorescent particles are discharged is provided with an information storage.

Referring to FIGS. 25A, 25B, and 25C, a particle counting apparatus 100L includes a droplet discharger 10 equipped with a liquid chamber 11 and a nozzle 12, a driver 20, a light irradiator 30, light receivers 41 and 42, a first particle measuring device 51, a second particle measuring device 52, a droplet counter controller 53, a droplet discharger controller 21, a continuous discharge position controller 22, a droplet discharge position mover 60, a microplate 61, and a count information storage output unit 71 that outputs a count information storage 70. A particle containing sample 62 containing a fluorescent particle 63 is landed on the microplate 61. A particle suspension 200 contains fluorescent particles 201. A droplet 210 is discharged from the nozzle 12 of the droplet discharger 10 in a discharge direction 303. Laser beam 301 is emitted by the light irradiator 30. Light beam 302a is received by the light receiver 41. Light beam 302b is received by the light receiver 42.

Hereinafter, with regard to the tenth embodiment illustrated in FIGS. 25A, 25B, and 25C, a description for the same configuration as that in FIG. 9 will be partially omitted. The particle counting apparatus 100L illustrated in FIG. 25A continuously discharges droplets to the predetermined droplet discharge position, i.e., a specific well on the microplate 61, by a similar operation to that in the third embodiment illustrated in FIG. 9. Thus, the predetermined number of fluorescent particles measured with high accuracy are landed thereon. Thus, the particle containing sample 62 containing a predetermined number of fluorescent particles 63 is provided to a specific well.

The particle counting apparatus 100L illustrated in FIG. 25A further includes, in addition to the components according to the third embodiment, a count information storage output unit 71 that acquires count information on the particle containing sample 62 from the first particle measuring device 51 and the second particle measuring device 52 and outputs the count information storage 70 storing the count information. The count information storage output unit 71 may output the count information storage 70 either at once after the particle containing sample 62 containing a predetermined number of the fluorescent particles 63 is provided to all the predetermined specific wells on the microplate 61 or each time the particle containing sample 62 containing a predetermined number of fluorescent particles 63 is provided to each of the specific wells.

As illustrated in FIG. 25B, the count information storage 70 is installed to a part of the microplate 61 by a count information storage installation unit after the microplate 61 has been taken out of the particle counting apparatus 100L. Thus, the particle containing sample 62, the microplate 61, and the count information storage 70 are integrated as a particle containing sample. The count information storage 70 may be, for example, a bar code, an image label, or a text label. The count information storage installation unit is an output device dedicated to the count information storage 70. The count information storage 70 installed to a part of the microplate 61 is not limited to the above-described printed matter, and may be an RF-ID, a memory chip, a hologram, an optical memory, a microstructure having information on a microstructure, etc.

The installation configuration of the count information storage 70 to the particle containing sample 62 is not limited to that illustrated in FIG. 25B and may be that illustrated in FIG. 25C in which the count information storage 70 is installed on the particle containing sample 62 integrated with the microplate 61 by the count information storage installation unit after the microplate 61 has been taken out of the particle counting apparatus 100L. Thus, the microplate 61, the particle containing sample 62, and the count information storage 70 are integrated as a particle containing sample.

The installation configuration of the count information storage 70 to the particle containing sample 62 is not limited to those illustrated in FIGS. 25B and 25C. The count information storage 70 may be a chemical substance or material such as a protein, a low-molecular-weight compound, a fluorescent dye, DNA, and beads, so that the count information can be discriminated based on the difference in type and amount thereof. Such a count information storage 70 may be mixed with the particle containing sample 62 or the fluorescent particles 63 in the particle containing sample 62 to be integrated therewith. Further, the count information storage 70 may be a precursor material to be reacted with the particle containing sample 62 or the fluorescent particles 63 in the particle containing sample 62, so that the count information can be discriminated based on the difference in type and amount of chemical substances or materials obtained from the reaction therebetween.

The microplate 61, to which the droplet 210 is to be adhered for providing or integrating the particle containing sample 62, is not limited to the above-described configuration, and those having an adherable structure, such as a printing sheet, a bead, a reagent bin, and a capsule, may be used therefor. Further, the microplate 61, to which the droplet 210 is to be adhered, may be deformed by the count information storage installation unit and directly used as the count information storage 70. For example, a marking may be made on the microplate 61 by a laser marker or an inkjet device serving as the count information storage installation unit.

The count information storage 70 provided to the particle containing sample 62 is not limited to store the count value for each particle containing sample 62, and may also store peripheral information such as an ID, lot, specification, uncertainty, counting condition, information on the particle containing sample other than fluorescent particles, prescription information of the particle containing sample 62, and the like. Further, the count information storage 70 may store only IS as the minimum information and acquire necessary count information by linking with a separate count information storage provider. Examples of the separate count information storage provider include, but are not limited to, print data provided simultaneously with the particle containing sample 62, digital data, a program for processing digital data, and a cloud system for providing digital data.

The particle containing sample 62 can be used for calibration curves, detection limit verification, and accuracy guarantee in various measurements utilizing the fact that the number of the particles is known. For example, the microplate 61 in which the number of cells is changed, where the cell being the fluorescent particle 201, is useful for quantitative or qualitative analysis such as a real time polymerase chain reaction (real time PCR) for analyzing a unique gene to a cell type and a loop mediated isothermal amplification (LAMP) method for genetic test. Analysis of the genes of the cells is used as cell detection. Such an analysis is useful for food inspection. For example, in order to prevent food poisoning and analyze the cause thereof, bacteria such as enterohemorrhagic *Escherichia coli* (pathogenic *E. coli* O157), pathogenic *Escherichia coli* (other than O157), *Salmonella, Campylobacter, Staphylococcus aureus*, and *Vibrio parahaemolyticus* can be micro-analyzed at the level of one cell or several cells.

The user handles the microplate 61 provided with the particle containing sample 62 while wearing gloves, and performs opening of a microplate seal, opening and closing of a reagent bottle, pipetting, or aspirating or discarding of a solution. At the same time, the user needs to check information such as the sample number and content and furthermore to record his own work, which is very poor at workability. The particle containing sample 62 according to the tenth embodiment illustrated in FIGS. 25A, 25B, and 25C together with a reading device for the count information storage 70 provides analysis work having high workability.

Particle Containing Sample

A particle containing sample according to an embodiment comprises a count information storage storing information on the number of particles counted by the above-described particle counting apparatus and optional members.

Numerous additional modifications and variations are possible in light of the above teachings. It is therefore to be understood that, within the scope of the above teachings, the present disclosure may be practiced otherwise than as specifically described herein. With some embodiments having thus been described, it will be obvious that the same may be varied in many ways. Such variations are not to be regarded as a departure from the scope of the present disclosure and appended claims, and all such modifications are intended to be included within the scope of the present disclosure and appended claims.

The invention claimed is:

1. A particle counting apparatus comprising:
 a droplet discharger configured to discharge a droplet, as a flying droplet, containing at least one luminescent particle capable of emitting light upon receiving light;
 a light irradiator configured to irradiate the droplet discharged by the droplet discharger with light;
 at least one light receiver configured to receive light emitted by the at least one luminescent particle irradiated with the light emitted by the light irradiator; and
 circuitry configured to perform,
 a first particle measurement to measure the presence or absence of the luminescent particles contained in the droplet,
 a second particle measurement to measure the number of the luminescent particles contained in the droplet,
 wherein the first particle measurement further includes acquiring, by the at least one light receiver, an amount of light emitted by the at least one luminescent particle, and
 wherein the second particle measurement further includes acquiring a two-dimensional image based on the light emitted by the at least one luminescent particle.

2. The particle counting apparatus of claim 1, wherein the circuitry is configured to
 measure the number of the luminescent particles contained in the droplet, based on information from the first particle measuring device that a luminescent particle is present in the droplet; and
 control the droplet discharger, based on information from the second particle measuring device on the number of the luminescent particles contained in the droplet, or based on information from the first particle measuring device that a luminescent particle is absent in the droplet without using any information from the second particle measuring device.

3. The particle counting apparatus of claim 2, wherein the circuitry is configured to control a droplet discharge position such that droplets are continuously discharged to a substantially same position based on information from the first particle measuring device that a luminescent particle is absent in the droplet.

4. The particle counting apparatus of claim 1,
 wherein the at least one light receiver includes two or more light receivers configured to receive light beams emitted in two or more different directions, respectively, and a first light receiver of the two or more light receivers is coupled to the first particle measuring device.

5. The particle counting apparatus of claim 4,
 wherein a second light receiver of the two or more light receivers is coupled to the second particle measuring device.

6. The particle counting apparatus of claim 4, wherein a second light receiver of the two or more light receivers includes a field programmable gate array (FPGA).

7. The particle counting apparatus of claim 1, wherein the first particle measuring device acquires the amount of light emitted by the at least one luminescent particle based on the two-dimensional image acquired by the second particle measuring device.

8. The particle counting apparatus of claim 1, wherein the light irradiator is configured to emit light from two or more different directions.

9. The particle counting apparatus of claim 8, wherein the two or more different directions are substantially opposite directions to each other.

10. The particle counting apparatus of claim 9, wherein the light irradiator includes:
 a first light irradiator configured to irradiate the droplet with a substantially parallel light flux; and
 a second light irradiator including an optical deflector element, configured to deflect the substantially parallel light flux transmitted the droplet, in response to irradiation of the droplet with a part of the substantially parallel light flux, to irradiate the droplet again.

11. The particle counting apparatus of claim 1, wherein the light irradiator is configured to emit light in synchronization with the discharge of the droplet from the droplet discharger.

12. The particle counting apparatus of claim 11, wherein the synchronization is based on the light irradiator emitting the light with a delay of a predetermined time period from the discharge of the droplet from the droplet discharger.

13. The particle counting apparatus of claim 11, wherein the at least one light receiver is configured to receive the light in synchronization with the emission of the light by the light irradiator.

14. A particle containing sample comprising a count information storage storing information on the number of particles counted by the particle counting apparatus of claim 1.

15. A particle counting method, implemented by a particle counting apparatus, comprising:
 discharging, by a droplet discharger, a droplet, as a flying droplet, containing at least one luminescent particle capable of emitting light upon receiving light;
 irradiating, by a light irradiator, the droplet discharged in the discharging with light;

receiving, by at least one light receiver, light emitted by the at least one luminescent particle irradiated with the light; and counting, by circuitry, luminescent particles contained in the droplet based on the light received in the receiving, the counting including:

firstly measuring a presence or absence of the luminescent particles contained in the droplet; and secondly measuring the number of the luminescent particles contained in the droplet, wherein the firstly measuring further includes acquiring an amount of light emitted by the at least one luminescent particle, and wherein the secondly measuring further includes acquiring a two-dimensional image based on the light emitted by the at least one luminescent particle.

16. The particle counting method of claim 15, further comprising:

controlling, by the circuitry, the discharging, based on information from the secondly measuring on the number of the luminescent particles contained in the droplet, or based on information from the firstly measuring that a luminescent particle is absent in the droplet without using any information from the secondly measuring.

17. The particle counting method of claim 16, wherein the controlling the discharging includes accumulating the number of luminescent particles based on the information from the secondly measuring on the number of the luminescent particles contained in the droplet.

18. The particle counting method of claim 15, further comprising:

controlling, by the circuitry, a droplet discharge position such that droplets are continuously discharged to a substantially same position based on information from the firstly measuring that a luminescent particle is absent in the droplet; and moving the droplet discharge position based on information from the controlling.

* * * * *